US011590081B1

(12) United States Patent
Mehta et al.

(10) Patent No.: US 11,590,081 B1
(45) Date of Patent: Feb. 28, 2023

(54) EXTENDED RELEASE AMPHETAMINE TABLETS

(71) Applicant: Tris Pharma, Inc., Monmouth Junction, NJ (US)

(72) Inventors: Ketan Mehta, Miami, FL (US); Kalyan Kathala, Monmouth Junction, NJ (US)

(73) Assignee: TRIS PHARMA, INC, Monmouth Junction, NJ (US)

( * ) Notice: Subject to any disclaimer, the term of this patent is extended or adjusted under 35 U.S.C. 154(b) by 0 days.

(21) Appl. No.: 16/139,251

(22) Filed: Sep. 24, 2018

Related U.S. Application Data

(60) Provisional application No. 62/562,464, filed on Sep. 24, 2017.

(51) Int. Cl.
*A61K 9/20* (2006.01)
*A61K 31/137* (2006.01)
*A61K 9/28* (2006.01)
*A61P 25/00* (2006.01)
*A61K 9/00* (2006.01)
*A61K 47/14* (2017.01)

(52) U.S. Cl.
CPC .......... *A61K 9/2077* (2013.01); *A61K 9/0056* (2013.01); *A61K 9/284* (2013.01); *A61K 9/2866* (2013.01); *A61K 31/137* (2013.01); *A61K 47/14* (2013.01); *A61P 25/00* (2018.01)

(58) Field of Classification Search
CPC .............................. A61K 9/2077; A61P 25/00
See application file for complete search history.

(56) References Cited

U.S. PATENT DOCUMENTS

| | | |
|---|---|---|
| 659,463 A | 10/1900 | Woods |
| 692,988 A | 2/1902 | Davis |
| 2,099,402 A | 11/1937 | Keller |
| 2,507,631 A | 5/1950 | Hartmann |
| 2,809,918 A | 10/1957 | Hermelin |
| 2,830,933 A | 4/1958 | Bouchard |
| 2,906,665 A | 9/1959 | Doyle |
| 2,957,880 A | 10/1960 | Rudolf |
| 2,990,332 A | 6/1961 | Keating |
| 3,028,430 A | 4/1962 | Gillingham |
| 3,048,526 A | 8/1962 | Boswell |
| 3,089,824 A | 5/1963 | Wurster |
| 3,117,027 A | 1/1964 | Lindlof et al. |
| 3,138,525 A | 6/1964 | Koff |
| 3,253,944 A | 5/1966 | Wurster |
| 3,365,365 A | 1/1968 | Butler |
| 3,499,960 A | 3/1970 | Macek |
| 3,594,470 A | 7/1971 | Borodkin |
| 3,979,349 A | 9/1976 | Fink |
| 4,221,778 A | 9/1980 | Raghunathan |
| 4,459,278 A | 7/1984 | Porter |
| 4,510,128 A | 4/1985 | Khanna |
| 4,600,645 A | 7/1986 | Ghebre-Sallasie |
| 4,619,934 A | 10/1986 | Sunshine |
| 4,752,470 A | 6/1988 | Mehta et al. |
| 4,762,709 A | 8/1988 | Sheumaker |
| 4,765,989 A | 8/1988 | Wong |
| 4,775,536 A | 10/1988 | Patell |
| 4,794,001 A | 12/1988 | Mehta |
| 4,808,411 A | 2/1989 | Fu |
| 4,847,077 A | 7/1989 | Raghunathan |
| 4,859,461 A | 8/1989 | Chow |
| 4,871,549 A | 10/1989 | Veda |
| 4,876,094 A | 10/1989 | Benton |
| 4,891,549 A | 1/1990 | Geoghegan |
| 4,894,239 A | 1/1990 | Nonomura |
| 4,952,402 A | 8/1990 | Sparks |
| 4,961,932 A | 10/1990 | Theeuwes |
| 4,996,047 A | 2/1991 | Kelleher et al. |
| 4,996,058 A | 2/1991 | Sinnreich |
| 4,999,189 A | 3/1991 | Kogan |
| 5,071,646 A | 12/1991 | Malkowska |

(Continued)

FOREIGN PATENT DOCUMENTS

| | | |
|---|---|---|
| BE | 729827 | 9/1969 |
| CA | 2758556 | 5/2013 |

(Continued)

OTHER PUBLICATIONS

US 7,431,994 B2, 10/2008, Mehta (withdrawn)
Berman et al., Potential adverse effects of amphetamine treatment on brain and behavior: a review, Mol Psychiatry, vol. 14(2):123-142, Feb. 2009.
FDA.org, Adderall® IR Prescribing Information, Barr Laboratories, Inc., pp. 4-5, Mar. 2007.
Heal et al., Amphetamine, past and present—a pharmacological and clinical perspective, J. Psychopharmacol, vol. 27(6):479-496, Jun. 2013.
US Department of Health and Human Services, Guidance for Industry: Food Effect Bioavailability and Fed Bioequivalence Studies, Rockville, MD: Center for Drug Evaluation and Research, Dec. 2002.
US Department of Health and Human Services, Guidance for Industry: Bioavailability and Bioequivalence Studies for Orally Administered Drug Products—General Considerations, Washington, DC: Center for Drug Evaluation and Research, Mar. 2003.

(Continued)

*Primary Examiner* — Gina C Justice
(74) *Attorney, Agent, or Firm* — Howson & Howson; Cathy A. Kodroff

(57) ABSTRACT

An oral amphetamine extended release solid dose is described. The compositions contain a combination of an uncoated amphetamine-cation exchange resin complex, a barrier coated amphetamine—cation exchange resin complex—matrix, and an uncomplexed amphetamine, wherein one or more of these components contains blends of different forms of amphetamines. Either the modified release coated and/or the uncoated amphetamine—cation exchange resin complex may have two forms of amphetamine in a complex with a single cation exchange resin. Following administration of a single dose of the composition, a therapeutically effective amount of amphetamine is reached by about one hour and the composition provides at least a thirteen hour effect post-dose.

37 Claims, 2 Drawing Sheets

(56) References Cited

U.S. PATENT DOCUMENTS

| | | |
|---|---|---|
| 5,093,200 A | 3/1992 | Watanabe |
| 5,156,850 A | 10/1992 | Wong et al. |
| 5,158,777 A | 10/1992 | Abramowitz |
| 5,186,930 A | 2/1993 | Kogan et al. |
| 5,219,563 A | 6/1993 | Douglas |
| 5,260,068 A | 11/1993 | Chen |
| 5,273,760 A | 12/1993 | Oshlack |
| 5,275,819 A | 1/1994 | Amer |
| 5,275,820 A | 1/1994 | Chang |
| 5,286,493 A | 2/1994 | Oshlack |
| 5,296,236 A | 3/1994 | Santus |
| 5,368,852 A | 11/1994 | Umemoto |
| 5,374,659 A | 12/1994 | Gowan, Jr. |
| 5,409,907 A | 4/1995 | Blase |
| 5,411,745 A | 5/1995 | Oshlack |
| 5,422,121 A | 6/1995 | Lehmann |
| 5,496,561 A | 3/1996 | Okada |
| 5,580,578 A | 12/1996 | Oshlack |
| 5,609,835 A | 3/1997 | Pitcher |
| 5,837,284 A | 11/1998 | Mehta |
| 5,874,090 A | 2/1999 | Baker |
| 5,908,850 A | 6/1999 | Zeitlin |
| 5,968,551 A | 10/1999 | Oshlack |
| 5,980,088 A | 11/1999 | Iwasaki |
| 5,980,882 A | 11/1999 | Eichman |
| 6,001,392 A | 12/1999 | Wen et al. |
| 6,026,277 A | 2/2000 | Gavrilovich |
| 6,046,277 A | 4/2000 | Kolter |
| 6,066,334 A | 5/2000 | Kolter et al. |
| 6,217,904 B1 | 4/2001 | Midha |
| 6,228,398 B1 | 5/2001 | Devane |
| 6,228,863 B1 | 5/2001 | Palermo |
| 6,231,936 B1 | 5/2001 | Kozimor |
| 6,322,011 B1 | 11/2001 | Burnside |
| 6,322,819 B1 | 11/2001 | Burnside |
| 6,326,027 B1 | 12/2001 | Miller |
| 6,344,215 B1 | 2/2002 | Bettman |
| 6,355,656 B1 | 3/2002 | Zeitlin |
| 6,384,020 B1 | 5/2002 | Flanner |
| 6,399,828 B1 | 6/2002 | Boswell et al. |
| 6,419,954 B1 | 7/2002 | Chu |
| 6,419,960 B1 | 7/2002 | Krishnamurthy |
| 6,432,440 B1 | 8/2002 | Watts |
| 6,436,430 B1 | 8/2002 | Mulye |
| 6,528,530 B2 | 3/2003 | Zeitlin |
| 6,551,617 B1 | 4/2003 | Corbo |
| 6,551,620 B2 | 4/2003 | Otterbeck |
| 6,555,127 B2 | 4/2003 | Steiner |
| 6,555,136 B2 | 4/2003 | Midha |
| 6,605,300 B1 | 8/2003 | Burnside |
| 6,627,635 B2 | 9/2003 | Palermo |
| 6,635,284 B2 | 10/2003 | Mehta |
| 6,667,058 B1 | 12/2003 | Goede et al. |
| 6,673,367 B1 | 1/2004 | Goldenheim |
| 6,696,088 B2 | 2/2004 | Ack |
| 6,730,325 B2 | 5/2004 | Devane |
| 6,913,768 B2 | 7/2005 | Couch |
| 6,919,373 B1 | 7/2005 | Lam |
| 6,939,029 B1 | 9/2005 | Stahel |
| 6,974,591 B2 | 12/2005 | Kendrup et al. |
| 7,067,116 B1 | 6/2006 | Bess et al. |
| 7,070,806 B2 | 7/2006 | Oshlack |
| 7,083,808 B2 | 8/2006 | Goldenheim |
| 7,115,631 B2 | 10/2006 | Zeitlin |
| 7,125,563 B2 | 10/2006 | Kumbhani |
| 7,144,587 B2 | 12/2006 | Oshlack |
| 7,153,497 B2 | 12/2006 | Hughes |
| 7,510,729 B2 | 3/2009 | Kolter |
| 7,611,730 B2 | 11/2009 | Bartholomaus |
| RE41,148 E | 2/2010 | Burnside et al. |
| 7,691,880 B2 | 4/2010 | Herman |
| 7,776,917 B2 | 8/2010 | Mickle |
| RE42,096 E | 2/2011 | Burnside et al. |
| 7,906,145 B2 | 3/2011 | Castan |
| 8,062,667 B2 | 11/2011 | Mehta et al. |
| 8,062,677 B2 | 11/2011 | Komorowski |
| 8,202,537 B2 | 6/2012 | Mehta et al. |
| 8,202,542 B1 | 6/2012 | Mehta |
| 8,287,848 B2 | 10/2012 | Mehta |
| 8,287,903 B2 | 10/2012 | Mehta et al. |
| 8,329,224 B2 | 12/2012 | Hall et al. |
| 8,337,890 B2 | 12/2012 | Mehta |
| 8,343,546 B2 | 1/2013 | Hall et al. |
| 8,465,765 B2 | 6/2013 | Mehta |
| 8,470,375 B1 | 6/2013 | McMahen |
| 8,487,134 B2 | 7/2013 | Meudt et al. |
| 8,491,935 B2 | 7/2013 | Mehta |
| 8,512,688 B2 | 8/2013 | Mehta |
| 8,512,759 B1 | 8/2013 | Mcmahen et al. |
| 8,563,033 B1 | 10/2013 | Mehta et al. |
| 8,597,684 B2 | 12/2013 | Mehta et al. |
| 8,709,491 B2 | 4/2014 | Tengler |
| 8,747,902 B2 | 6/2014 | Mehta et al. |
| 8,778,390 B2 | 7/2014 | Mehta |
| 8,790,700 B2 | 7/2014 | Mehta et al. |
| 8,840,924 B2 | 9/2014 | Tengler |
| 8,883,217 B2 | 11/2014 | Mehta et al. |
| 8,956,649 B2 | 2/2015 | Mehta |
| 8,999,386 B2 | 4/2015 | Tu et al. |
| 9,017,731 B2 | 4/2015 | Tengler |
| 9,040,083 B2 | 5/2015 | Mehta |
| 9,057,675 B2 | 6/2015 | Tengler |
| 9,072,680 B2 | 7/2015 | Tengler |
| 9,089,496 B2 | 7/2015 | Tengler |
| 9,180,100 B2 | 11/2015 | Tu |
| 9,180,104 B2 | 11/2015 | Nelson et al. |
| 9,198,864 B2 | 12/2015 | Mehta |
| 9,265,737 B2 | 2/2016 | Tengler |
| 9,295,642 B2 | 3/2016 | Tu et al. |
| 9,545,399 B2 | 1/2017 | Tu et al. |
| 9,675,703 B2 | 6/2017 | Mehta et al. |
| 9,675,704 B2 * | 6/2017 | Mehta .................... A61K 47/14 |
| 9,844,544 B2 | 12/2017 | Tu et al. |
| 10,857,143 B2 | 12/2020 | Tu et al. |
| 11,103,494 B2 | 8/2021 | Tu et al. |
| 11,103,495 B2 | 8/2021 | Tu et al. |
| 2001/0038852 A1 | 11/2001 | Kolter |
| 2001/0038853 A1 | 11/2001 | Kolter |
| 2001/0046472 A1 | 11/2001 | Steiner |
| 2002/0058061 A1 | 5/2002 | Midha et al. |
| 2002/0156133 A1 | 10/2002 | Bartholomaeus |
| 2003/0004177 A1 | 1/2003 | Kao |
| 2003/0099711 A1 | 5/2003 | Meadows et al. |
| 2003/0185873 A1 | 10/2003 | Chasin |
| 2004/0052849 A1 | 3/2004 | O'hare |
| 2004/0059002 A1 | 3/2004 | Couch |
| 2004/0096501 A1 | 5/2004 | Vaya |
| 2004/0126428 A1 | 7/2004 | Hughes |
| 2004/0131680 A1 | 7/2004 | Goldenheim et al. |
| 2004/0220277 A1 | 11/2004 | Couch et al. |
| 2004/0228830 A1 | 11/2004 | Hirsh |
| 2005/0003005 A1 | 1/2005 | Shimizu |
| 2005/0013792 A1 | 1/2005 | Hollenbeck |
| 2005/0013857 A1 | 1/2005 | Fu |
| 2005/0019393 A1 | 1/2005 | Augsburger |
| 2005/0036977 A1 | 2/2005 | Gole |
| 2005/0106246 A1 | 5/2005 | Byrd |
| 2005/0142097 A1 | 6/2005 | Deepak |
| 2005/0181050 A1 | 8/2005 | Hirsh |
| 2005/0232986 A1 | 10/2005 | Brown et al. |
| 2005/0232987 A1 | 10/2005 | Srinivasan et al. |
| 2005/0232993 A1 | 10/2005 | Brown et al. |
| 2005/0265955 A1 | 12/2005 | Raman |
| 2005/0266032 A1 | 12/2005 | Srinivasan et al. |
| 2006/0018933 A1 | 1/2006 | Vaya |
| 2006/0018934 A1 | 1/2006 | Vaya |
| 2006/0029664 A1 | 2/2006 | Srinivasan |
| 2006/0057205 A1 | 3/2006 | Srinivasan |
| 2006/0115529 A1 | 6/2006 | Jeong |
| 2006/0134148 A1 | 6/2006 | Hollenbeck |
| 2006/0134207 A1 | 6/2006 | Srinivasan |
| 2006/0135777 A1 | 6/2006 | Trafelet |
| 2006/0193877 A1 | 8/2006 | Tengler |
| 2006/0204587 A1 | 9/2006 | Kolter |

(56) References Cited

U.S. PATENT DOCUMENTS

| | | |
|---|---|---|
| 2006/0240105 A1 | 10/2006 | Devane |
| 2006/0240128 A1 | 10/2006 | Schlagheck |
| 2006/0263431 A1 | 11/2006 | Maloney |
| 2006/0286174 A1 | 12/2006 | Raman |
| 2007/0042955 A1 | 2/2007 | Mickle |
| 2007/0059270 A1 | 3/2007 | Hall |
| 2007/0092553 A1 | 4/2007 | Tengler |
| 2007/0140983 A1 | 6/2007 | Hall |
| 2007/0148239 A1 | 6/2007 | Hall et al. |
| 2007/0160675 A1 | 7/2007 | Devane |
| 2007/0215511 A1 | 9/2007 | Mehta et al. |
| 2007/0218140 A1 | 9/2007 | Tanabe |
| 2007/0264323 A1 | 11/2007 | Shojaei |
| 2008/0064694 A1 | 3/2008 | Heil |
| 2008/0075769 A1 | 3/2008 | Poestges |
| 2008/0118570 A1 | 5/2008 | Liu |
| 2008/0118571 A1 | 5/2008 | Lee |
| 2008/0260845 A1 | 10/2008 | Thassu |
| 2009/0011027 A1 | 1/2009 | Pathak |
| 2009/0176884 A1 | 7/2009 | Dickerson |
| 2009/0220611 A1 | 9/2009 | Dargelas |
| 2009/0221552 A1 | 9/2009 | Teicher |
| 2010/0104621 A1 | 4/2010 | Waldo |
| 2010/0166858 A1 | 7/2010 | Mehta |
| 2010/0260844 A1 | 10/2010 | Scicinski |
| 2010/0278901 A1 | 11/2010 | Tengler et al. |
| 2011/0117205 A1 | 5/2011 | Castan et al. |
| 2011/0262539 A1 | 10/2011 | Bosse |
| 2012/0015030 A1 | 1/2012 | Mehta |
| 2012/0135077 A1 | 5/2012 | Mehta |
| 2012/0148672 A1 | 6/2012 | Mehta |
| 2012/0157706 A1 | 6/2012 | Bauer et al. |
| 2013/0004452 A1 | 1/2013 | Mehta |
| 2013/0004571 A1 | 1/2013 | Mehta |
| 2013/0079415 A1 | 3/2013 | Vergnault et al. |
| 2013/0136797 A1 | 5/2013 | Mehta |
| 2013/0236554 A1 | 9/2013 | Tengler |
| 2013/0243689 A1 | 9/2013 | Tengler |
| 2013/0243869 A1 | 9/2013 | Tengler |
| 2013/0243871 A1 | 9/2013 | Tengler |
| 2014/0023705 A1 | 1/2014 | Tengler |
| 2014/0030348 A1 | 1/2014 | Tengler |
| 2014/0033806 A1 | 2/2014 | McMahen |
| 2014/0037728 A1 | 2/2014 | Tengler |
| 2014/0050796 A1 | 2/2014 | Tengler et al. |
| 2014/0093578 A1 | 4/2014 | Mehta |
| 2014/0112996 A1 | 4/2014 | Tengler et al. |
| 2014/0127306 A1 | 5/2014 | Mehta et al. |
| 2014/0212493 A1 | 7/2014 | Mehta et al. |
| 2014/0287038 A1 | 9/2014 | Mehta |
| 2014/0287041 A1 | 9/2014 | Tu |
| 2015/0024059 A1 | 1/2015 | Mehta et al. |
| 2015/0157574 A1 | 6/2015 | Tu |
| 2015/0182469 A1 | 7/2015 | Mehta et al. |
| 2016/0008312 A1 | 1/2016 | Nelson et al. |
| 2016/0143846 A1 | 5/2016 | Tu |
| 2016/0143854 A1 | 5/2016 | Tu |
| 2016/0158373 A1 | 6/2016 | Mehta |
| 2016/0310478 A1 | 10/2016 | Mehta et al. |
| 2017/0042873 A1 | 2/2017 | Mehta et al. |
| 2017/0042874 A1 | 2/2017 | Mehta et al. |

FOREIGN PATENT DOCUMENTS

| | | |
|---|---|---|
| CN | 1179450 | 4/1998 |
| DE | 2246037 | 4/1974 |
| EP | 0294103 | 12/1988 |
| EP | 0367746 | 5/1990 |
| EP | 0565301 | 10/1993 |
| EP | 0943341 | 9/1999 |
| EP | 1186293 | 3/2002 |
| EP | 1240897 | 9/2002 |
| EP | 1429728 | 6/2004 |
| GB | 1358001 | 6/1974 |
| JP | 01-287270 | 7/1990 |
| JP | H02-17912 | 7/1990 |
| JP | 05-279246 | 10/1993 |
| JP | H05-279247 | 10/1993 |
| JP | 2003-528910 | 9/2000 |
| JP | 2005-528910 | 9/2005 |
| JP | 2005-306778 | 11/2005 |
| WO | WO-1987/00044 | 1/1987 |
| WO | WO-1998/014168 | 4/1988 |
| WO | WO-1990/09168 | 8/1990 |
| WO | WO-1992/011871 | 7/1992 |
| WO | WO-1998/027961 | 7/1998 |
| WO | WO-2000/040224 | 7/2000 |
| WO | WO-2001/070194 | 9/2001 |
| WO | WO-2001/074336 | 10/2001 |
| WO | WO-2002/034234 | 5/2002 |
| WO | WO-2003/020242 | 3/2003 |
| WO | WO-2004/028267 | 4/2004 |
| WO | WO-2004/060357 | 7/2004 |
| WO | WO-2004/067039 | 8/2004 |
| WO | WO-2004/071501 | 8/2004 |
| WO | WO-2005/102269 | 11/2005 |
| WO | WO-2005/117843 | 12/2005 |
| WO | WO-2005/120468 | 12/2005 |
| WO | WO-2006/021426 | 3/2006 |
| WO | WO-2006/022996 | 3/2006 |
| WO | WO-2006/061700 | 6/2006 |
| WO | WO-2006/093938 | 9/2006 |
| WO | WO-2006/101536 | 9/2006 |
| WO | WO-2006/135362 | 12/2006 |
| WO | WO-2007/000779 | 1/2007 |
| WO | WO 2007/001300 | 1/2007 |
| WO | WO-2007/001300 | 1/2007 |
| WO | WO 2007/109104 | 9/2007 |
| WO | WO-2007/109104 | 9/2007 |
| WO | WO-2008/064163 | 5/2008 |
| WO | WO 2008/064163 | 5/2008 |
| WO | WO-2010/080787 | 7/2010 |
| WO | WO 2010/080787 | 7/2010 |
| WO | WO-2012/112140 | 8/2012 |
| WO | WO-2013/003622 | 1/2013 |
| WO | WO 2013/003622 | 1/2013 |

OTHER PUBLICATIONS

U.S. Appl. No. 62/562,464, filed Sep. 24, 2017.
"DrugFacts: Stimulant ADHD Medications—methyphenidate and Amphetamine", https://www.drugabuse.gov/publications/drugfacts/stimulant-adhd-medications-methylphenidate-amphetamines, revised Jan. 2014, accessed Sep. 1, 2016.
Active Ingredients, Ion Exchange Resins-Healthcare, Rohm Haas, pp. 1, www.F:/Heathcare_Website/deliquescence.htm (Feb. 9, 2006).
Adderall® Product Insert, revised Mar. 2007 and Adderall XR® Product Insert (revised Dec. 2013.).
Adjei et al., Single-dose pharmacokinetics of methylphenidate extended-release multiple layer beads administered as intact capsule or sprinkles versus methylphenidate immediate-release tablets (Ritalin(®)) in healthy adult volunteers, J Child Adolesc Psychopharmacol, vol. 24(10), Dec. 2014, pp. 570-578.
Ahmann, Placebo-Controlled Evaluation of Amphetamine Mixture-Dextroamphetamine Salts and Amphetamine Salts (Adderall): Efficacy Rate and Side Effects, Pediatrics, 1:1-11 (Jan. 2001).
Amberlite IRP and Duolite AP Ion Exchange Resins, Ion Exchange Resins-Healthcare, Rohm Haas, pp. 1, www F:/HeathcareWebsite/formulations_products.htm (Feb. 9, 2006).
Andrist, Comparative Psychotomimetic Effects of Stereoisomers of Amphetamine, Nature, 234:152-153 (Nov. 19, 1971).
Ansel et al. Pharmaceutical Dosage Forms and Drug Delivery Systems, 6$^{th}$ Ed. pp. 213-221, Williams & Watkins. Jan. 1, 1995.
Aoyama, Pharmacodynamic Modeling for Change of Locomotor Activity by Methylphenidate in Rats, Pharmaceutical Research, 14(11):1601-1606 (Nov. 1997).
Arnold, Levoamphetamine and Dextroamphetamine: Comparative Efficacy in the Hyperkinetic Syndrome, Archives of General Psychiatry, 27:816-822 (Dec. 1972).
AS Gehris et al., "Controlled Release of an Opiate Drug Using Ion Exchange Resin", AAPS 2014 Poster Submission downloaded from http:/abstracts.aaps.org/Verify/AAPS2014/PosterSubmssions/W4037.pdf, Sep. 30, 2015.

(56) References Cited

OTHER PUBLICATIONS

BASF Aktiengesellschaft, Contents, Introduction, pp. 1-13, 2004.
BASF, A New Sustained Release Excipient, ExAct, 3: 2 (Nov. 1999).
BASF, Product Catalog (2008).
BASF—Expertise in Health and Nutrition, Sustained Release Excipients, p. 1-13, Kollicoat® SR 30 D, Tackiness of Films as a Function of Type and Concentration of Plasticizer (2007).
Biederman, J., New-Generation Long-Acting Stimulants for the Treatment of Attention-Deficit/Hyperactivity Disorder, Medscape Psychiatry, vol. 8(2), Nov. 2003, pp. 1-10.
Bordawekar, Evaluation of Kollicoat® SR 30D as a Sustained Release Polymer Dispersion, BASF Corporation, University of Rhode Island, p. 25, AAPS Poster (2002).
Bordawekar, Evaluation of Polyvinyl Acetate Dispersion as a Sustained Release Polymer for Tablets, Drug Delivery, 13(2):121-131 (Mar. and Apr. 2006).
Borodkin, Polycarboxylic Avid Ion-Exchange Resin Adsorbates for Taste Coverage in Chewable Tablets, Journal of Pharmaceutical Science 60(10): 1523-1527 (Oct. 1971).
Bright et al., ADHD Perspectives: Current Trends and the Rationale For Transdermal Therapy, Supplement to Pediatric News, Oct. 2013, pp. 1-12.
Cascade et al., Short-acting versus Long-acting Medications for the Treatment of ADHD, Psychiatry(Edgemont), vol. 5(8), Aug. 2008, pp. 24-27.
Center of Drug Evaluation and Research, Guidance for Industry: Statistical Approaches to Establishing Bioequivalence, pp. 1-45 (Jan. 2001).
Chavez et al., An Update on Central Nervous System Stimulant Formulations in Children and Adolescents with Attention-Deficit/Hyperactivity Disorder, The Annals of Pharmacotherapy, vol. 43, Jun. 2009, pp. 1084-1095.
Childress et al., "Efficacy and Safety of Amphetamine Extended-Release Oral Suspension in Children with Attention-Deficit/Hyperactivity Disorder", Journal of Child and Adolescent Psychopharmacology, vol. 28(5):306-313, Jun. 2018.
Childress et al., "Efficacy and Safety of Amphetamine Extended-Release Oral Suspension (AMPH EROS) in Children with ADHD", 2018 NEI Congress, Poster 79, Nov. 2018.
Childress et al., "Open-Label Dose Optimization Study of an Amphetamine Extended-Release Oral Suspension in Children with Attention-Deficit/Hyperactivity Disorder", Presentation Poster 2.19, AACAP 65$^{th}$ Annual Meeting, Oct. 2018.
Childress et al., "Open-Label Dose Optimization Study of an Amphetamine Extended-Release Oral Suspension in Children with Attention-Deficit/Hyperactivity Disorder", 2018 NEI Congress, Poster 87, Nov. 2018.
CJ Teter et al., "Illicit Methylphenidate Use in an Undergraduate student Sample: Prevalence and Risk Factors", Pharmacotherapy, 2003: 23(5): 609-617.
Codeprex®, Product Label, marketed by UCB, Inc., Jun. 21, 2004.
Concerta®, Clinical Pharmacology and Biopharmaceutics Reviews, App. No. 21-121, Center for Drug Evaluation and Research, Jun. 2000.
Concerta®, Medical Reviews, App. No. 21-121, Center for Drug Evaluation and Research, Jul. 1999 (completed Mar. 2000).
Connors et al., Chemical Stability of Pharmaceuticals: A Handbook for Pharmacists (2$^{nd}$ Ed.), John Wiley & Sons, pp. 587-589., Jan. 1986.
Cutler et al., "Efficacy Measures in an Open-Label Dose-Optimization Study of an Amphetamine Extended—Release Oral Suspension in Children with Attention-Deficit/Hyperactivity Disorder", AACAP Abstract, Oct. 2018.
Cutler et al., "Efficacy Measures in an Open-Label Dose-Optimization of an Amphetamine Extended-Release Oral Suspension in Children with Attention-Deficit/Hyperactivity Disorder", NEI OL Abstract, Nov. 2018.
Cutler et al., "Open-Label Dose-Optimization of an Amphetamine Extended-Release Oral Suspension in Children with Attention-Deficit/Hyperactivity Disorder", NEI OL Abstract, Nov. 2018.
Dahl, T.C., Handbook of Pharmaceutical Excipients (6$^{th}$ Ed.): Ethylcellulose, Pharmaceutical Press, London, Feb. 2009, pp. 262-267.
Dashevsky, Compression of Pellets Coated with Various Aqueous Polymer Dispersions, International Journal of Pharmaceutics, 279(1-2):19-26 (Jul. 26, 2004).
Dashevsky, Physicochemical and Release Properties of Pellets Coated with Kollicoat SR 30 D, a New Aqueous Polyvinyl Acetate Dispersion for Extended Release, International Journal of Pharmaceutics, 290(1-2):15-23 (Feb. 16, 2005; E-publication: Jan. 6, 2005).
Daughton et al., "Review of ADHD Pharmacotherapies: Advantages, Disadvantages, and Clinical Pearls", J. Am. Acad. Child and Adolescent Psychiatry, vol. 48(3):240-248, Mar. 2009.
Daytrana® NDA Approval Letter from the Department of Health and Human Services dated Apr. 4, 2006, pp. 1-9.
Daytrana®, Clinical Pharmacology and Biopharmaceutics Reviews, App. No. 21-514, Center for Drug Evaluation and Research, Jun. 2005.
Daytrana®, Medical Reviews, App. No. 21-514, Center for Drug Evaluation and Research, Feb. 2006.
Degussa, Creating Essentials, Specifications and Test Methods for Eudragit® NE 30 D, p. 1-4 (Sep. 2004).
Deliquescent Drugs, Ion Exchange Resins-Healthcare, Rohm Haas, pp. 1, www.F:/Heathcare_Website/deliquescence.htm (Feb. 9, 2006).
Dissolution Enhancement of Poorly Soluble Drugs, Rohm Haas Ion Exchange Resins-Healthcare, pp. 1, www.rohmhaas.com (Dec. 1, 2004).
Draganoiu, Evaluation of the New Polyvinylacetate/Povidone Excipient for Matrix Sustained Release Dosage Forms, Pharm. Ind., 63:624-629 (2001).
Dyanavel™ XR product literature, revised Nov. 2015, (accessed at http://www.accessdata.fda.gov/drugsatfda_docs/iabel/2015/208147s0001b1.pdf) on Sep. 1, 2016.
Ebert et al., The Effects of Increasing Plasma Concentrations of Dexmedetomidine in Humans, Anesthesiology, vol. 93, Aug. 2000, pp. 382-394.
Eliminating Polymorphism, Ion Exchange Resins-Healthcare, Rohm Haas, www.F:/Heathcare_Website/polymorph.htm (Feb. 9, 2006).
El-Samaligy, Formulation and Evaluation of Sustained-Release Dextromethorphan Resinate Syrup, Egyptian Journal of Pharmaceutical Sciences, 37(1-6):509-519 (1996).
Erdmann, Coating of Different Drugs with Optimized Kollicoat EMM 30 D Coatings, BASF Aktiengesellschaft, Proceedings of the 26$^{th}$ CRS symposium (Jun. 1999), 6313.
Ermer et al., "Pharmacokinetic Variability of Long-Acting Stimulants in the Treatment of Children and Adults with Attention-Deficit/Hyperactivity Disorder", CNS Drugs, vol. 24(12):1009-1025, Dec. 2010.
Extended Release, RohmHaas Ion Exchange Resins-Healthcare, p. 1, Rohm and Haas website, www.rohmhaas.com (Feb. 9, 2005).
Faraone et al., The worldwide prevalence of ADHD: is it an American condition?, World Psychiatry, vol. 2(2), Jun. 2003, pp. 104-113.
FDA Guidance for Industry, SUPAC-MR: Modified Release Solid Oral Dosage Forms. Scale-Up and Postapproval Changes: Chemistry, Manufacturing, and Controls; In Vitro Dissolution Testing and In Vitro Bioequivalence Documentation, pp. 1-36 (Sep. 1997).
FDA Guidance for Industry: Specifications: Test Procedures and Acceptance Criteria for New Veterinary Drug Substances and New Medicinal Products: Chemical Substances, pp. 1-35 (Jun. 14, 2006).
fda.gov, Clinical Pharmacology and Biopharmaceutics Reviews: Concerta, retrieved from http://www.accessdata.fda.gov/drugsatfda_docs/nda/2000/21-121_Concerta_biopharmr.pdf on Jul. 15, 2016. Jun. 2000, pp. 1-112.
fda.gov, Clinical Pharmacology and Biopharmaceutics Reviews: Methylin, retrieved from http://www.accessdata.fda.gov/drugsatfda_docs/nda/2002/21-419_Methylin_BioPharmr.pdf on Jul. 14, 2016, Jul. 2001, pp. 1-54.
fda.gov, Drugs@FDA Frequently Asked Questions, retrieved at http://www.fda.gov/Drugs/InformationOnDrugs/ucm075234.htm on Jul. 18, 2016. Last updated Mar. 2015, pp. 1-7.

(56) References Cited

OTHER PUBLICATIONS fda.gov, Methylin® Oral Solution—NDA Approval Letter, retrieved from http://www.accessdata.fda.gov/drugsatfda_docs/appletter/2002/21419ltr.pdf on Jul. 15, 2016, Dec. 19, 2002, pp. 1-4.
fda.gov, Orange Book Listing: Metadate CD, retrieved from http://www.accessdata.fda.gov/scripts/cder/ob/docs/obdetail.cfm7Appl_No=021259&TABLE1=OB_Rx on Jul. 14, 2016, Apr. 2001, pp. 1-3.
fda.gov, Quillichew—NDA Approval Letter, retrieved from http://www.accessdata.fda.gov/drugsatfda_docs/appletter/2015/207960Orig1s000ltr.pdf on Jul. 8, 2016, Dec. 4, 2015, pp. 1-5.
Flynn, Buffers-pH Control within Pharmaceutical Systems, Parental Fundamentals, vol. 34(2), Mar. 1980, pp. 139-162.
Focalin® XR NDA Approval Letter from the Department of Health and Human Services, dated May 26, 2005.
Focalin® XR, Clinical Pharamacology and Biopharmaceutics Reviews, App. No. 21-802, Center for Drug Evaluation and Research, Jul. 2004.
Focalin® XR, Highlights of Prescribing Information, Label Revised Jan. 2012.
Focalin® XR, Medical Review, App. No. 21-802, Center for Drug Evaluation and Research, Jul. 2004.
Generic Drug Formulations with Kollicoat® SR 30 D and Kollidon® SR, pp. 1-51, BASF (1999).
Ghuman et al., "Psychopharmacological and Other Treatments in Preschool Children with Attention Deficit/Hyperactivity Disorder: Current Evidence and Practice", J. Child and Adolescent Psychopharmacology, vol. 18(5):413-447, Oct. 2008.
Gonzales et al., "Methylphenidate Bioavailability from Two Extended-Release Formulations", Int'l J. Clinical Pharmacology and Thereapeutics, vol. 40(4):175-184, Apr. 2002.
Greenhill et al. Double-Blind, Placebo-Controlled Study of Modified-Release Methylphenidate in Children With Attention-Deficit/Hyperactivity Disorder. Pediatrics. vol 109(3):1-7. Mar. 1, 2002.
Greenhill et al., Practice Parameter for the Use of Stimulant Medications in the Treatment of Children, Adolescents, and Adults, Child Adolesc. Psychiatry, vol. 41(2), Feb. 2002, pp. 26S-49S.
Haddish-Berhane, Modeling Film-Coat Non-Uniformity in Polymer Coated Pellets: A Stochastic Approach, International Journal of Pharmaceutics, 12; 323(1-2):64-71 (Oct. 2006; E-publication Jun. 6, 2006).
HC Kimko, Pharmacokinetcs and clinical effectiveness of methylphenidate, Clin Pharmacokinet, 1999; Dec. 37 (6): 457-70, Abstract.
Herman et al., "A Modified-Release Drug Delivery Technology Containing Amphetamine-Ion Exchange Complexes", Neuroscience Education Institute (NEI) LiquiXR Abstract, Sep. 12, 2018.
Herman et al., "A Novel, Modified Release Drug Delivery Technology Containing Amphetamine-Ion Exchange Complexes", NEI LiquiXR Abstract, May 2018.
Herman et al., "A Novel, Modified-Release Drug Delivery Technology Containing Amphetamine Ion-Exchange Complexes", 2018 NEI Congress, Poster 89, Nov. 2018.
Herman et al., "Early Onset Efficacy and Safety and Efficacy Pilot Study of Amphetamine Extended-Release Oral Suspension (AMPH EROS) in the Treatment of Children with ADHD", 2018 NEI Congress, Poster 32, Nov. 2018.
Herman et al., "Early-Onset Efficacy and Safety Pilot Study of Amphetamine Extended-Release Oral Suspension (AMPH EROS) in the Treatment of Children with Attention-Deficit/Hyperactivity Disorder", NEI EO Abstract, Nov. 2018.
Herman et al., "Single-Dose Pharmacokinetics of Amphetamine Extended-Release Tablet (AMPH ER TAB) Compared with Amphetamine Extended-Release Oral Suspension (AMPH EROS)", Presentation Poster 2.18, AACAP 65$^{th}$ Annual Meeting, Oct. 2018.
Herman et al., "Single-Dose Pharmacokinetics of Amphetamine Extended-Release Tablet (AMPH ER TAB) Compared with Amphetamine Extended-Release Oral Suspension (AMPH EROS)", AACAP Abstract, Oct. 2018.
Hinsvark, The oral bioavailability and pharmacokinetics of soluble and resin-bound forms of amphetamine and phentermine in man, Journal of Pharma and BioPharma, 1(4):319-328 (Aug. 1973).
Ichikawa, Use of Ion-Exchange Resins to Prepare 100 μm-Sized Microcapsules with Prolonged Drug-Release by the Wurster Process, International Journal of Pharmaceutics 216:67-76 (Mar. 2001).
Improved Dissolution of Poorly Soluble Drugs References, pp. 1, www.F:/Heathcare_Website/Poor_Solubility_refl.htm (Feb. 9, 2006).
IndustrialSpec.com, Mesh & Micron Sizes: Mesh to Micron Conversion Chart, p. 1, Aug. 27, 2015.
Ion Exchange Resins-Healthcare, Rohm Haas, Frequently Asked Questions, pp. 1-3, www.F:/Heathcare_Website/gaq_print.htm (Feb. 9, 2006).
Jeong, Development of Sustained Release Fast-melting Tablets Using Ion Exchange Resin Complexes (accepted Nov. 29, 2005), Dissertations Submitted to Purdue University, W. Lafayette, Indiana, UMI #3210729.
Jeong, Drug Release Properties of Polymer Coated Ion-Exchange Resin Complexes: Experimental and Theoretical Evaluation, Journal of Pharmaceutical Sciences, pp. 1-15 (Apr. 2006).
Jeong, Evaluation of Drug Release Properties from Polymer Coated Drug/Ion-Exchange Resin Complexes Using Mathematical Simulation and Their Application into Sustained Oral Drug Delivery, Department of Pharmaceutical Chemistry, University of Kansas, Abstract (Jun. 16-18, 2005), pp. 92-105, 114, 141, 169 (Dec. 2005).
JS Markowitz et al., "Pharmacokinetics of Methylphenidate After Oral Administration of Two Modified-Release Formulations in Healthy Adults", Clin Pharmacol., 42(4): 393-401 (2003).
JS Markowitz et al., "Ethylphenidate Formation in Human Subjects After Administration of a Single Dose of Methylphenidate and Ethanol", Drug Metabolism and Disposiiton, 28: 620-624 (2000).
Kando et al., "The Efficacy and Safety of Amphetamine Extended-Release Oral Suspension (AMPH EROS) in Children with Attention-Deficit/Hyperactivity Disorder", NEI Abstract, Nov. 2018.
Kessler et al., The prevalence and correlates of adult ADHD in the United States: Results from the National Comorbidity Survey Replication, Am J Psychiatry, vol. 163(4), Apr. 2006, pp. 716-723.
Kollicoat SR30D, Technical Information (Jan. 2004, Supercedes Jun. 1999) BASF, MEF/EP 073.
Kollicoat®—Film-Coating Technology by BASF, www.pharma-solutions.basf.com, BASF-Expertise in Health and Nutrition, pp. 13 (Dec. 2, 2004).
Kollicoat® SR 30 D, Polyvinyl Acetate Dispersion for Sustained-Release Pharmaceutical Formulations, Technical Information, BASF (Jun. 1999).
Kolter, Coated Drug Delivery Systems Based on Kollicoat® SR 30D, BASF, MEF/EP073 (Spring/Summer 2004).
Kolter, Influence of Additives on the Properties of Films and coated Dosage Forms, BASF ExAct, 5:4 (Oct. 2000).
Kolter, Kollicoat® SR 30 D, Coated Drug Delivery Systems, ExAct, 11:3 (Oct. 2003).
Kooij et al., European consensus statement on diagnosis and treatment of adult ADHD: The European Network Adult ADHD, BMC Psychiatry, vol. 10(67), Sep. 2010, pp. 1-24.
Kulshreshtha et al. (Eds.), Pharmaceutical Suspensions: From Formulation Development to Manufacturing, Springer Science & Business Media, Jan. 2009.
Laird et al., "The Efficacy and Safety of Amphetamine Extended-Release Oral Suspension (AMPH EROS) in Children with Attention-Deficit/Hyperactivity Disorder", SDBP Primary Data Abstract, Sep. 2018.
Laird et al., Efficacy and Safety of Amphetamine Extended-Release Oral Suspension in Children with ADHD, 2018 SDBP Conference, Poster 79, Sep. 2018.
Lasser, Comparative Efficacy and Safety of Lisdexamfetamine Dimesylate and Mixed Amphetamine Salts Extended Release in Adults with Attention Deficit/Hyperactivity Disorder, Primary Psychiatry, 17(9):44-54 (2010).
Mallinckrodt Inc., Methylin® Oral Solution (product label), retrieved from http://www.accessdata.fda.gov/drugsatfda_docs/label/2013/021419s0071b1.pdf on Jul. 14, 2016, Dec. 2013, pp. 1-16.

(56) References Cited

OTHER PUBLICATIONS

Markowitz et al., Advances in the pharmacotherapy of attention-deficit-hyperactivity disorder: focus on methylphenidate formulations, Pharmacotherapy, vol. 23(10), Oct. 2003, pp. 1281-1299.
Mehta and Kathala, U.S. Appl. No. 16/139,251, filed Sep. 24, 2018.
Metadate CD® NDA Approval Letter from the Department of Health and Human Services, dated Feb. 2, 2001.
Metadate CD®, Clinical Pharmacology and Biopharmaceutics Reviews, App. No. 21-259, Center for Drug Evaluation and Research, Mar. 2001.
Metadate CD®, Medical Reviews, App. No. 21-259, Center for Drug Evaluation and Research, Mar. 2000.
Metadate CD®, Product Label, 2013.
Methylin® ER NDA Approval Letter from the Department of Health and Human Services, dated May 9, 2000.
Methylin® ER, Approval Letter and Reviews, App. No. 75-629, Center for Drug Evaluation and Research, May 2000.
Methylin® ER, Product Label, marketed by Mallinckrodt Inc., Oct. 2013.
Methylin® Oral Solution, Chemistry Reviews, App. No. 21-419, Center for Drug Evaluation Research, May 2002.
Methylin® Oral Solution, Clinical Pharmacology and Biopharmaceutics Reviews, App. No. 21-419, Center for Drug Evaluation and Research, Jul. 2001.
Methylin® Oral Solution, Medical Reviews, App. No. 21-419, Center for Drug Evaluation and Research, May 2002.
Methylin® Oral Solution, Product Label, marketed by Mallinckrodt Inc., May 2006.
Mies, BASF, Pharmasolutions, MEMPD 130, Correlation of Drug Permeation Through Isolated Films and Coated Dosage Forms Based on Kollicoat 30SR D/IR, 2004 AAPS Annual Meeting and Exposition (Nov. 7-11, 2004).
MK Chourasia and SK Jain, Pharmaceutical approaches to colon targeted drug delivery systems, J Pharm Pharmaceutic Sci (www.ualberta.ca/-csps) 6(1): 33-66, 2003.
NDA20100, Clinical Pharmacology and Biopharmaceutics Review(s), Applicatoin No. 20100Orig1s000, Center for Drug Evaluation and Research, revised Mar. 21, 2011, http://www.accessdata.fda.gov/drugsatfda_docs/nda/2012/202100Orig1s000ClinPharmR.pdf.
Nextwave Pharmaceuticals, Inc., "QuilliChew ER—Methylphenidate HC1: Highlights of Prescribing Information", retrieved from http://labeling.pfizer.com/ShowLabeling.aspx?id=2577 on Jul. 8, 2016, Dec. 2015, pp. 1-14.
Nicotine, Ion Exchange Resins-Healthcare, Rohm Haas, www.F:/HeathcareWebsite/nicotin.htm (Feb. 9, 2006).
Nisar-UR-Rahman, Differential Scanning Calorimetry and Surface Morphology Studies on Coated Pellets using Aqueous Dispersions, Pakistan Journal of Pharmaceutical Sciences, 18(2):19-23 (Apr. 2005).
Novartis Consumer Health in Canada, Delsym, www.Novartisconsumerhealth.ca/en/products/delsym.shtml (2003).
Patrick et al., "Evolution of Stimulants to Treat ADHD: Transdermal Methylphenidate", Human Psychopharmacology, vol. 24(1):1-17, Jan. 2009.
Patrick et al., Evolution of stimulants to treat ADHD: transdermal methylphenidate, vol. 24(1), Hum Psychopharmacol, Jan. 2009, pp. 1-17.
Patrick et al., Influence of ethanol and gender on methylphenidate pharmacokinetics and pharmacodynamics, Clin Pharmacol Ther, vol. 81(3), Mar. 2007, pp. 346-353.
pdr.net, "Focalin® XR", Physician's Desk Reference, retrieved from http://www.pdr.net/drug-summary/Focalin-XR-dexcphenidate-hydrochloride-431.3616 on Jul. 14, 2016, Aug. 2010, pp. 2472-2477.
pdr.net, Ritalin LA, retrieved from http://www.pdr.net/drug-summary/Ritalin-LA-methylphenidate-hydrochloride-1003 on Jul. 14, 2016, Jan. 2006, pp. 1-3.
pdr.net, Tussionex, retrieved from http://www.pdr.net/drug-summary/Tussionex-chlorpheniramine-polistirex-hydrocodone-polistirex-579.2803 on Jul. 14, 2016. Jan. 2010, pp. 1-2.
Pearnchob, Coating with Extended Release, ExAct, 12:2-5 (Jun. 2004).
Pelham et al. Once-a-Day Concerta Methylphenidate Verses Three-Times-Daily Methylphenidate in Laboratory and Natural Settings. Pediatrics. vol. 107(6):1-15. Jun. 1, 2001.
Physician's Desk Reference: Adderall, 51st Ed. (1997).
Pliszka, Practice Parameter for the Assessment and Treatment of Children and Adolescents With Attention-Deficit/Hyperactivity Disorder, The AACAP Work Group on Quality Issues, J. Am. Acad. Child Adolesc. Psychiatry, vol. 46(7), Jul. 2007, pp. 894-921.
Polymorphism References, pp. 1, www.F:/HeathcareWebsite/polymorphreferences.htm (Feb. 9, 2006).
Prabhu, Comparison of Dissolution Profiles for Sustained Release Resinates of BCS Class 1 Drugs Using USP Apparatus 2 and 4: A Technical Note, AAPS PharmSciTech, 9(3):769-773 (Sep. 2008).
Prince, "Pharmacotherapy of Attention-Deficit/Hyperactivity Disorder in Children and Adolescents: Update on New Stimulant Preparations, Atomoxetine, and Novel Treatments", Child and Adolescent Psychiatric Clin N. Am., vol. 15:13-50, Jan. 2006.
Product Literature, Concerta®, (methylphenidate HC1) Extended-release Tablets, (revised Nov. 2010).
Product Literature, Daytrana® (methylphenidate transdermal system), revised Dec. 2009.
Product Literature, Focalin™ XR (dexmethylphenidate hydrochloride) extended-release capsules, Novartis Consumer Health, 2004.
Product Literature, Once Daily Metadate CD™ (methylphenidate HC1, USP) Extended-Release Capsules (Feb. 2007).
Product Literature, Ritalin® hydrochloride methylphenidate hydrochloride tablets USP and Ritalin-SR® methylphenidate hydrochloride USP sustained-release tablets (revised Dec. 2010).
Quadir, FDA Excipient Workshop, Development of High Functionality Excipients for Immediate and Sustained Release Dosage Forms (Sep. 20, 2004).
Quadir, Release Characteristics . . . of selected drugs with a newly developed polyvinyl acetate dispersion, ExAct, 13:4 (Dec. 2004).
Quillivant® XR NDA Approval Letter from the Department of Health and Human Services, dated Sep. 27, 2012.
Quiilivant® XR, Highlights of Prescribing Information, Label Revised Dec. 2013.
Raghunathan, Sustained-release Drug Delivery System 1: Coated ion-exchange Resin System for Phenylpropanolamine and Other Drugs, Journal of Pharmaceutical Science, 70:379-384 (Apr. 1981).
Remington: The Science and Practice of Pharmacy, 19th Ed., vol. II, pp. 1653-1658 (1995).
Ritalin LA®, Clinical Pharmacology and Biopharmaceutics Reviews, App. No. 21-284, Center for Drug Evaluation and Research, Dec. 2001.
Ritalin LA®, Medical Review(s), App. No. 21-284, Center for Drug Evaluation and Research, Nov. 2000.
Ritalin-LA® NDA Approval Letter from the Department of Health and Human Services, dated Jun. 5, 2002.
Ritalin-LA®, Product Label, Dec. 13, 2013.
Ritalin-SR® NDA Approval Letter from the Department of Health and Human Services, dated May 21, 2004.
RITALIN-SR®, Product Label, Dec. 13, 2013.
RJ Meyer and AS Hussaain, "FDA's ACPS Meeting, Oct. 2005 Awareness Topic: Mitigating the Risks of Ethanol Induced Dose Dumping from Oral Sustained/Controlled Release Dosage Forms", Oct. 2005, http://www.fda.gov/ohrms/dockets/ac/05/briefing/2005-4187B1_01_08-Alcohol-Induced.pdf.
Robinson, Sustained and Controlled Release Drug Delivery Systems, Drugs and the Pharmaceutical Sciences, A Series of Textbooks and Monographs, vols. 1-6, pp. 130-210, by Marcel Dekker, Inc., New York and Basel (1978).
Rodriguez-Torres et al., Effect of ribavirin on intracellular and plasma pharmacokinetics of nucleoside reverse transcriptase inhibitors in patients with human immunodeficiency virus-hepatitis C virus coinfection: results of a randomized clinical study, Antimicrob Agents Chemother, vol. 49(10), Oct. 2005, pp. 3997-4008.
Rowe, Materials Used in the Film Coating of Oral Dosage Forms, Critical Reports in Applied Chemistry, 6:1-16 (1984).

(56) References Cited

OTHER PUBLICATIONS

S M Outram, "The Use of methylphenidate among students: the future of enhancement?" J Med Ethics, 2010: 36: 198-2020, downloaded by http://jme.bmj.com on Sep. 1, 2016.

Sawicki, Compressibility of Floating Pellets with Verapamil Hydrochloride Coated with Dispersion Kollicoat SR 30 D, European Journal of Pharmaceutics and Biopharmaceutics, 60(1):153-8 (May 2005; E-publication: Jan. 8, 2005).

Schapperer et al., Bioequivalence of Sandoz methylphenidate osmotic-controlled release tablet with Concerta® (Janssen-Cilag), Pharmacol Res Perspect, vol. 3(1), Feb. 2015, pp. e00072.

Shao, Drug Release Form Kollicoat SR 30D-Coated Nonpareil Beads: Evaluation of Coating Level, Plasticizer Type, and Curing Condition, pp. 1-9, PharmSci Tech, 3(2):article 15 (Jun. 2002).

Shao, Effects of Formulation Variables and Post-Compression Curing on Drug Release from a New Sustained-Release Matrix Material: Polyvinylacetate-Povidone, Pharmaceutical Development and Technology, 6(2):247-254 (2001).

Stearns et al., Active tamoxifen metabolite plasma concentrations after coadministration of tamoxifen and the selective serotonin reuptake inhibitor paroxetine, J Natl Cancer Inst, vol. 95(23), Dec. 2003, pp. 1758-1764.

Stier et al., Use of partial area under the curve metrics to assess bioequivalence of methylphenidate multiphasic modified release formulations, AAPS J, vol. 14(4), Dec. 2012, pp. 925-926.

Strübing, Mechanistic Analysis of Drug Release From Tablets with Membrane Controlled Drug Delivery, European Journal of Pharmaceutics and Biopharmaceuticals, 66(1):113-9 (Apr. 2007; E-publication: Sep. 28, 2006).

Swanson et al., "Comparison of Once-Daily Extended Release methylphenidate Formulations in Children With Attention-Deficit/Hyperactivity Disorder in the Laboratory School (The Comacs Study)", Pediatrics, vol. 113(3):206-16, Mar. 2004.

Swanson et al., Development of a new once-a-day formulation of methylphenidate for the treatment of attention-deficit/hyperactivity disorder: proof-of-concept and proof-of-product studies, Arch Gen Psychiatry, vol. 60(2), Feb. 2003, pp. 204-211.

Swarbrick, Suspensions in Remington: The Science and Practice of Pharmacy, $20^{th}$ Edition, ed. Gennaro, Lippincott, 2000, pp. 316-323.

T Spencer et al., "Effiacy of a Mixed Amphetamine Salts of Compound in Adults with Attention-Deficit/Hyperactivity Disorder", Arch Gen Psychiatry, 2001, 58: 775-782.

Taste Masking, Ion Exchange Resins-Healthcare, Rohm Haas, pp. 1, www.F:/Heathcare_Website/tastemasking.htm (Feb. 9, 2006).

The Dow Chemical Company, Ethocel: Ethylcellulose Polymers Technical Handbook, Sep. 2005, pp. 1-28.

The Pharmacopeia of the United States ($25^{th}$ revision), "Pharmaceutical Dosage Forms", pp. 2213-2225, Nov. 2001.

The Physicians' Desk Reference ($60^{th}$ ed.), "Concerta®", pp. 2598-2504, Jan. 2010.

The Physicians' Desk Reference ($60^{th}$ ed.), "Daytrana®", pp. 3283-3289, Jan. 2010.

The Physicians' Desk Reference ($60^{th}$ ed.), "Focalin®" XR, pp. 2472-2477, Jan. 2010.

The Physicians' Desk Reference ($60^{th}$ ed.), "Metadate CD®", pp. 3439-3443, Jan. 2010.

The Physicians' Desk Reference ($60^{th}$ ed.), "Ritalin® LA", pp. 3104-3106, Jan. 2010.

The Physicians' Desk Reference ($60^{th}$ ed.), "Tussionex®", pp. 3443-3444, Jan. 2010.

The Physicians' Desk Reference for Non-Prescription Drugs, Dietary Supplements, and Herbs ($29^{th}$ Ed.), "Delsym®", pp. 602-603, Jan. 2008.

Tris Phamra, Inc., Tris Pharma Announces US Patent Grant Covering Platform Technology (OralXR Press Release), retrieved from http://www.trispharma.com/news_New-US-Patent-Grant_Jan2012.php on Jul. 14, 2016, Jan. 2012, p. 1.

Tris Pharma, Inc., "Tris Pharma Presents Clinical Data for Dyanavel® XR (amphetamine) at the 2018 Neuroscience Education Institute (NEI) Congress", Nov. 12, 2018, retrieved on Nov. 15, 2018 from https://www.prnewswire.com/news-releases/tris-pharma-presents-clinical-data-for-dyanavel-xr-amphetamine-at-the-2018-neuroscience-education-institute-nei-congress-300748124.html.

Tris Pharma, Inc., LiquiXR™, retrieved from http://www.trispharma.com/technologies_liquiXR.php on Jul. 14, 2016, p. 1.

Tris Pharma, Inc., NextWave Pharmaceuticals Announces Launch of Nexiclon™ XR—First Extended-Release, Once-Daily Clonidine Oral Suspension and Tablet (Press Release), retrieved from http://www.trispharma.com/news_Nexiclon06Jan2011.php on Jul. 14, 2016. Jan. 2011, pp. 1-2.

Voskoboinikova, Drug Synthesis Methods and Manufacturing Technology, Modern Auxiliary Substances in Tablet Production: Use of High-Molecular-Weight Compounds for the Development of New Medicinal Forms and Optimization of Technological Processes, Pharmaceutical Chemistry Journal, 39(1):22-28 (Jan. 2005).

Wigal et al., "Efficacy and Safety of a Chewable Methylphenidate Extended-Release Tablet in Children with Attention-Deficit/Hyperactivity Disorder", Journal of Child and Adolescent Psychopharmacology, vol. 27(8):690-699, Oct. 2017.

Wigal et al., "Selection of the Optimal Dose Ratio for a Controlled-Deliveiy Formulation of Methylphenidate", J. Appl. Research., vol. 3:46-63, Oct. 2003.

European Search Report dated Jan. 20, 2012 and issued in European Patent Application No. 11192711.7, pp. 1-4.

Examination Report dated Feb. 1, 2012 issued in European Patent Application No. 11192711.7, pp. 1-5.

Applicant's Response to Feb. 1, 2012 Examination Report filed for European Patent Application No. 11192711.7, dated Mar. 29, 2012, pp. 1-6.

Intention to Grant dated May 23, 2012 issued in European Patent Application No. 11192711.7, pp. 1-78.

Examination Report dated Nov. 26, 2008 issued in European Patent Application No. 07753217.4, pp. 1-2.

Applicant's Response to Nov. 26, 2008 Examination Report (Rules 161 and 162) filed for European Patent Application No. 07753217.4, dated Dec. 17, 2008, pp. 1-16.

Examination Report (Rules 161 and 162) dated Nov. 22, 2010 issued in European Patent Application No. 07753217.4, pp. 1-4.

Applicant's Response to Nov. 22, 2010 Examination Report issued in European Patent Application No. 077532174, dated Mar. 25, 2011, pp. 1-21.

Intention to Grant dated Jul. 1, 2011 issued in European Patent Application No. 07753217.4, pp. 1-74.

Examination Report dated Sep. 24, 2013 issued in European Patent Application No. 11705137.5, pp. 1-2.

Applicant's Response to Sep. 24, 2013 Examination Report filed for European Patent Application No. 11705137.5, dated Mar. 10, 2014, pp. 1-17.

Observations by Third Parties dated Sep. 15, 2014 issued in European Patent Application No. 11705137.5, pp. 1-10.

Communication dated Sep. 22, 2014 issued in European Patent Application No. 11705137.5, pp. 1-36.

Applicant's Response to the Sep. 22, 2014 Communication filed for European Patent Application No. 11705137.5, dated Nov. 10, 2014, pp. 1-12.

Examination Report dated Jul. 21, 2015 issued in European Patent Application No. 11705137.5, pp. 1-5.

Applicant's Response to the Jul. 21, 2015 Examination Report filed for European Patent Application No. 11705137.5, dated Oct. 27, 2015, pp. 1-39.

English translation of an Office Action dated Aug. 21, 2012 issued in Japanese Patent Application No. 2009-500494, pp. 1-9.

English translation of an Office Action dated Oct. 8, 2013 issued in Japanese Patent Application No. 2009-500494, pp. 1-2.

Correspondence from the agent regarding an Office Action dated Oct. 20, 2010 issued in Israeli Patent Application No. 194042, pp. 1-8.

Applicant's Response and English translation thereof to the Oct. 20, 2010 Office Action issued in Israeli Patent Application No. 194042, dated Apr. 5, 2011, pp. 1-7.

Office Action dated Mar. 18, 2013 issued Canadian Patent Application No. 2,645,855, pp. 1-3.

(56) References Cited

OTHER PUBLICATIONS

Applicant's Response to Mar. 18, 2013 Office Action filed for Canadian Patent Application No. 2,645,855, dated Sep. 18, 2013, pp. 1-54.
Office Action dated Dec. 9, 2013 issued Canadian Patent Application No. 2,645,855, pp. 1-12.
Response to Dec. 9, 2013 Office Action filed for Canadian Patent Application No. 2,645,855, dated Jun. 9, 2014, pp. 1-41.
Examination Report dated Mar. 11, 2014 issued in Indian Patent Application No. 8703/DELNP/2008, pp. 1-6.
Response to Mar. 11, 2014 Examination Report filed for Indian Patent Application No. 8703/DELNP/2008, dated Dec. 30, 2014, pp. 1-14.
First Examiner's Report dated Nov. 28, 2011 issued in Australian Patent Application No. 2007227569, pp. 1-3.
Applicant's Response to the Nov. 28, 2011 First Examiner's Report filed for Australian Patent Application No. 2007227569, dated Aug. 5, 2013, pp. 1-30.
Office Action and English translation thereof dated Jan. 28, 2011 issued in Russian Federation Patent Application No. 2008140944, pp. 1-9.
English translation of a First Office Action dated Feb. 6, 2013 issued in Chinese Patent Application No. 201110371263.X, pp. 1-9.
English translation of a Second Office Action dated Oct. 24, 2013 issued in Chinese Patent Application No. 201110371263.X, pp. 1-9.
English translation of a First Office Action dated Apr. 30, 2010 issued in Chinese Patent Application No. 200780009208.8, pp. 1-4.
English translation of a Notification of Grounds of Refusal dated Aug. 25, 2013 issued in Korean Patent Application No. 10-2008-7024357, pp. 1-8.
English translation of a Notification of Grounds of Refusal dated Apr. 4, 2014 issued in Korean Patent Application No. 10-2008-7024357, pp. 1-6.
Amendment filed for Australian Patent Application No. 2011359405, dated Nov. 25, 2015, pp. 1-30.
Examination Report dated May 19, 2016 issued on Australian Patent Application No. 2011359405.
Office Action dated Nov. 12, 2009 issued in U.S. Appl. No. 11/724,966, pp. 1-24.
Applicant's Response to the Office Action dated Nov. 12, 2009 issued in U.S. Appl. No. 11/724,966, pp. 1-26.
Interview Summary dated Mar. 17, 2010 issued in U.S. Appl. No. 11/724,966, pp. 1-3.
Non-Final Office Action dated Aug. 1, 2014 issued on U.S. Appl. No. 14/300,580, pp. 1-7.
Response to Aug. 1, 2014 Office Action filed for U.S. Appl. No. 14/300,580, dated Oct. 17, 2014, pp. 1-14.
Notice of Allowance dated Feb. 11, 2015 issued on U.S. Appl. No. 14/300,580, pp. 1-7.
Non-Final Office Action dated Apr. 1, 2015 issued on U.S. Appl. No. 14/624,998, pp. 1-10.
Response to Apr. 1, 2015 Office Action filed for U.S. Appl. No. 14/624,998, dated Jun. 26, 2015, pp. 1-14.
Notice of Allowance dated Sep. 3, 2015 issued on U.S. Appl. No. 14/624,998, pp. 1-8.
Non-Final Office Action dated Nov. 10, 2015 issued on U.S. Appl. No. 14/872,226, pp. 1-6.
Response to Nov. 10, 2015 Office Action filed for U.S. Appl. No. 14/872,226, dated Nov. 24, 2015, pp. 1-8.
Notice of Allowance dated Jan. 12, 2016 issued on U.S. Appl. No. 14/872,226, pp. 1-5.
Non-Final Office Action dated Aug. 10, 2016 issued on U.S. Appl. No. 15/009,468, pp. 1-7.
Non-Final Office Action dated Sep. 9, 2016 issued on U.S. Appl. No. 15/200,625, pp. 1-8.
Response to Sep. 9, 2016 Office Action issued on U.S. Appl. No. 15/200,625, dated Sep. 14, 2016, pp. 1-11.
Communication Pursuant to Rules 161(1) & 162 EPC, dated Apr. 21, 2015, issued on counterpart European Patent Application No. 13752782.6, pp. 1-6.
Applicant's Response to Apr. 21, 2015 Communication issued on European Patent Application No. 13752782.6, dated Oct. 23, 2015, pp. 1-24.
Examination Report issued on Australian Patent Application No. 2013302657, dated Sep. 8, 2017.
Office Action issued on Israeli Patent Application No. 236847, dated Aug. 10, 2017 and Response.
Non-final Office Action, dated Aug. 23, 2017, issued on U.S. Appl. No. 15/258,700, and Response.
Final Office Action, dated May 16, 2018, issued on U.S. Appl. No. 15/258,700, and Response.
Non-final Office Action, dated Apr. 21, 2017, issued on U.S. Appl. No. 15/258,695, and Response.
Final Office Action, dated Dec. 22, 2017, issued on U.S. Appl. No. 15/258,695, and Response.
Non-final Office Action, dated Jun. 28, 2018, issued on U.S. Appl. No. 15/258,695, and Response.
International Search Report and Written Opinion dated Oct. 1, 2007 and issued in International Patent Application No. PCT/US2007/006572, pp. 1-4.
International Search Report and Written Opinion dated Feb. 22, 2012 and issued in International Patent Application No. PCT/US2011/024873, pp. 1-4.
International Search Report and Written Opinion dated Oct. 21, 2013 and issued in International Patent Application No. PCT/US2013/054930, pp. 1-4.
Mehta, U.S. Appl. No. 15/244,430 for "Orally Effective Extended Release :Powder and Aqueous Suspension Product", filed Aug. 23, 2016.
Mehta, U.S. Appl. No. 15/215,276, for "Orally Effective Extended Release :Powder and Aqueous Suspension Product", filed Jul. 20, 2016.
Kathala, U.S. Appl. No. 15/200,625 for "Methylphenidate Extended Release Chewable Tablet", filed Jul. 1, 2016.
English abstract for Japanese Patent Publication No. 02-172912 dated Jul. 4, 1990, p. 1.
English abstract for Japanese Patent Publication No. 5-279247 dated Dec. 26, 1993, pp. 1-3.
English abstract for Japanese Patent Publication No. 2005-306778 dated Nov. 4, 2005, pp. 1-3.
English abstract for Japanese Patent Publication No. 2003-528910 dated Sep. 30, 2003, p. 1.
Set of claims filed on Mar. 18, 2014 in U.S. Pat. Appl. No. 13/844,555, pp. 1-3.
Set of claims filed on May 2, 2014 in U.S. Appl. No. 13/844,537, pp. 1-5.
Set of claims filed on Mar. 18, 2014 in U.S. Appl. No. 13/844,510, pp. 1-3.
Mehta et al., U.S. Appl. No. 14/679,438, filed Apr. 6, 2015.
Nelson et al., U.S. Appl. No. 14/677,073, filed Apr. 2, 2015.
Nelson et al., U.S. Appl. No. 14/830,040, filed Aug. 19, 2015.
Nelson et al., U.S. Appl. No. 14/829,952, filed Aug. 19, 2015.
Nelson et al., U.S. Appl. No. 14/829,971, filed Aug. 19, 2015.
Mehta et al., U.S. Appl. No. 15/200,617, filed Jul. 1, 2016.
Mehta et al., U.S. Appl. No. 15/200,786, filed Jul. 1, 2016.
Mehta et al., U.S. Appl. No. 14/679,427, filed Apr. 6, 2015.
Mehta et al., U.S. Appl. No. 15/200,748, filed Jul. 1, 2016.
Report on the Filing or Determination of an Action Regarding a Patent or Trademark dated Oct. 15, 2014, p. 1.
Complaint by Tris Pharma, Inc. against Actavis Laboratories FL, Inc. et al., C.A. No. 14-1309-GMS, dated Oct. 15, 2014, pp. 1-17.
Defendant Actavis Laboratories FL, Inc.'s Answer, Defenses, and Counterclaims, C.A. No. 14-1309-GMS, dated Dec. 5, 2014, pp. 1-24.
Answer to Actavis Laboratories FL, Inc.'s Counterclaims, C.A. No. 14-1309-GMS, dated Dec. 29, 2014, pp. 1-7.
First Amended Complaint, C.A. No. 14-1309-GMS, dated May 22, 2015, pp. 1-22.
Defendant Actavis Laboratories FL, Inc.'s Initial Invalidity Contentions, C.A. No. 14-1309-GMS, dated May 27, 2015, pp. 1-152.
Defendants Par Pharmaceutical, Inc.'s and Par Pharmaceutical Companies, Inc.'s Initial Invalidity Contentions, C.A. No. 14-1309-GMS, dated Jun. 10, 2015, pp. 1-199.

(56) References Cited

OTHER PUBLICATIONS

Defendants Par Pharmaceutical, Inc.'s and Par Pharmaceutical Companies, Inc.'s Answer to First Amended Complaint and Counterclaims, C.A. No. 14-1309-GMS, dated Jun. 12, 2015, pp. 1-49.
Defendant's Par Pharmaceutical, Inc.'s and Par Pharmaceutical Companies, Inc.'s Answer to Second Amended Complaint and Counterclaims, C.A. No. 14-1309-GMS, dated Aug. 24, 2015, pp. 1-57.
Joint Claim Construction Statement and Chart, C.A. No. 14-1309-GMS, dated Sep. 30, 2015, pp. 1-13.
Defendant's Opening Claim Construction Brief, C.A. No. 14-1309-GMS, dated Oct. 30, 2015, pp. 1-15.
Supplemental Joint Claim Construction Brief, C.A. No. 14-1309-GMS, dated Oct. 30, 2015, pp. 1-2.
Tris's Opening Claim Construction Brief, C.A. No. 14-1309-GMS, dated Oct. 30, 2015, pp. 1-21.
Defendant Actavis Laboratories FL, Inc.'s Amended Initial Invalidity Contentions, C.A. No. 14-1309-GMS, dated Jan. 22, 2016, pp. 1-198.
Defendant Actavis Laboratories FL, Inc.'s Final Invalidity Contentions, C.A. No. 14-1309-GMS, dated Feb. 8, 2016, pp. 1-203.
Exhibit C: Materials Considered in Expert Report by Richard Christian Moreton, C.A. No. 14-1309-GMS, dated May 3, 2016, pp. 1-3.
Exhibit B: Materials Considered in Expert Report by Jud Staller, M.D., C.A. No. 14-1309-GMS, dated May 3, 2016, pp. 1-2.
Exhibit B: Materials Considered in Expert Report by Arthur B. Straughn, Pharm.D., C.A. No. 14-1309-GMS, dated May 3, 2016, pp. 1-2.
List of Exhibits in Responding Expert Report by Dr. C. Lindsay DeVane, C.A. No. 14-1309-GMS, dated Jun. 21, 2016, pp. 1-5.
List of Exhibits in Responding Expert Report by James John McGough, M.D., M.S., C.A, No. 14-1309-GMS, dated Jun. 21, 2016, pp. 1-5.
List of Exhibits in Responding Expert Report by Dr. Irwin Jacobs, C.A. No. 14-1309-GMS, dated Jun. 21, 2016, pp. 1-6.
*Tris Pharma, Inc.* v. *Actavis Laboratories FL, Inc.*, Tris's Proposed Post-Trial Findings of Fact and Conclusions of Law, C.A. No. 14-1309-GMS, Mar. 24, 2017.
*Tris Pharma, Inc.* v. *Actavis Laboratories FL, Inc.*, Defendant's Post-Trial Findings of Fact and Conclusions of Law, C.A. No. 14-1309-GMS, Mar. 24, 2017.
*Tris Pharma, Inc.* v. *Actavis Laboratories FL, Inc.*, Memorandum and Opinion, C.A, No. 14-1309-GMS, Sep. 5, 2017.
*Tris Pharma, Inc.* v. *Actavis Laboratories FL, Inc.*, Appeal Brief for Plaintiff-Appellant, C.A, No. 14-1309-GMS, Dec. 4, 2017.
*Tris Pharma, Inc.* vs. *Actavis Laboratories FL*, Inc., C.A. Nos. 14-13 09-GMS, 15-969-GMS, and 15-393-GMS, "Response Brief for the Defendant-Appellee", dated Feb. 15, 2018.
*Tris Pharma, Inc.* v. *Actavis Laboratories FL, Inc.*, Reply Brief for Plaintiff-Appellant, C.A, No. 14-1309-GMS, Mar. 15, 2018.
Complaint by Tris Pharma, Inc. against Par Pharmaceutical, Inc et al., C.A. No. 15-0068-GMS, dated Jan. 21, 2015, pp. 1-21.
Defendants Par Pharmaceutical, Inc.'s and Par Pharmaceutical Companies, Inc.'s Answer to Complaint and Counterclaims, C.A. No. 15-0068-GMS, dated Feb. 12, 2015, pp. 1-38.
Answer to Par Pharmaceutical, Inc.'s and Par Pharmaceutical Companies, Inc.'s Counterclaims, C.A, No. 15-0068-GMS, dated Feb. 26, 2015, pp. 1-10.
Complaint by Tris Pharma, Inc. against Actavis Laboratories FL, Inc., et al., C.A. No. 15-393-GMS, dated May 15, 2015, pp. 1-10.
Defendant Actavis Laboratories FL, Inc.'s Answer, Affirmative Defenses, and Counterclaims, C.A, No. 15-393-GMS, dated Jun. 12, 2015, pp. 1-15.
Complaint by Tris Pharma, Inc. against Actavis Elizabeth LLC and Actavis, Inc., C.A, No. 16-603-GMS, dated Jul. 12, 2016.
Defendants Actavis Elizabeth LLC and Actavis Inc.'s Answer, Defenses, and Counterclaims, C.A, No. 16-603-GMS, dated Sep. 2, 2016.
TRIS Answer to Defendants Actavis and Actavis Elizabeth LLC's Counterclaims, *Tris Pharma, Inc.,* v. *Actavis Elizabeth LLC*, C.A. No. 16-603-GMS In the United States District Court for the District of Delaware, Document 13, Filed Sep. 26, 2016, pp. 1-15.
First Amended Complaint, *Tris Pharma, Inc.,* v. *Actavis Elizabeth LLC*, C.A. No. 16-603-GMS In the United States District Court for the District of Delaware, Document 32, Filed Apr. 25, 2017, pp. 1-11.
Defendants Actavis and Actavis Elizabeth LLC's Answer and Defenses, and Actavis Elizabeth LLC's Counterclaims to Plaintiff's First Amended Complaint, *Tris Pharma, Inc.,* v. *Actavis Elizabeth LLC*, C.A. No. 16-603-GMS In the United States District Court for the District of Delaware, Document 35, Filed Apr. 25, 2017, pp. 1-15.
TRIS' Answer to Defendant Actavis Elizabeth's Counterclaims, *Tris Pharma, Inc.,* v. *Actavis Elizabeth LLC*, C.A. No. 16-603-GMS In the United States District Court for the District of Delaware, Document 39, Filed May 9, 2017, pp. 1-8.
Defendant Actavis Elizabeth LLC's Initial Invalidity Contentions, *Tris Pharma, Inc.,* v. *Actavis Elizabeth LLC*, C.A. No. 16-603-GMS In the United States District Court for the District of Delaware, pp. 1-111, May 17, 2017.
*Tris Pharma, Inc.* vs. *Actavis Elizabeth LLC*, C.A. No. 16-603-GMS, "Order Construing the terms of U.S. Pat. No. 9,545,399", dated Feb. 20, 2018.
Second Amended Complaint for Patent Infringement against Actavis Elizabeth LLC—filed by Tris Pharma Inc., C.A. No. 16-603-GMS, entered Mar. 20, 2018.
Answer to Amended Complaint, re: 120 Amended Complaint Affirmative Defenses and, Counterclaim against Tris Pharma Inc. by Actavis Elizabeth LLC., C.A. No. 16-603-GMS, entered Mar. 28, 2018.
Notice of Paragraph IV Certification from Actavis, dated Sep. 3, 2014 and "Detailed Factual and Legal Bases for Actavis's Paragraph IV Certification that U.S. Pat. Nos. 8,062,667; U.S. Pat. No. 8,287,903; U.S. Pat. No. 8,465,765; U.S. Pat. No. 8,563,033; and U.S. Pat. No. 8,778,390 are Invalid, Unenforceable, and/or Not Infringed", pp. 1-23.
Notice of Paragraph IV Certification from Par Pharmaceuticals, dated Dec. 22, 2014, and "Detailed Statement of the Factual and Legal Bases for Par's Opinion that U.S. Pat. Nos. 8,062,667; U.S. Pat. No. 8,287,903; U.S. Pat. No. 8,465,765; U.S. Pat. No. 8,563,033; and U.S. Pat. No. 8,778,390 are Invalid, Unenforceable, and/or Not Infringed", pp. 1-69.
Notice of Paragraph IV Certification from Par Pharmaceuticals, dated Apr. 2, 2015, and "Detailed Statement of the Factual and Legal Bases for Par's Opinion that U.S. Pat. No. 8,956,649 is Invalid, Unenforceable, and/or Will Not Be Infringed", pp. 1-28.
Notice of Paragraph IV Certification from Par Pharmaceuticals, dated Jun. 17, 2015, and "Detailed Statement of the Factual and Legal Bases for Par's Opinion that U.S. Pat. No. 9,040,083 is Invalid, Unenforceable, and/or Will Not Be Infringed", pp. 1-24.
Notice of Paragraph IV Certification from Actavis, dated Sep. 9, 2015, and "Detailed Factual and Legal Bases for Actavis's Paragraph IV Certification that U.S. Pat. No. 9,040,083 Is Invalid, Unenforceable and/or Not Infringed", pp. 1-19, dated Sep. 9, 2015.
Notification of Certification for U.S. Pat. Nos. 8,202,537; U.S. Pat. No. 8,287,903; U.S. Pat. No. 8,999,386; and U.S. Pat. No. 9,295,642 Pursuant to § 505(j)(2)(B)(iv) of the Federal Food, Drug, and Cosmetic Act, pp. 1-22, dated Jun. 2, 2016.
Notification of Certification for U.S. Pat. No. 9,545,399 Pursuant to § 505(j)(2)(B)(iv) of the Federal Food, Drug, and Cosmetic Act with Actavis' Detailed Factual and Legal Basis for Its Paragraph IV Certification that U.S. Pat. No. 9,545,399 Is Invalid, Unenforceable and/or Not Infringed by the Methylphenidate Hydrochloride Products Described in Actavis' ANDA No. 209134, dated Mar. 10, 2017.
Childress et al., Open-Label Dose Optimization Study of Dyanavel XR (Amphetamine Extended-Release Oral Suspension) in Children with Attention-Deficit/Hyperactivity Disorder, 2019 American Professional Society for ADHD and Related Disorders Annual Meeting, Washington DC, Jan. 18, 2019.
Herman et al., Single-Dose Pharmacokinetics of Dyanavel XR (Amphetamine Extended-Release Oral Suspension in Children Aged

(56) References Cited

OTHER PUBLICATIONS 4-5 years with Attention-Deficit/Hyperactivity Disorder, 2019 American Professional Society for ADHD and Related Disorders Annual Meeting, Washington DC, Jan. 18, 2019.
Herman et al., A Novel, Modified-Release Drug Delivery Technology Containing Amphetamine Ion-Exchange Complexes, 2019 American Professional Society for ADHD and Related Disorders Annual Meeting, Washington DC, Jan. 18, 2019.
Childress et al., Efficacy and Safety of Dyanavel XR (Amphetamine Extended-Release Oral Suspension) in the Treatment of Children with ADHD, 2019 Nevada Psychiatric Association Annual Pharmacology Update, Las Vegas, NV, Feb. 16, 2019.
Herman et al., Early Onset Efficacy and Safety Pilot Study of Dyanavel XR (Amphetamine Extended-Release Oral Suspension) in the Treatment of Children with ADHD, 2019 Nevada Psychiatric Association Annual Pharmacology Update, Las Vegas, NV, Feb. 16, 2019.
Herman et al., Pharmacokinetics of Amphetamine Extended Release Oral Suspension (AMPH EROS) in Adolescents Interpolated from Children and Adults Using Population Analysis, 2019 American Psychiatric Association Annual Meeting, Apr. 20, 2019.
Pardo et al., Single-Dose Pharmacokinetics of Dyanavel XR (Amphetamine Extended-Release Oral Suspension) in Children Aged 6-12 Years Old with Attention-Deficit/Hyperactivity Disorder, 2019 American College of Child and Adolescent Psychiatry (65th Annual Meeting).
Herman et al., Single-Dose Pharmacokinetics of Amphetamine Extended-Release (Dyanavel® XR) Tablet Compared with Amphetamine Extended-Release (Dyanavel® XR) Oral Suspension (AMPH EROS), Psych Congress 2019.
Herman et al., Palatability Assessment of a New Amphetamine Extended-Release Tablet Formulation, 2020 APSARD, Jan. 15-17, 2020.
Herman et al., Comparative Bioavailability of Amphetamine Extended Extended-Release Oral Suspension (AMPH EROS, Dyanavel XR) and Extended-Release Mixed Amphetamine Salts (ER MAS), 2020 APSARD, Jan. 15-17, 2020.
Cutler et al., Randomized, Double Blind, Placebo Controlled, Fixed Dose Study to Evaluate the Efficacy and Safety of the Amphetamine Extended Release Tablet in Adults with Attention Deficit/Hyperactivity Disorder, 2021 APSARD, Jan. 13-15, 2021.
Childress et al., Early-Onset Efficacy and Safety Pilot Study of Amphetamine Extended-Release Oral Suspension in the Treatment of Children with Attention-Deficit/Hyperactivity Disorder, Journal of Child and Adolescent Psychopharmacology, vol. 29(1):1-7, Dec. 2019.
Herman et al., Single-Dose Pharmacokinetics of Amphetamine Extended-Release Oral Suspension in Healthy Adults, Journal of Attention Disorders, Apr. 2019.
Pardo et al., A Single-Dose, Comparative Bioavailability Study Comparing Amphetamine Extended-Release Oral Suspension with Extended-Release Mixed Amphetamine Salts Capsules, 2020.
Pardo et al., Single-dose pharmacokinetics of amphetamine extended-release tablets compared with amphetamine extended-release oral suspension, CNS Spectrums, vol. 25(6):774-781, Dec. 2020.
Herman et al., A Novel, Modified-Release Drug Delivery Technology Containing Amphetamine-Ion Exchange Complexes, Abstract, Cambridge University Press, vol. 24(1):220, Mar. 2019.
Cutler et al., Randomized, Double-Blind, Placebo-Controlled, Fixed-Dose Study to Evaluate the Efficacy and Safety of the Amphetamine Extended-Release Tablet in Adults with Attendon-Deficit/Hyperactivity Disorder, 2021 APSARD, Jan. 15-17, 2021.
Everitt et al., Palatability Assessment of a New Amphetamine Extended Release Tablet Formulation, 2020 AACAP Annual Meeting, Oct. 23, 2020.
BASF Pharma Solutions: Excipients by Trademark, Kollicoat®, BASF website, www.pharma-solutions.basf.com. pp. 1-3 (Dec. 2, 2004).
BASF ExAct, Excipients & Actives for Pharma, No. 1, BASF website, pp. 1-8 http://www2.basf.us/Pharma/pdf/ExAct_01.pdf (Nov. 1998).
BASF, Pharmasolutions, Men/PD 130, Correlation of Drug Prevention Through Isolated Films and Coated Dosage forms Based on Kollicoat 30SR, 1999.
BASF, Development of High Functionality Excipients for Immunity and Sustained Release Dos Forms (Sep. 20, 2004).
Duolite AP143/1093 Pharmaceutical Grade Anion Exchange Resin, Product Data Sheet, pp. 1-3 (Nov. 2004).
Guide-Choosing the Right Functional Polymer, pp. 1, www.F:/HeathcareWebsite/guide.htm (Feb. 9, 2006).
Ion Exchange Resins, GB/US (Jan. 2004).
Kollicoat SR30D, Technical Information, Bulletin, MEV96 (Jun. 1999).
Kollicoat SR30D, Technical Information, ME36(e), pp. 1-14 (Jun. 1999).
Kollicoat® SR 30 D, Tackiness of Films as a Function of Type and concentration of Plasticizer, BASF-Expertise in Health and Nutrition (Dec. 2007).
Kolter, Influence of plasticizers on the Physico-Chemical Properties of Kollicoat® SR 30 D-Films, BASF Aktiengesellschaft (Spring/Summer 2004).
Kolter, Kollicoat® SR 30 D A New Sustained Release Excipient, BASF AG, p. 1 (Nov. 1999).
Tablet Disintegrate, Ion Exchange Resins-Healthcare, Rohm Haas, pp. 1, www.F:/Heathcare Website/deliquescence.htm (Feb. 9, 2006).
Dyanavel® Chemistry Reviews, Application No. 208147Orig1s000, Center for Drug Evaluation and Research, dated Aug. 18, 2015.
Dyanavel® Summary Reviews, Application No. 208147Orig1s000, Center for Drug Evaluation and Research, dated Dec. 19, 2014 (completed Oct. 19, 2015).
Lin, Comparative bioavailability of d-pseudoephedrine from a conventional d-pseudoephedrine sulfate tablet and from a repeat action tablet, Journal of International Medical Research 10(2): 126-128 (1982).
Remington, "The Science and Practice of Pharmacy ($20^{th}$ Ed)", pp. 986-994, Jan. 2000.
Childress et al., The use of methylphenidate hydrochloride extended-release oral suspension for the treatment of ADHD, Expert Rev Neurother, vol. 13(9), Sep. 2013, pp. 979-988.
Childress et al., The single-dose pharmacokinetics of NWP06, a novel extended-release methylphenidate oral suspension, Postgrad Med, vol. 122(5), Sep. 2010, pp. 35-41.
Pardo et al., "Single-dose pharmacokinetics of amphetamine extended-release tablets compared with amphetamine extended-release oral suspension," CNS Spectrums, pp. 1-8, Sep. 2019.
FDA Drug Approval Package for Dyanavel: Amphetamine (Amphetamine), Company Tris Pharma, Application No. 208147 Orig. 1, Approval Date Oct. 19, 2025, https://www.accessdata.fda.gov/drugsatfda_docs/nda/2015/208147Orig1DyanavelTOC.cfm, accessed May 20, 2021.
Dyanavel® Medical Reviews, Application No. 208147Orig1s000, Center for Drug Evaluation and Research, dated Dec. 19, 2014 (completed Oct. 19, 2015).
NDA Approval Letter from the Department of Health and Human Services, dated Dec. 18, 2014.
Dyanavel® Other Reviews, Application No. 208147Orig1s000, Center for Drug Evaluation and Research, dated Oct. 14, 2015.
Dyanavel® Pharmacology Reviews, Application No. 208147Orig1s000, Center for Drug Evaluation and Research, dated Dec. 18, 2015 (completed Dec. 19, 2014).
Dyanavel® NPA Tablet Approval, FDA, NPA 210526, Nov. 4, 2021.
Dyanavel XR® Approved Labeling, FDA, Revised Nov. 2021.
Office Action dated Oct. 22, 2019 issued on Brazilian Patent Application No. PI0709606-2, pp. 1-5.
Applicant's Response to Interview Summary dated Mar. 17, 2010 issued in U.S. Appl. No. 11/724,966, pp. 1-9.
Office Action dated Jun. 23, 2010 issued in U.S. Appl. No. 11/724,966, pp. 1-14.
Applicant's Response to the Office Action dated Jun. 23, 2010 issued in U.S. Appl. No. 11/724,966, pp. 1-79.

(56) References Cited

OTHER PUBLICATIONS

Office Action dated Nov. 26, 2010 issued in U.S. Appl. No. 11/724,966, pp. 1-15.
Applicant's Response to the Office Action dated Nov. 26, 2010 issued in U.S. Appl. No. 11/724,966, pp. 1-91.
Rule 131 Declaration executed by Drs. Mehta and Tu filed Sep. 23, 2010 in U.S. Appl. No. 11/724,966, pp. 1-54.
Rule 132 Declaration executed by Dr. Tu filed May 25, 2011 in U.S. Appl. No. 11/724,966, pp. 1-35.
Rule 132 Declaration executed by Dr. Kibbe filed May 25, 2011 in U.S. Appl. No. 11/724,966, pp. 1-29.
Notice of Allowance dated Aug. 19, 2011 issued in U.S. Appl. No. 11/724,966, pp. 1-10.
Office Action dated Dec. 9, 2011 issued in U.S. Appl. No. 12/722,857, pp. 1-18.
Applicant's Response to the Office Action dated Dec. 9, 2011 issued in U.S. Appl. No. 12/722,857, pp. 1-19.
Notice of Allowance dated Aug. 30, 2012 issued in U.S. Appl. No. 12/722,857, pp. 1-8.
Office Action dated Dec. 9, 2011 issued in U.S. Appl. No. 13/244,748, pp. 1-65.
Applicant's Response to the Office Action dated Dec. 9, 2011 issued in U.S. Appl. No. 13/244,748, pp. 1-38.
Notice of Allowance dated Apr. 27, 2012 issued in U.S. Appl. No. 13/244,748, pp. 1-16.
Office Action dated Jan. 18, 2013 issued in U.S. Appl. No. 13/666,424, pp. 1-27.
Applicant's Response to the Office Action dated Jan. 18, 2013 issued in U.S. Appl. No. 13/666,424, pp. 1-15.
Notice of Allowance dated May 17, 2013 issued in U.S. Appl. No. 13/666,424, pp. 1-10.
Office Action dated Mar. 21, 2013 issued in U.S. Appl. No. 13/746,654, pp. 1-22.
Applicant's Response to the Office Action dated Mar. 21, 2013 issued in U.S. Appl. No. 13/746,654, pp. 1-139.
Notice of Allowance dated Jul. 31, 2013 issued in U.S. Appl. No. 13/746,654, pp. 1-10.
Office Action dated Nov. 21, 2013 issued in U.S. Appl. No. 14/044,105, pp. 1-15.
Applicant's Response to the Office Action dated Nov. 21, 2013 issued in U.S. Appl. No. 14/044,105, pp. 1-15.
Applicant Initiated Interview Summary dated May 13, 2014 issued in U.S. Appl. No. 14/044,105, p. 1.
Notice of Allowance dated May 13, 2014 issued in U.S. Appl. No. 14/044,105, pp. 1-10.
Office Action dated Dec. 5, 2013 issued in U.S. Appl. No. 14/065,842, pp. 1-18.
Applicant's Response to the Office Action dated Dec. 5, 2013 issued in U.S. Appl. No. 14/065,842, pp. 1-10.
Notice of Allowance dated Apr. 9, 2014 issued in U.S. Appl. No. 14/065,842, pp. 1-10.
Office Action dated Feb. 26, 2014 issued in U.S. Appl. No. 14/155,410, pp. 1-16.
Applicant's Response to the Office Action dated Feb. 26, 2014 issued in U.S. Appl. No. 14/155,410, pp. 1-10.
Notice of Allowance issued on U.S. Appl. No. 14/155,410, dated Jul. 21, 2014, pp. 1-12.
Office Action issued on U.S. Appl. No. 14/508,613, dated Mar. 29, 2016, and Response.
Notice of Allowance issued on U.S. Appl. No. 14/508,613, dated Dec. 23, 2016.
Office Action issued on U.S. Appl. No. 15/3 83,474, dated Jul. 14, 2017 and Response.
Final Office Action issued on U.S. Appl. No. 15/383,474, dated Feb. 21, 2018 and Response.
Notice of Allowance issued on U.S. Appl. No. 15/383,474, dated Nov. 27, 2018.
Notice of Allowance issued on U.S. Appl. No. 16/241,287, dated Apr. 22, 2020.
Notice of Allowance issued on U.S. Appl. No. 16/241,287, dated Apr. 14, 2020.
Rule 312 Amendment filed on U.S. Appl. No. 16/241,287, dated Mar. 10, 2020 and Response dated Mar. 23, 2020.
Notice of Allowance issued on U.S. Appl. No. 16/241,287, dated Jan. 28, 2020.
Office Action dated Jul. 11, 2019 issued on U.S. Appl. No. 16/241,287, and Response dated Dec. 11, 2019 with Declaration of Dr. Yu-Hsing Tu, dated Jun. 1, 2012.
Office Action issued on U.S. Appl. No. 16/719,121, dated Jun. 1, 2020, and Response dated Sep. 1, 2020.
Office Action issued on U.S. Patent Application No. 14/735,526, dated Aug. 27, 2015 and Response.
Notice of Allowance issued on U.S. Appl. No. 14/735,526, dated Oct. 13, 2015.
Notice of Allowance issued on U.S. Appl. No. 15/047,388, dated Dec. 19, 2016.
Final Office Action issued on U.S. Appl. No. 15/200,617, dated Aug. 21, 2017.
Office Action issued on U.S. Appl. No. 15/200,617, dated Sep. 22, 2016 and Response.
Office Action issued on U.S. Appl. No. 15/200,748, dated Sep. 22, 2016 and Response.
Notice of Allowance issued on U.S. Appl. No. 15/200,748, dated Apr. 11, 2017.
Corrected Notice of Allowance issued on U.S. Appl. No. 15/200,748, dated May 3, 2017.
Office Action issued on U.S. Appl. No. 15/200,786, dated Sep. 22, 2016 and Response.
Notice of Allowance issued on U.S. Appl. No. 15/200,786, dated Apr. 10, 2017.
Corrected Notice of Allowance issued on U.S. Appl. No. 15/200,786, dated May 3, 2017.
Office Action issued on U.S. Appl. No. 15/619,637, dated Jul. 11, 2017.
Final Office Action issued on U.S. Appl. No. 15/619,637, dated Nov. 17, 2017 and Response.
Notice of Allowance issued on U.S. Appl. No. 15/619,637, dated Aug. 15, 2018.
Corrected Notice of Allowance issued on U.S. Appl. No. 15/619,637, dated Sep. 6, 2018.
Communication pursuant to Article 94(3) EPC issued on European Patent Application No. 11705137.5, dated Aug. 19, 2016, and Response.
Intent to Grant issued on European Patent Application No. 11705137.5, dated Oct. 12, 2018.
Examination Report dated Feb. 12, 2018, issued on Australian Patent Application No. 2017202955.
Final Office Action issued on U.S. Appl. No. 15/706,234, dated May 17, 2018.
Office Action issued on U.S. Appl. No. 15/706,234, dated Oct. 31, 2017 and Response.
Final Office Action issued on U.S. Appl. No. 16/249,415, dated Sep. 19, 2019.
Office Action issued on U.S. Appl. No. 16/249,415, dated Feb. 25, 2019, and Response dated Aug. 21, 2019.
Office Action issued on related Israeli Patent Application No. 227734, dated Nov. 1, 2016.
Office Action dated Dec. 23, 2011 issued in U.S. Appl. No. 13/244,706, pp. 1-27.
Applicant's Response Office Action dated Dec. 23, 2011 issued in U.S. Appl. No. 13/244,706, pp. 1-127.
Office Action dated Jun. 15, 2012 issued in U.S. Appl. No. 13/244,706, pp. 1-19.
Applicant's Response to the Office Action dated Jun. 15, 2012 issued in U.S. Appl. No. 13/244,706, pp. 1-18.
Notice of Allowance dated Aug. 13, 2012 issued in U.S. Appl. No. 13/244,706, pp. 1-11.
Office Action dated Nov. 9, 2012 issued in U.S. Appl. No. 13/611,183, pp. 1-10.
Applicant's Response to the Office Action dated Nov. 9, 2012 issued in U.S. Appl. No. 13/611,183, dated Jan. 10, 2013, pp. 1-26.

(56) References Cited

OTHER PUBLICATIONS

Answer to the Defendant Teva's Counterclaims, C.A. No. 2:20-cv-05212-KM-JBC, dated Jul. 20, 2020.
Notice of Allowance dated May 10, 2013 issued in U.S. Appl. No. 13/611,183, pp. 1-13.
Notice of Allowance dated Aug. 2, 2013 issued in U.S. Appl. No. 13/905,808, pp. 1-16.
Office Action dated Nov. 21, 2013 issued in U.S. Appl. No. 14/016,384, pp. 1-12.
Applicant's Response to the Office Action dated Nov. 21, 2013 issued in U.S. Appl. No. 14/016,384, pp. 1-15.
Notice of Allowance issued on U.S. Appl. No. 14/016,384, dated May 9, 2014, pp. 1-8.
Notice of Allowance issued on U.S. Appl. No. 14/299,421, dated Dec. 19, 2014.
Applicant-Initiated Interview Summary filed for U.S. Appl. No. 14/554,123, dated Feb. 6, 2015.
Office Action issued on U.S. Appl. No. 14/554,123, dated Jan. 7, 2015 and Response.
Notice of Allowance issued on U.S. Appl. No. 14/554,123, dated Apr. 15, 2015.
Corrected Notice of Allowance issued on U.S. Appl. No. 14/554,123, dated Apr. 20, 2015,.
Office Action issued on U.S. Appl. No. 14/657,151, dated Apr. 24, 2015 and Response.
Final Office Action issued on U.S. Appl. No. 14/657,151, dated Sep. 24, 2015 and Response.
Advisory Action and Examiner-Initiated Interview Summary issued on U.S. Appl. No. 14/657,151, dated Dec. 15, 2015,.
Office Action issued on U.S. Appl. No. 15/215,276, dated Sep. 25, 2017.
Office Action issued on U.S. Patent Application No. 15/244,43 0, dated Sep. 22, 2017.
Office Action issued on Canadian Patent Application No. 2,880,456, dated Jul. 9, 2019.
Office Action issued on Canadian Patent Application No. 2,880,456, dated Apr. 9, 2020.
Response to Aug. 10, 2016 Office Action issued on U.S. Appl. No. 15/009,468, pp. 1-8.
Notice of Allowance dated Mar. 21, 2017 issued on U.S. Appl. No. 15/009,468, pp. 1-5.
Complaint by Tris Pharma, Inc. against Teva Pharmaceuticals USA, Inc., C.A. No. 2:20-cv-05212-KM-JBC, dated Apr. 28, 2020.
Defendant Teva Pharmaceuticals USA, Inc.'s Answer, Affirmative Defenses, and Counterclaims to Plaintiff's Complaint, C.A. No. 2:20-cv-05212-KM-JBC, dated Jun. 29, 2020.
Notice of Allowance dated Nov. 18, 2016 issued on U.S. Appl. No. 15/200,625, pp. 1-5.
Non-Final Office Action dated Apr. 6, 2020 issued on U.S. Appl. No. 16/700,517 and Response dated Sep. 8, 2020, pp. 1-24.
Notice of Allowance dated Jan. 9, 2019 issued on U.S. Appl. No. 15/258,695.
Non-Final Office Action dated Jun. 28, 2018 issued on U.S. Appl. No. 15/258,695 and Response dated Nov. 28, 2018.
Applicant-Initiated Interview Summary filed for U.S. Appl. No. 15/258,695, dated May 16, 2018.
Final Office Action dated Dec. 22, 2017 issued on U.S. Appl. No. 15/258,695 and Response dated Feb. 23, 2018.
Non-Final Office Action dated Apr. 21, 2017 issued on U.S. Appl. No. 15/258,695 and Response dated Sep. 19, 2017.
Examiner-Initiated Interview Summary dated Aug. 29, 2017 issued on U.S. Appl. No. 15/258,695.
Notice of Allowance dated Jan. 9, 2019 issued on U.S. Appl. No. 15/258,700.
Advisory Action dated Sep. 13, 2018 issued on U.S. Appl. No. 15/258,700.
Final Office Action dated May 16, 2018 issued on U.S. Appl. No. 15/258,700, and Response dated Aug. 8, 2018.
Applicant-Initiated Interview Summary dated May 16, 2018 issued on U.S. Appl. No. 15/258,700.
Non-Final Office Action dated Aug. 23, 2017 issued on U.S. Appl. No. 15/258,700, and Response dated Feb. 23, 2017.
Plaintiff Tris Pharma, Inc.'s Response to Defendant Teva Pharmaceuticals USA, Inc.'s Initial Invalidity Contentions [Redacted], C.A. No. 2-20-cv-05212-KM-JBC, pp. 1-272, Nov. 10, 2021.
Certification of Non-Infringement and/or Invalidity of United States Pat. Nos. 8,202,537; 8,287,903; 8,999,386; 9,295,642; 9,545,399; 9,844,544 and 10,857,143 by Ascent Pharmaceuticals, Inc., pp. 1094, May 10, 2021.
Complaint by Tris Pharma, Inc. against Ascent Pharmaceuticals, Inc., C.A. No. 2:21-cv-12867-KM-ESK, In the District Court for the District of New Jersey, pp. 1-21, Jun. 22, 2021.
First Amended Complaint by Tris Pharma, Inc. against Ascent Pharmaceuticals, Inc., C.A. No. 2:21-cv-12867-KM-ESK, In the District Court for the District of New Jersey, pp. 1-26, Sep. 7, 2021.
Answer, Affirmative Defenses, and Counterclaims to First Amended Compaint by Ascent Pharmaceuticals, Inc., C.A. No. 2:21-cv-12867-KM-ESK, In the District Court for the Disrict of New Jersey, pp. 1-24, Oct. 29, 2021.
[Corrected] Defendant's Responsive Claim Construction Brief, *Tris Pharma, Inc.* v. *Teva Pharmaceuticals USA, Inc.*, C.A. No. 2:20-cv-05212, pp. 1-35, Jun. 7, 2021.
Tris Pharma Inc's First Amended Complaint, *Tris Pharma, Inc.* v. *Teva Pharmaceuticals USA, Inc.*, C.A. No. 2:20-cv-05212, pp. 1-22, Sep. 16, 2021.
Defendant Teva Pharmaceuticals USA, Inc.'s Answer, Affirmative Defenses, and Counterclaims to Plaintiff's First Amended Complaint, *Tris Pharma, Inc.* v. *Teva Pharmaceuticals USA, Inc.*, C.A. No. 2:20-cv-05212, pp. 1-40, Sep. 23, 2021.
Plaintiff Tris Pharma, Inc.'s Answer to Defendant Teva Pharmaceuticals USA, Inc.'s Counterclaims to Plaintiff's First Amended Complaint *Tris Pharma, Inc.* v. *Teva Pharmaceuticals USA, Inc.*, C.A. No. 2:20-cv-05212, pp. 1-22, Oct. 7, 2021.
Tris Pharma, Inc., Dyanavel: Highlights of Prescribing Information, Nov. 2021 (revised Jun. 2022), pp. 1-20.
Tris Pharma, Inc., Dyanavel: Highlights of Prescribing Information, May 2017, pp. 1- 30.
FDA.org, Center for Drug Evaluation and Research (App. No. 210526Orig1s000)—Administrative and Correspondence Documents, Dyanavel XR, Apr. 2016, pp. 1-18.
FDA.org, Center for Drug Evaluation and Research (App. No. 210526Orig1s000)—Multi-Discipline Review, Dyanavel XR, Jul. 2018, pp. 1-69.
FDA.org, Center for Drug Evaluation and Research (App. No. 210526Orig1s000)—Other Reviews, Dyanavel XR, Feb. 2018, pp. 1-69.
FDA.org, Center for Drug Evaluation and Research (App. No. 210526Orig1s000)—Product Quality reviews, Dyanavel XR, Jun. 2018, pp. 1-69.
FDA.org, Center for Drug Evaluation and Research (App. No. 210526Orig1s000)—Proprietary Name Reviews, Dyanavel XR, Apr. 2018, pp. 1-21.
FDA.org, Corrected Supplemental Approval (NDA 208147/S-103, NDA 210526/S-003), Feb. 2022, pp. 1-5.
FDA.org, Supplemental Approval (NDA 208147/S-103, NDA 210526/S-003, Dyanavel XR), Jun. 2022, pp. 1-4.
Tris Pharma, Inc., Tris Pharma Announces Development of a Very Low Sodium and Once-Nightly Oxybate Formulation (LiquiXR), Jul. 2022, pp. 1-3.
Tris Pharma, Inc., Tris Pharma Announces Publication of Study Results Highlighting the Efficacy and Safety of Dyanavel® XR (amphetamine) Tablets for the Treatment and Symptoms of ADHD in Adults, Jul. 2022, pp. 1-3.
First Amended Complaint by Tris Pharma, Inc. against Ascent Pharmaceuticals, Inc.—Exhibit A, C.A. No. 2:21-cv-12867-KM-EES, in the District Court for the District of New Jersey, pp. 1-23, Sep. 7, 2021, pp. 1-23.
Certificate of Service for Plaintiff's Answer to Counterclaims, C.A. No. 2:21-cv-12867-KM-EES, in the District Court for the District of New Jersey, p. 1, Nov. 19, 2021, p. 1.
Tris Pharma, Inc.'s Opening Post-Trial Brief (redacted), *Tris Pharma, Inc.* v. *Teva Pharmaceuticals USA, Inc.*, C.A. No. 2:20-cv-05212, pp. 1-65, Aug. 25, 2022, pp. 1-65.

(56) References Cited

OTHER PUBLICATIONS

Teva's Post-Trial Opening Brief (redacted), *Tris Pharma, Inc. v. Teva Pharmaceuticals USA, Inc.*, C.A. No. 2:20-cv-05212, pp. 1-56, Aug. 25, 2022, pp. 1-56.
Teva's Post-Trial Responsive Brief (redacted), *Tris Pharma, Inc. v. Teva Pharmaceuticals USA, Inc.*, C.A. No. 2:20-cv-05212, pp. 1-47, Aug. 25, 2022, pp. 1-47.
Teva's Post-Trial Responsive Brief ($2^{nd}$ submission, redacted), *Tris Pharma, Inc. v. Teva Pharmaceuticals USA, Inc.*, C.A. No. 2:20-cv-05212, pp. 1-47, Aug. 25, 2022, pp. 1-47.
Opinion (amended), *Tris Pharma, Inc. v. Teva Pharmaceuticals USA, Inc.*, C.A. No. 2:20-cv-05212, pp. 1-66, Sep. 6, 2022, pp. 1-66.
Order (amended), *Tris Pharma, Inc. v. Teva Pharmaceuticals USA, Inc.*, C.A. No. 2:20-cv-05212, pp. 1-2, Sep. 6, 2022, pp. 1-2.

\* cited by examiner

EXTENDED RELEASE AMPHETAMINE TABLETS

CROSS-REFERENCE TO RELATED APPLICATIONS

This application claims the benefit of the priority of U.S. Patent Application No. 62/562,464, filed Sep. 24, 2017, which is hereby incorporated by reference in its entirety.

BACKGROUND OF THE INVENTION

Amphetamine (contracted from alpha-methylphenethylamine) exists as two stereoisomers (enantiomers): levoamphetamine and dextroamphetamine. Amphetamine refers to the racemic free base, which are equal parts of the two enantiomers in their pure amine forms. Amphetamine is a potent central nervous system (CNS) stimulant of the phenylethylamine class that is used in the treatment of attention deficit hyperactivity disorder (ADHD) and narcolepsy [see, e.g., Adderall® IR Prescribing Information". United States Food and Drug Administration. Barr Laboratories, Inc. March 2007. pp. 4-5. Retrieved 2 Nov. 2013], was at one time used as an appetite suppressant, and has been reported to sometimes be prescribed off-label for its past medical indications, such as depression, obesity, and nasal congestion [Heal D J, et al (June 2013). "Amphetamine, past and present—a pharmacological and clinical perspective". J. Psychopharmacol. 27 (6): 479-496; S. Berman et al, Mol Psychiatry, February 2009; 14(2): 123-142]].

Pharmaceutical drugs classed as amphetamines include formulations containing salts of d-amphetamine (DextroStat®, Dexedrine®), mixed d- and l-amphetamine (Adderall®), d-methamphetamine (Desoxyn®), and a d-amphetamine pro-drug compound, lisdexamfetamine dimesylate (Vyvanse®). Reports of abuse of amphetamines date back to shortly following introduction of injectable forms of amphetamine. See, Berman et al, cited above. Because of its abuse potential, amphetamine and its salts, optical isomers, and salts of its optical isomer, are Schedule II substances controlled by the US Food and Drug Administration. 21 CFR. Sec. 1308.12 Schedule II. Amphetamine abuse has been reported to lead to tolerance and physical and psychological dependence, and is characterized by consuming increasingly higher dosages, and by the "binge and crash" cycle, when users attempt to maintain their high by overindulging on these drugs. Berman et al, cited above.

Both Adderall® (immediate-release) tablets and Adderall® XR capsules contain d-amphetamine and l-amphetamine salts in the ratio of 3:1. Following administration of Adderall® (immediate-release), the peak plasma concentrations occurs in about 3 hours for both d-amphetamine and l-amphetamine. The time to reach maximum plasma concentration ($T_{max}$) for Adderall® XR is about 7 hours, which is about 4 hours longer compared to Adderall® (immediate-release) [www3.us.elsevierhealth.com/-DrugConsult/Top_200/Drugs/e3289.html]. There have been reports of rebound effects with long-acting amphetamine products such as Adderall® XR [DJ Cox, et al, Journal of Child and Adolescent Psychopharmacology. February 2008, Vol. 18, No. 1: 1-10]. Symptoms include irritability, excessive talking, hyperactivity and insomnia. See, also, S. M. Berman et al, Mol Psychiatry. 2009 February; 14(2): 123-142, which reports on the history of the medical use of amphetamines since the early twentieth century.

US 2003/0099711 describes compositions comprising drugs bound to ion exchange resin particles and coated with a water-permeable, film-forming polymer. Among the several dozen drugs listed are amphetamine and dextroamphetamine. U.S. Pat. No. 4,996,047 also describes dozens of drugs, including amphetamine and dextroamphetamine, which may be selected to be bound to an ion exchange resin and coated with a water-permeable diffusion barrier coating. See, also, U.S. Pat. No. 2,990,332 (ionic exchange resin complexes with amphetamine).

U.S. Reissue patents 41,148 and RE 42,096 describe oral pulsed dose amphetamine delivery systems having an immediate release amphetamine and a delayed enteric release amphetamine component with mixed amphetamine salts. Among the specific amphetamine salts described are dextroamphetamine sulfate, dextroamphetamine saccharate, amphetamine aspartate monohydrate, and amphetamine sulfate, which are present in Shire's Adderall® product [see, Adderall® product literature]. It has been reported that the four salts are metabolized at different rates and have different half-lives, resulting in a less dramatic onset and termination of therapeutic action as compared to a single salt amphetamine preparation. SM Berman et al, Mol Psychiatry, February 2009: 14(2):124-142.

U.S. Pat. No. 7,776,917 refers to a conjugate comprising amphetamine and homoarginine, a salt of the conjugate, or a combination thereof.

U.S. Pat. No. 8,343,546 describes the treatment of an ion exchange resin with one or more sugar alcohols in order to prevent swelling. Amphetamine is identified amongst the many drugs which may be bound to the ion exchange resin.

U.S. Pat. No. 8,597,684 describes a composition containing a mixture of a pH-independent, modified release barrier coated amphetamine—ion exchange resin complex, an uncoated amphetamine—ion exchange resin complex, and an optional uncomplexed amphetamine or salt thereof. See, also, e.g., U.S. Pat. No. 8,883,217, which was also published as US 2014/0127306 and related U.S. Pat. No. 8,062,667. A subsequently published document, US 2013/0243869, refers to a pharmaceutical composition in which an ADHD-effective agent is complexed with ion exchange resin particles to form drug-resin particles, wherein said ADHD effective agent is a mixture of dextro- and levo-amphetamines. The composition may contain a mixture of uncoated drug-resin particles and a delayed-release coated drug-ion exchange resin complex. US 2014/0050796 describe mixtures of dextro- and levo-amphetamine complexed with ion exchange resin particles which comprise 20 to 50% uncoated drug—resin particles and 50 to 80% drug-resin particles coated with a delayed release coating.

US 2014/0050796 reports that its compositions offer advantages over Adderall® XR by minimizing the amount of sulfates used. This document reports that such sulfate compounds could form alkyl sulfonates and that the FDA recommends limiting or excluding alkyl sulfonates from drug formulations. This document also reports that the presence of ethanol causes dose dumping in Adderall® XR, which dose dumping the authors claim is minimized in their composition. In one embodiment [Paragraph 0019], the compositions of the '796 application are substantially free of dextroamphetamine saccharate and/or amphetamine aspartate.

US 2004/0220277 and WO 2004/071501 describe amphetamine compositions in which the molar ratio of l-amphetamine to d-amphetamine released therefrom in a time period later in the day is higher than the ratio released in a time period earlier in the day. These applications permit delivery of l-amphetamine and/or d-amphetamine as separate enantiomers, optionally delivered in combination with the racemic dl-amphetamine.

US 2013/0079415 describes drugs comprising an amphetamine or a salt thereof and an amphetamine pro-drug lisdexamphetamine.

There remains a need for a quick-acting, stable, extended release amphetamine product which can be conveniently delivered in a form suitable for patients who have difficulty swallowing whole tablets and capsules.

SUMMARY OF THE INVENTION

Amphetamine extended release compositions are described which provides in a single composition an immediate release of amphetamine with a fast onset of therapeutic effect and a therapeutic effect through an extended release. In certain embodiments, the therapeutic effect is about 13 hours. In certain embodiments, the compositions provide the extended release therapeutic effect with a formulation providing a higher percentage of immediate release components as compared to extended release components. Further, in certain embodiments, the compositions have a single plasma concentration peak for both d-amphetamine and l-amphetamine post-dosing. Tablets which are both chewable and which may also be orally disintegrating, orally dissolvable, and/or dispersible, are provided. These compositions provide easy administration for patients who have difficulty swallowing pills, especially for the pediatric and geriatric patients. Further because chewing does not alter the extended release properties of the product, patients have option to swallow, dissolve in the mouth (buccal cavity) or to chew a solid unit dose tablet without affecting the release property of the product. Additionally, the compositions can be dose titrated without altering the release profile of the composition, i.e., by splitting the tablet. Methods of treating patients in need thereof with these amphetamine (AMP) extended release compositions are further provided.

In one aspect, an orally administrable extended release amphetamine tablet comprising: an immediate release and at least about a 13-hour therapeutic effect for d-amphetamine and for l-amphetamine, a single plasma concentration peak for d-amphetamine and for l-amphetamine, and wherein the immediate release component comprises greater than 60% w/w immediate release amphetamines based on the total weight of amphetamines in the tablet, and wherein the tablet further comprises: (A) a modified release amphetamine component which comprises at least one modified release barrier coated amphetamine—cation exchange resin complex—optional matrix which comprises (i) two or more amphetamines bound to the same cation exchange resin or each bound to a different cation exchange resin, wherein when the optional matrix is present, the amphetamine—cation exchange resin complex—matrix further comprises a hydrophilic polymer or copolymer or a hydrophobic polymer and (ii) a water-insoluble, water-permeable, non-ionic modified release barrier coating which provides a modified release to the two or more amphetamines, wherein the two or more amphetamines are at least a d-amphetamine and an l-amphetamine, wherein the d-amphetamine and the l-amphetamine are provided by d-amphetamine and at least one of (d,l)-amphetamine and l-amphetamine; and (B) a first immediate release amphetamine component which comprises d-amphetamine or a pharmaceutically acceptable salt thereof, and l-amphetamine or a pharmaceutically acceptable salt thereof, or mixtures thereof, wherein the d- and l-amphetamine are provided by d-amphetamine and at least one of (d,l)-amphetamine and l-amphetamine; (C) a second immediate release amphetamine component which comprises an amphetamine—cation exchange resin complex in an optional matrix, wherein the amphetamine—cation exchange resin complex—optional matrix comprises at least a d-amphetamine and an l-amphetamine both bound to the same cation exchange resin or each bound to different cation exchange resins, wherein the d-amphetamine and the l-amphetamine are provided by d-amphetamine and at least one of (d, l)-amphetamine or l-amphetamine.

In another embodiment, the composition of the invention contains two counterions to the amphetamines.

The immediate release, modified release, titratable amphetamine composition is a chewable tablet, which is optionally scored for accurate, easy division or splitting. In such an embodiment, the modified release component may comprise about 40% or less of the total amphetamines in the tablet, based on the weight of the free amphetamine base, and further wherein the immediate release component provides about 60% or more of the total amphetamines in the tablet, wherein the weight is measured on the basis of free amphetamine base.

In one embodiment, a chewable tablet as provided herein is further characterized by also being an orally disintegrating tablet. In a further embodiment, the invention provides a method of treating patients with a disorder for which amphetamines are regulatory approved by administering an amphetamine extended release composition as described herein.

Still other aspects and advantages of the invention will be apparent from the following detailed description of the invention.

DETAILED DESCRIPTION OF THE INVENTION

Figure 1:
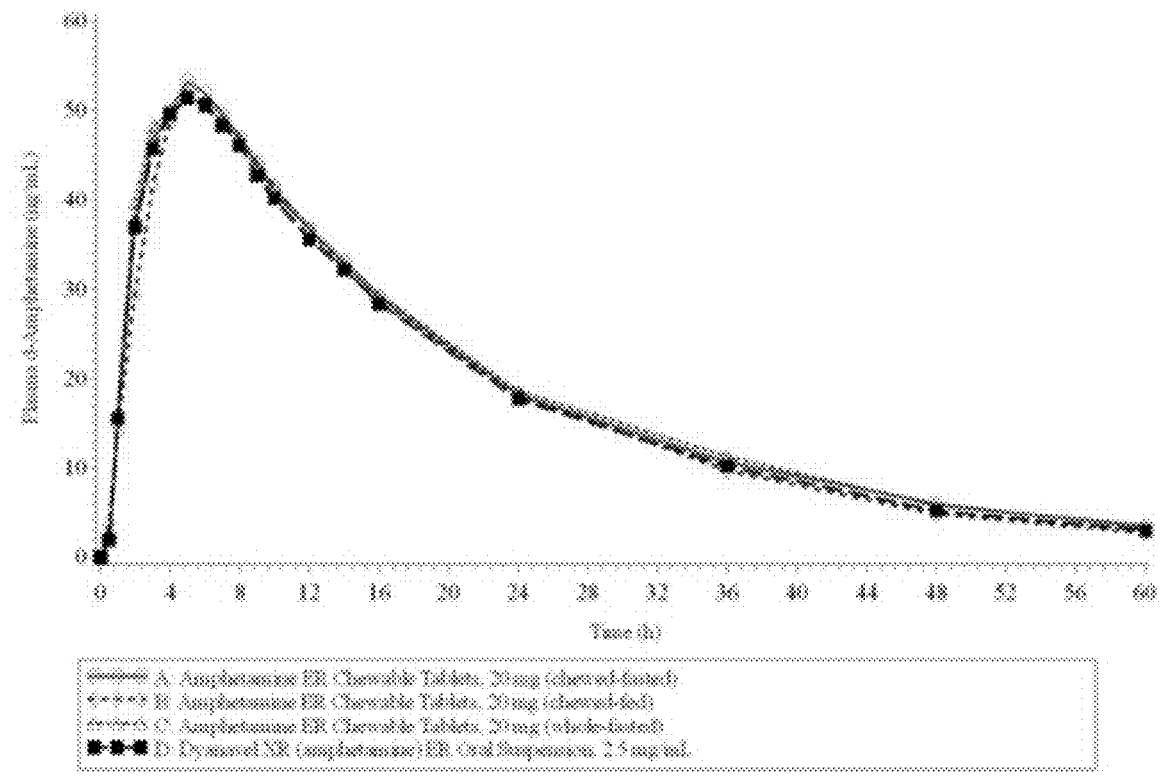
FIG. 1 provides a graph of the plasma concentration profile for d-amphetamine following administration of a chewed 20 mg tablet under fasted conditions (A), a chewed tablet under fed conditions (B) or a tablet swallowed whole (C), as compared to a liquid ER suspension product (line D).

The present invention provides amphetamine extended release compositions in which at least two different forms of amphetamine are provided in different release profiles, i.e., a modified release amphetamine component and an immediate release amphetamine component. In one embodiment, there is more than one immediate release component, one of which has a faster onset, e.g., up to about 100% of this faster onset is released within about 10 to about 20 minutes, and a second immediate release component, e.g., up to about 100% is released within about 1 hour. In one embodiment, at least two different amphetamine compounds (e.g., racemic amphetamine, d-amphetamine, l-amphetamine, mixtures thereof, or salts thereof) are present in each of the modified release and immediate release profiles.

As used herein, the term "amphetamine", abbreviated herein "AMP" is used to refer generally to amphetamine compounds, encompassing racemic amphetamine and the separate enantiomers thereof: dextro- or dex- (d)-amphetamine, and/or levo (l)-amphetamine. Racemic amphetamine is also termed herein (d,l)-amphetamine and is generally understood to contain a 1:1 ratio of d- to l-amphetamine. However, a racemate produced containing other ratios of these enantiomers may be used in the preparing the compositions described herein. Methods of preparing optically pure amphetamine enantiomers have been described. See, e.g., U.S. Pat. Nos. 3,028,430; 2,906,665A (l-amphetamine alginate); U.S. Pat. No. 6,399,828 (preparing amphetamines from phenylpropalamines); U.S. Pat. No. 8,487,134B2 (production acylated amphetamine, dexamphetamine and methamphetamines), the disclosures of which are incorporated by reference. Various amphetamine active pharmaceutical ingredients (API)—grade compounds can be purchased commercially (e.g., Gyma Laboratories of America, Cambrex, Johnson Matthey). Typically these compounds are purchased in the form of a pharmaceutically acceptable salt thereof, such as the mesylate, hydrochloride, saccharate, sulfate, aspartate salt, or a hydrate of such a salt. These or other pharmaceutically acceptable salts include e.g., non-toxic, inorganic and organic acid addition salts, are known in the art. Exemplary salts include, but are not limited to, 2-hydroxyethanesulfonate, 2-naphthalenesulfonate, 3-hydroxy-2-naphthoate, 3-phenylpropionate, acetate, adipate, alginate, amsonate, aspartate, benzenesulfonate, benzoate, besylate, bicarbonate, bisulfate, bitartrate, borate, butyrate, calcium edetate, camphorate, camphorsulfonate, camsylate, carbonate, citrate, clavulariate, cycloperitanepropionate, digluconate, dodecylsulfate, edetate, edisylate, estolate, esylate, ethanesulfonate, fumarate, gluceptate, glucoheptanoate, gluconate, glutamate, glycerophosphate, glycollylarsanilate, hemisulfate, heptanoate, hexafluorophosphate, hexanoate, hexylresorcinate, hydrabamine, hydrobromide, hydrochloride, hydroiodide, hydroxynaphthoate, iodide, isothionate, lactate, lactobionate, laurate, laurylsulphonate, malate, maleate, mandelate, mesylate, methanesulfonate, methylbromide, methylnitrate, methylsulfate, mucate, naphthylate, napsylate, nicotinate, nitrate, N-methylglucamine ammonium salt, oleate, oxalate, palmitate, pamoate, pantothenate, pectinate, persulfate, phosphate, phosphate/diphosphate, picrate, pivalate, polygalacturonate, propionate, p-toluenesulfonate, saccharate, salicylate, stearate, subacetate, succinate, sulfate, sulfosalicylate, suramate, tannate, tartrate, teoclate, thiocyanate, tosylate, triethiodide, undecanoate, and valerate salts, and the like. In one embodiment, in the compositions described herein, the saccharate salt form of the amphetamine is not selected for use in a composition where the counterion will be present in the composition.

As used herein, a "counterion" is the ion that accompanies an ionic species (e.g., an amphetamine base) in order to maintain electric neutrality. For example, when an amphetamine salt is dissolved, the "counterion" is the dissociated ionic species, e.g., from an amphetamine saccharate, the saccharate would be the counterion.

Although not encompassed with the term "amphetamine", it will be understood that derivatives, prodrugs (e.g., esters), and/or pre-prodrugs of the racemic amphetamine, dex(d)-amphetamine, or l-amphetamine, may be selected for use in a composition described herein. One example of such a drug includes, e.g., lisdexamphetamine. Methods for producing such derivatives, prodrugs and pre-prodrugs have been described. See, e.g., U.S. Pat. No. 8,487,134 (production of acylated amphetamine, dexamphetamine and methamphetamines); US20120157706 (methods and compositions for preparing lisdexamfetamine and salts thereof), the disclosures of which are incorporated herein by reference.

In one embodiment, the compositions provided herein are described as containing a total ratio of d- to l-amphetamine of about 3 parts by weight d-amphetamine to about 1 part by weight l-amphetamine (e.g, 2.60 parts by weight to 3.40 parts by weight d-amphetamine, or 3 parts by weight to 3.4 parts by weight d-amphetamine, or about 3.2 parts by weight d-amphetamine) to about 1 part by weight l-amphetamine. Further, the modified release and/or one or both of the immediate release components may also contain a similar ratio. When making this calculation, the total d-amphetamine amount is used, regardless of whether contributed by the racemate or the dexamphetamine enantiomer. Unless otherwise specified, the racemate contains 50% d- and 50% l-amphetamine. Throughout this specification, when weight percentages and/or ratios are provided for amphetamines in each of the active components, the weight percentage or ratio is calculated based on the amount of amphetamine base in each component.

As used herein the term "uncomplexed" refers to an amphetamine, refers to the faster onset immediate release component, wherein a second immediate onset component is present, and specifically includes the corresponding amphetamine free base, as well as pharmacologically active and physiologically compatible salts form thereof, including acid addition salts, hydrates thereof, and hydrates (anhydrous, semihydrates, etc) of these salts; specifically excluded from the term "uncomplexed amphetamine" is an amphetamine which bound to or complexed with a cation exchange resin.

The immediate release amphetamine component also comprises an amphetamine—cation exchange resin complex, optionally in combination with a matrix forming polymer which is characterized herein as the "slower" onset immediate release component. This component may be referred to as "uncoated" in that it may contain no coating, or if any coating is present, the coating either does not function to modify the release characteristics of the drug (from immediate release to modified release). This slower onset immediate release component may contain a blend of two separate uncoated amphetamine—cation exchange resin complexes, each of which contains a single amphetamine component bound to a cation exchange resin (e.g., (d,l)-amphetamine—cation exchange resin complex and/or d-amphetamine—cation exchange resin complex). Alternatively, two different amphetamines may be bound to a single cation exchange resin complex (e.g., both (d,l)- and d-amphetamine—cation exchange resin complex). Methods for loading multiple drugs onto a single resin have been described. See, e.g., U.S. Pat. Nos. 8,062,667, 8,329,224 B2 and Published Patent Application No. 2007-0148239, which describes multiple loadings onto an ion exchange resin; and WO 2007/001300, which generally describes drug loading and conjugating more than one active drug with a single resin particle, the disclosures of which are incorporated by reference herein. In still another embodiment, compositions may be produced in which amphetamine—cation exchange resin complexes containing multiple amphetamines (e.g., dl-,d-amphetamine—cation exchange resin complex) and containing a single amphetamine (d-amphetamine—cation exchange resin complex) are combined. The immediate release component contains a plurality of particulate, amphetamine—cation exchange resin complexes.

As used herein, the term "modified release" refers to compositions in which the release of at least one of the active components (i.e., (d,l)-amphetamine, d-amphetamine or l-amphetamine) is longer than its immediate release form. "Modified release" may encompass sustained release, extended release, or delayed release. For convenience, "modified release" is used to refer to the amphetamine component of the composition, whereas "extended release" is used to refer to the present composition which provides both immediate release and modified release components. In one embodiment, the modified release profile extends to at least 8 hours. More desirably, the composition provides a therapeutic effect through at least about 12 hours to about 18 hours, about 13 hours to about 16 hours, or about 13 hours. The release profile may be assessed via in vitro dissolution using techniques known to those of skill in the art [e.g., USP basket method, paddle method, channel flow method, or other methods known in the literature]. The release profile can be assessed in vivo (e.g., for bioavailability determinations), using plasma concentrations to assess maximum plasma concentration ($C_{max}$) and area under the curve (AUC).

A therapeutic result for amphetamine is not solely related to plasma levels of the drug. Thus, "a therapeutically effective amount" of amphetamine includes the minimum amount of the drug required to provide a clinically observable psychological and/or behavioral response. Unless otherwise specified, this is determined following a single or "initial" administration of an extended release amphetamine composition as described herein. A therapeutically effective amount of amphetamine can alternatively be defined as being at least the minimum amount of amphetamine which reduces or eliminates the symptoms associated with a condition for which amphetamine has been approved for use. Appropriate doses are discussed in more detail later in this specification. Therapeutic effect may be assessed, e.g., by the Swanson, Kotkin, Agler, M-Flynn, and Pelham (SKAMP) deportment scale throughout the day [Wigal S B, et al, Psychopharmacol Bull, 1988: 34(1): 47-53]. Other suitable assays and methods may be selected by one of skill in the art.

The term "initial administration" is defined for purposes of the present invention as the first single dose of an extended release amphetamine composition administered to a patient or subject or the first dose administered to a patient or subject after a suitable washout period. As used herein, the term "patient" and "subject" are used interchangeably to refer to humans who are being dosed with an extended release amphetamine composition as provided herein.

The modified release component has a coating which provides a modified release profile to the amphetamine(s). The coating is over the amphetamine—cation exchange resin complex, which is optionally in a matrix. As described in more detail below, the modified release component may contain a blend of two different modified release, pH-independent, barrier coated—amphetamine—cation exchange resin complexes, each of which contains a single amphetamine component bound to a cation exchange resin. Alternatively, at least two different amphetamines may be bound to a single cation exchange resin complex (e.g., (d,l)-amphetamine, d-amphetamine, and/or l-amphetamine), using methods such as are described herein. In still another embodiment, compositions may be produced in which two or more different amphetamines on the same cation exchange resin is combined with a single amphetamine bound to a separate cation exchange. The resulting modified release component contains a plurality of particulate, barrier coated amphetamine—cation exchange resin complexes, which are separately coated with a pH-independent release, high tensile strength, water insoluble, water-permeable modified release barrier coating prior to be admixed with the immediate release components. In the compositions described herein, typically, the excipients are selected such that they do not contribute at all, or to any measurable amount, to the modified release properties of the composition.

Whether selected from the racemate (d,l), or the separate enantiomers: d-amphetamine or l-amphetamine, the active drug may be present in the form of a salt, hydrate, or hydrate of a salt. One suitable salt is the saccharate, succinate, hydrochloride, aspartate or sulfate salt form. However, other pharmaceutically acceptable salts may be selected.

As used herein, the term "free amphetamine" or "free amphetamine base" refers to the weight of the amphetamine base, i.e., exclusive of any salt, hydrate, polistirex or complex form (i.e., without the counterion, any water content, or and/or ion exchange resin).

In one embodiment, an amphetamine extended release chewable tablet of the invention contains amphetamines in different forms, (a) a modified release barrier coated amphetamine—cation exchange resin complex, optionally in a matrix, (b) a slower onset immediate release uncoated amphetamine—cation exchange resin complex, optionally in a matrix, and (c) a faster onset immediate release uncomplexed amphetamine. The modified release, barrier coated amphetamine—cation exchange resin complex, optionally in a matrix, may contain a mixture of one or more of (d,l)-amphetamine, d-amphetamine and/or l-amphetamine complexed on separate ion exchange resins, or a mixture of d-amphetamine and l-amphetamine complexed onto the same cation exchange resin complex.

The compositions provided herein are characterized by providing both immediate release amphetamine and modified release amphetamine. The term "immediate release" ("IR") refers to the release of an active ingredient (e.g., an amphetamine) from a pharmaceutical formulation where the rate of release of the active pharmaceutical ingredient from the pharmaceutical formulation is not substantially retarded by means of a controlled release matrix or other such means and where the components of the pharmaceutical formulation are designed such that, upon ingestion, maximum exposure of said active pharmaceutical ingredient to body tissues occurs in the minimum period of time. As described herein, an "immediate release" amphetamine component releases about 100% in less than 1 hour. The present invention provides for an extended release composition having two different immediate release amphetamine components, each of which provides a different release profile.

In one embodiment, the composition contains at least a first, faster onset immediate release component, i.e., release of about 100% in less than 30 minutes, with at least 50% release in less than 20 minutes and, preferably in as few as ten minutes, or sooner. In some embodiments, 80 to 100% is released within about 10 to 20 minutes, or about 10 minutes. This faster onset immediate release component comprises at least one uncomplexed amphetamine. A second, different, slower onset immediate release component provides a different immediate release pharmacokinetic profile, which releases in less than about an hour, as soon as about 30 minutes, or as soon as about 20 minutes, with at least some measurable release as early as about 10 to 15 minutes. Suitably this slower onset immediate release component is an uncoated amphetamine—cation exchange resin complex, which is optionally in a matrix with a matrix forming polymer. When present in the immediate release component, the matrix forming polymer is selected so that the resulting uncoated amphetamine—cation exchange resin complex (optionally in a matrix) retains an immediate release profile. For convenience, the optional matrix is not referenced in every phrase where the uncoated complex is discussed. However, it will be understood that this uncoated complex may contain such a component. The release profiles of the two different immediate release components may overlap, e.g., the slower onset immediate release component may begin releasing before 100% of the faster onset immediate release component is completely released.

In certain embodiments, the modified release barrier coated amphetamine—cation exchange resin complex, optionally in a matrix provides an amount of about 10% w/w to about 40% w/w, about 15% w/w, about 20% w/w, about 25% w/w, about 30% w/w, or about 40% w/w of the total amphetamine components in the composition (based on the free amphetamine base(s)). The two immediate release components combine to provide about 60% w/w to about 90% w/w, or about 70%, or about 75%, or about 80%, or about 85% w/w, or values there between of the total amphetamine components in the composition. The uncoated amphetamine—cation exchange resin complex component is designed to be immediate release as defined herein, and as such, does not contain a coating which functions to delay release (e.g., no functional amount of an extended release barrier coating or enteric coat). Suitably, immediate release amphetamine—cation exchange resin complex is present in an amount of about 20% w/w to about 75% w/w, or about 25% w/w to about 70% w/w, about 50% w/w, about 55% w/w, about 60% w/w, about 70% w/w, about 75% w/w of the amphetamine components in the composition based on the total amount of free amphetamine base. The extended release component and the immediate release amphetamine—cation exchange resin complex are further in combination with an uncomplexed amphetamine drug(s). The other immediate release component, which is an uncomplexed amphetamine drug, is present in an amount of about 5% w/w to about 25% w/w, or about 15% w/w to about 25% w/w, or about 20% w/w of the amphetamine components in the compositions based on the total amount of free amphetamine base. In one embodiment, a composition contains a ratio of amphetamine in a coated amphetamine—cation exchange resin complex: uncoated amphetamine—cation exchange resin complex: uncomplexed amphetamine is about 20 to about 30: about 50 to about 60: about 15 to about 25. In one embodiment, the weight percentages of amphetamine contributed by each of the two immediate release components are the same. However, in other embodiments, it may be desirable to provide amphetamine in the immediate release components in different weight percentages.

An "amphetamine—cation exchange resin complex" refers to the product resulting from loading an amphetamine which has been disassociated with any counterion and bound to a cation exchange resin. Methods for preparing such complexes have been described, e.g., in WO 2007/109104, the disclosure of which is incorporated herein by reference. This describes the complexation which occurs when the active drug and the cation exchange resin are mixed together in an aqueous medium to facilitate the "exchange" between the salt of the amphetamine and the "cation" of the cation exchange resin and the formation of the complex, which may be referred to as "amphetamine polistirex". WO 2007/109104 also describes polyvinylacetate-based barrier coatings which are particularly well suited for use in the formulations described herein to provide a modified release coat over the amphetamine—cation exchange resin complex—matrix. However, one skilled in the art can select other barrier coatings to provide the modified release characteristics to amphetamine—cation exchange resin complex—matrix. The term "amphetamine—cation exchange resin complex" and "amphetamine polistirex" are used interchangeably throughout this specification. Further, the term "amphetamine—cation exchange resin complex" or "amphetamine polistirex" includes when more than one form of an amphetamine is complexed to the same cation exchange resin, e.g., a cation exchange resin may have both racemic (d,l)-amphetamine and d-amphetamine complexed thereto.

As used herein, a "precoated" amphetamine—cation exchange resin complex or a "precoated" amphetamine—cation exchange resin complex—matrix refers to a particle which is to be subsequently coated with a barrier coating as defined herein. In some embodiments, where the amphetamine—cation exchange resin or amphetamine—cation exchange resin complex—matrix is to be used as one of the immediate release components and no barrier coating is to be applied, it is referred to as "uncoated". In some embodiments, the "immediate release coated amphetamine—cation exchange resin complex" may have a selected coating thereon, where the coating does not confer any modified release to the amphetamine.

As used herein, a barrier coat is a water-permeable, water-insoluble, pH-independent polymer or co-polymer which in the present invention confers modified release to the coated amphetamine—cation exchange resin complex—matrix. In one embodiment, the barrier coat is pH-independent, non-ionic and is applied, e.g., as an aqueous suspension, over the precoated amphetamine—cation exchange resin complex—matrix and forms a separate layer thereon. In another embodiment, the barrier coat is pH-independent, non-ionic and is applied as a solvent-based coating, over the amphetamine—cation exchange resin complex—matrix and forms a separate layer thereon. In still another embodiment, the barrier coat is pH-independent, ionic and is applied over the amphetamine—cation exchange resin complex—matrix to form a separate layer thereon. Preferably, the barrier coat is directly over the amphetamine—cation exchange resin complex—matrix and the barrier coat layer, i.e., there are no intervening layers between the barrier coat and the amphetamine—cation exchange resin complex—matrix. Depending upon the polymeric material selected, the barrier coat polymer or co-polymer may be cured to maximize its properties. These polymers and their curing requirements are discussed in more detail elsewhere in this specification.

An "amphetamine—cation exchange resin complex—matrix" refers to an amphetamine—cation exchange resin complex which is further combined, e.g., prior to or during granulation, with a polymeric material which forms a matrix with the amphetamine—cation exchange resin complex.

The term "matrix forming polymer" or "matrix forming polymeric material" refers to both water-insoluble (hydrophobic) polymers and co-polymers and water-soluble (hydrophilic) polymers and co-polymers which form a matrix with the amphetamine—cation exchange resin complex upon being admixed or granulated therewith. Suitably, the matrix forming polymer is non-reactive with the AMP and the cation exchange resin. The matrix forming polymer may be a water-insoluble polymers/co-polymers and polymer systems which have been described as release retardants [see, e.g., polymers discussed in U.S. Pat. No. 8,062,677, the disclosure of which is incorporated herein by reference], and those hydrophilic polymer systems which have been described in the literature as impregnating or solvating agents [see, e.g., polymers discussed in U.S. Pat. Nos. 8,062,677 and 4,221,778, incorporated herein by reference]. In one embodiment, an amphetamine—cation exchange resin complex—matrix may include more than one matrix-forming polymer system. For example, an amphetamine—cation exchange resin complex—matrix may contain both a hydrophilic polymer and a hydrophobic polymer.

An immediate release "uncoated amphetamine—cation exchange resin complex" may optionally be in a matrix. In this instance, the matrix forming polymer does not substantially alter the ability of the amphetamine—cation exchange resin complex—matrix to provide an immediate release profile. For example, a polyvinylpyrrolidone may be selected as a matrix forming polymer. Alternatively, the matrix forming polymer may alter the release rate of this complex while still maintaining an immediate release profile as defined herein.

The following terms are used in the specification and are to be interpreted in accordance with the definitions herein.

"$C_{max}$" is the maximum plasma concentration, calculated as the geometric or arithmetic mean of the individual maximum blood plasma concentrations over the sampling period.

The term "$T_{max}$" is the time at which the peak (maximum) observed blood plasma drug concentration for each individual participating in the bioavailability study over the sampling period.

The term "$AUC_{0-\infty}$" or "$AUC_{inf}$" is the mean area under the analyte (e.g., from plasma or serum) concentration-time curve extrapolated to infinity. It is calculated as the mean of the area under the analyte concentration-time curve from time 0 extrapolated to infinity, calculated for each individual participating in the bioavailability study and may be the geometric or arithmetic mean. In certain embodiments, $AUC0-\infty=AUC0-t+Ct/kel$, where Ct is the last measurable analyte concentration and kel is the apparent first-order elimination rate constant.

$AUC_{0-t}$ is the area under the plasma/serum/blood concentration-time curve from time zero to time t, where t is the last time point with measurable analyte concentration. t may be, e.g., 1 hour ($AUC_{0-1}$), 2 hours ($AUC_{0-2}$), 3 hours ($AUC_{0-3}$), 4 hours ($AUC_{0-4}$), 5 hours ($AUC_{0-5}$), or at 0-4 hours, 4-8 hours, 8-12 hours, 8-13 hours, under fasting and/or fed conditions, or at different intervals, including those where t is 13 hours, 14 hours, 15 hours, 16 hours, 17 hours, 18 hours, or up to 24 hours as end time points.

Partial AUC may be useful in determining bioequivalence, where the AUC is determined based on a specific fragment of the $AUC_{t-t+x}$. These fragments may be, e.g., from 0-2 hours, 2-4 hours, 5-8 hours, 8-13 hours, or other time points.

In certain embodiments, the AUC values are calculated by the linear trapezoidal rule.

"Bioequivalent" means the pharmacokinetic profile of a test composition is within the range of about 80% to about 125%, when compared to the values of one or more of the AUC values or the $C_{max}$ of the reference composition. See, e.g., US Department of Health and Human Services. Guidance for Industry: Bioavailability and Bioequivalence Studies for Orally Administered Drug Products—General Considerations. Washington, D.C.: Center for Drug Evaluation and Research; March 2003. For example, in certain embodiments, a bioequivalent product is required to be within 80% to 125% of $AUC_{0-\infty}$, or within 90% to 110% of $AUC_{0-\infty}$. In certain embodiments, a bioequivalent product is bioequivalent over preselected partial AUC values. For example, in certain embodiments, being bioequivalent to the $AUC_{0-2}$ values of the composition of the invention is desired. Typically in order to be bioequivalent, a product must match not just a single partial AUC, but also either be bioequivalent over the entire time period and/or other partial AUC time periods In order to declare the absence of a food effect on the test formulation, the 90% CIs of the relative mean plasma d-amphetamine and l-amphetamine of one or more of $AUC_{0-2}$, $AUC_{0-5}$, $AUC_{5-t}$, $AUC_{0-\infty}$, and/or $C_{max}$ of the test product under fed versus fasted conditions should be between 80.00 and 125.00%, inclusive. See, e.g., US Department of Health and Human Services. Guidance for Industry: Food Effect Bioavailability and Fed Bioequivalence Studies. Rockville, Md.: Center for Drug Evaluation and Research; December 2002. In one embodiment, a composition of the invention has no food effect, i.e. there is no statistical difference in one or more of the pharmacokinetic parameters, including, e.g., Cmax, AUC0-∞", and/or one or more partial AUCs, when patients are administered a dose under fasted conditions as compared to fed conditions.

In order to establish relative bioavailability of a test formulation (e.g., administered as a whole tablet to the reference or chewing under fasted conditions), the 90% confidence intervals (CIs) of the ratios of geometric mean plasma d-amphetamine and l-amphetamine of one or more of $AUC_{0-2}$, $AUC_{0-5}$, $AUC_{5-t}$, $AUC_{0-\infty}$, and/or $C_{max}$, of the test product in relation to the reference product should be between 80.00 and 125.00%, inclusive. See, e.g., US Department of Health and Human Services. Guidance for Industry: Bioavailability and Bioequivalence Studies for Orally Administered Drug Products—General Considerations. Washington, D.C.: Center for Drug Evaluation and Research; March 2003.

When reference is made to "different amphetamines", it will be understood that a racemic amphetamine, a d-amphetamine, and an l-amphetamine are considered herein to be "different" from one another. As a whole, they may be considered "amphetamines". Similarly, the other types of amphetamines or amphetamine derivatives as defined herein are encompassed by this definition. In some circumstances, counterions which form salts with these free bases are referred to as "different counterions". This will be readily understood to refer to the counterions of a different free radical which is capable of forming a pharmaceutically acceptable salt with an amphetamine free base.

The term "half-life" is the apparent terminal elimination half-life ($T_{1/2}$).

The words "comprise", "comprises", and "comprising", and "contain", "containing", and "contains" are to be interpreted inclusively rather than exclusively. The words "consist", "consisting", and its variants, are to be interpreted exclusively, rather than inclusively.

As used herein in reference to numeric values provided herein, the term "about" may indicate a variability of as much as 10% (up to ±10% of the indicated value, including). This includes lower variabilities (e.g., ±1%, ±2%, ±3%, ±4%, ±5%, ±6%, ±7%, ±8%, ±9%, and other values between 0 and 10).

Amphetamine—Cation Exchange Resin Complexes

As described herein, a polistirex or drug—cation exchange resin may contain one form of an amphetamine, e.g., racemic (d,l) amphetamine, or two or more amphetamine compounds. An amphetamine can be complexed with, or loaded onto, a cation exchange resin, using methods which are known in the art. See, e.g., WO 2007/109104, the disclosure of which is incorporated by reference, and the documents cited therein. One or more different amphetamine compounds [e.g., racemic, d-, or l-amphetamine] may be synthesized or obtained from commercial sources as described above.

Cationic exchange resins are readily selected for use as described herein. For example, cationic exchange resins vary in strength, i.e., in their ability to exchange cations. In one embodiment, a relatively strong cationic resin, e.g., Amberlite® IRP69, manufactured by Dow Chemical (a sulfonated copolymer of styrene and divinylbenzene) is selected. Alternatively, one may select a relatively weak cationic exchange resin, e.g., Amberlite® IRP88 [Dow Chemical (which acquired previous manufacturer Rohm & Haas) a crosslinked polymer of methacrylic acid and divinylbenzene)], a weakly acidic (potassium ion) cation exchange resin with 4% cross-linked methacrylate (100 to 500 mesh, equivalent to about 150 microns to about 27 microns, ASTM standard) or Amberlite® IRP64 (a methacrylic acid and divinylbenzene polymer (hydrogen ion) polacrilex resin, Rohm and Haas, with a particle size ranging from 100 to 400 mesh (equiv to 35 microns to 150 microns, ASTM standard size), capacity ~10 meq/g by dry weight). Further, either regularly or irregularly shaped particles may be used as cation exchange resins according to the present invention. Regularly shaped particles are those particles that substantially conform to geometric shapes such as spherical, elliptical, cylindrical and the like, which are exemplified by Dowex® 50WX8 (The Dow Chemical Company). Irregularly shaped particles are all particles not considered to be regularly shaped, such as particles with amorphous shapes and particles with increased surface areas due to surface channels or distortions. Irregularly shaped ion-exchange resins of this type are exemplified by Amberlite® IRP-69 (manufactured by Dow Chemical), the use of which is illustrated in the examples below. This cation exchange resin is a sulfonated polymer composed of polystyrene cross-linked with about 8% of divinylbenzene, with an ion-exchange capacity of about 4.5 to 5.5 meq/g of dry resin ($H^+$-form). Another cation exchange resin having similar properties is Dowex® 50WX8 (H+ form, linear formula, $C_{10}H_{12}\cdot C_{10}H_{10}\cdot C_8H_8)_x$, 200-400 mesh particle size, which is equivalent to about 75 microns to about 35 microns, ASTM standard). Amberlite® IRP-69 consists of irregularly shaped particles with a size range of about 100 to about 500 mesh (about 150 microns to about 27 microns, ASTM standard). Dowex® 50WX8 is more regularly shaped. Resins are generally purchased with a size ranging from about 25 microns to about 400 microns. However, other sizes may be selected, or larger sized particles may be milled to provide smaller particle sizes.

The selected ion-exchange resins may be further treated by the manufacturer or the purchaser to maximize the safety for pharmaceutical use or for improved performance of the compositions. Impurities present in the resins may be removed or neutralized by the use of common chelating agents, anti-oxidants, preservatives such as disodium edetate, sodium bisulfite, sodium metabisulfite, and so on by incorporating them at any stage of preparation either before complexation or during complexation or thereafter. These impurities along with their chelating agent to which they become bound may be removed before further use of the cation exchange resin.

A method for preparing a drug—cation exchange resin complex involves reacting the drug(s) and cation exchange resin in water under conditions which permit formation of a complex. Typically, the reaction step involves combining the active drug(s) or a pharmaceutically acceptable salt thereof and a pharmaceutically acceptable, water-insoluble, cation exchange resin in an aqueous admixture and mixing for a sufficient amount of time to allow binding of the drug free base to the cation exchange resin. Optionally, a single amphetamine drug may be used in the following methods in a single complexing (loading) step to form an amphetamine—cation exchange resin complex containing a single amphetamine drug (e.g., d-amphetamine). These steps may be repeated in separate processes for the other amphetamine—cation exchange resin complexes to be used in a composition of the invention. Alternatively, a mixture of amphetamine drugs may be used in a single complexing step to provide an amphetamine—cation exchange resin complex which contains a mixture of amphetamine drugs (e.g., (d,l)-amphetamine, d-amphetamine, and/or l-amphetamine). Mixing during the complexing step may be, e.g., for about 1 hour to about 5 hours, or about 2 hours, followed by further processing which may take up to about 72 hours or longer.

The order of admixing in the complexation step; the drug(s) and the cation exchange resin may be performed in multiple ways. Optionally, a cation exchange resin for preparing a complex may be pre-washed, e.g., according to its manufacturer's instructions or as previously described. See, e.g., U.S. Pat. No. 8,062,667, the disclosure of which is incorporated by reference herein.

As described above, the reaction between the drug (e.g., (d,l)-amphetamine and/or d-amphetamine) and cation exchange resin occurs in a suspension having a water content in excess of 50% w/w, more typically in the range of about 60% to about 90% w/w to facilitate complexing of the amphetamine with the cation exchange resin. While the moisture content may be provided by water alone, optionally, solvents in addition to water may be present in this aqueous reaction slurry. For example, suitable solvents may include isopropyl alcohol, methanol or ethanol, or mixtures thereof in the aqueous slurry. In certain embodiments, the moisture content of the slurry may be reduced to below about 50% w/w, and more desirably, in the range of about 20% w/w to about 30% w/wand/or, more preferably 2 to 10% w/w. During this processing, all or substantially any remaining counter-ion of the starting pharmaceutically active salt of the drug is removed through the washing steps.

The total amount of amphetamine that can be complexed with a resin will typically range from about 5% to about 50% by weight of the amphetamine—cation exchange resin complex particles. A skilled artisan with limited experimentation can determine the optimum loading for any amphetamine—cation exchange resin complex. In one embodiment, loading of about 10% to about 40% by weight, more desirably, about 15% to about 30% by weight, or about 25% of the amphetamine—cation exchange resin complex particles can be employed. In one embodiment, a composition of the invention contains amphetamine complexed to a sodium polystyrene sulfonate resin in at a ratio of 20 parts amphetamine (based on the weight of the amphetamine salt) to 300 parts cation exchange resin or 80 parts amphetamine (based on the weight of the amphetamine salt) to 100 parts cation exchange resin. In another embodiment, the amphetamine (based on the weight of the amphetamine salt) to resin ratio is 4:1 to 1:15, or 4:1 to about 1:4, or about 1:1. In a further embodiment, the amphetamine—cation exchange resin may contain more than one amphetamine compound bound to the same cation exchange resin, e.g., (d,l)-amphetamine and d-amphetamine. In certain embodiments, both the modified release component and the immediate release amphetamine—cation exchange resin complex contain two different amphetamines bound to the same cation exchange resin complex. In another embodiment, one of the immediate release components contains a blend of amphetamine—cation exchange resin complexes, in which a (d,l)-amphetamine—cation resin complex and a d-amphetamine—cation exchange resin complex are blended or admixed. In another embodiment, the modified release component contains a blend of barrier coated amphetamine—cation exchange resin complex—(optional matrix), in which a modified release, barrier coated (d,l)-amphetamine—cation exchange resin complex and a modified release, barrier coated d-amphetamine—cation exchange resin complex are blended or admixed to provide the modified release component. In another embodiment, the modified release component contains a blend of barrier coated amphetamine—cation exchange resin complex—(optional matrix), in which a modified release, barrier coated d-amphetamine—cation resin complex and a modified release, barrier coated l-amphetamine—cation resin complex are blended or admixed to provide the modified release component. In yet another embodiment, the immediate release component includes an uncoated d-amphetamine—cation exchange resin complex and an uncoated l-amphetamine—cation exchange resin complex blended or admixed. In such an instance, the blend may comprise about 3.2% by weight d-amphetamine to about 1% by weight l-amphetamine, which weight percent is based on the weight of the amphetamine without calculating the weight contribution of the other components of the complex (e.g., ion exchange resin, or any matrix or coating polymer present). Following the complexation reaction, an amphetamine—cation exchange resin complex may be, in no particular order, milled to achieve a desired size range and dried (e.g., to a moisture content below about 10%, e.g., about 3% to about 7%), and then stored for future use. In one embodiment, the complex is milled or passed through a sieve to provide a particle size ranging from about 40 microns to about 4120 microns to enhance mouth feel (i.e., texture), or about 50 microns to about 250 microns. These particles may be either regularly or irregularly shaped. In some embodiments, the average particle size of the uncoated amphetamine—cation exchange resin complex or the average particle size of the coated amphetamine—cation exchange resin complex is milled to a size of about 100 to about 200 microns. These particle sizes maybe determined using sieve analysis through a sieve shaker having USP standard wire mesh sieves conforming to ASTM specifications. Alternatively, other suitable methods known to those of skill in the art may be used to achieve this result.

In another embodiment, rather than drying for storage, a sufficient amount of water is removed from the wet mass containing the formed complex (i.e., the slurry in which the reaction occurred) to optimize uniform application of a granulating agent, followed by further removal of moisture. Typically, the washing steps, filtration, and/or other steps for removal of moisture result in removal of substantially all of counter-ions from the drug—cation exchange resin complex.

A number of the processing steps described herein, including, e.g., loading, pre-washing, complexing and granulation may be carried out in a multi-purpose apparatus, e.g., such as the AFD450 processor [Pall SeitzSchenk] or another similar and larger scale multi-purpose apparatus which is available commercially [e.g., by Rosenmund, U.S. Pat. No. 5,609,835]. The vessel is capable of or adapted for pivoting and has a single chamber with the capacity for handling a reaction/crystallization, filtration, resuspension, and drying. Such a vessel is typically provided with a water jacket connected with a thermostatically controlled heating and cooling system. Alternatively, this vessel is used for only a single processing step in conjunction with multiple different apparatus, including, e.g., granulators (e.g., the GMX-75 high shear granulator), a dryer, and others which are known in the art.

In one embodiment, a matrix forming polymer is combined with the amphetamine—cation exchange resin complex following only partial complexation, or by reducing the moisture content of the wet amphetamine—cation exchange resin complex to a range of between about 15 to about 25%, or another suitable amount. Treatment of the amphetamine—cation exchange resin complex with the matrix forming polymer is as follows.

Amphetamine—Cation Exchange Resin Complex—Matrix

Optionally, a matrix-forming polymer is used to assist in processing an uncoated or precoated amphetamine—cation exchange resin complex. For example, a matrix-forming polymer may be used to facilitate granulation of the immediate release amphetamine—cation exchange resin complex, or as desired, e.g., in preparation for coating of an uncoated amphetamine—cation exchange resin complex.

In one embodiment, a polyvinylpyrrolidone polymer [e.g., such as may be purchased commercially as KOLLIDON® 30] is combined with the amphetamine—cation exchange resin complex in order to facilitate granulation prior to coating. Other hydrophilic polymeric granulating agents may include water-soluble polymeric materials which have been described in the art as impregnating agents or solvating agents and which function in the present application as granulating agents. In one embodiment, the granulating agent is a polyethylene glycol. Examples of desirable impregnating/solvating agents include those described in US Published Patent Application 2007/0215511, Sep. 20, 2007, and US 2003/0099711, which are incorporated herein by reference, or in U.S. Pat. No. 4,221,778 and published US Patent application Publication No. US 2003/0099711, the disclosures of which are incorporated herein by reference. Specific examples of other impregnating agents include propylene glycol, polyethylene glycol, polyvinyl alcohol, hydroxypropyl methylcellulose, hydroxypropyl cellulose, and sorbitol.

Optionally, the amphetamine—cation exchange resin complexes of the present invention may be admixed or granulated with a water-soluble or water-insoluble polymer or a combination of a water-insoluble polymers prior to the application of the water-permeable diffusion barrier coating described herein. Upon admixture, these polymers do not form a separate layer on the amphetamine—cation exchange resin complex. These polymers form a matrix therewith. Examples of suitable matrix forming polymers include, for example, a polyvinyl acetate polymer or a mixture of polymers containing same (e.g., KOLLICOAT® SR 30D), cellulose acetates, ethylcellulose polymers (e.g., AQUACOAT™ ECD-30 or SURELEASE™), acrylic based polymers or copolymers (e.g., represented by the EUDRAGIT® polymer family of acrylic resins), cellulose phthalate, or any combination of such water-insoluble polymers or polymer systems. These matrix-forming polymers when used may further prolong or alter the release of the amphetamine from the cation exchange resin complex/matrix and maximize attaining the desired release profile. One suitable polymer is a polyvinyl acetate polymer as described herein or an acrylic polymer from the EUDRAGIT® family. Examples of suitable acrylic polymers from the EUDRAGIT® family may include, e.g., a copolymer comprising ethyl acrylate and methyl methacrylate (e.g., EUDRAGIT® NE-30D), or EUDRAGIT® RS30D, RL30D, which are largely pH-independent polymers. EUDRAGIT® RS30D is a 30% aqueous dispersion of poly (ethyl acrylate-co-methyl methacrylate-co-trimethylammonioethyl methacrylate chloride) in a ratio of 1:2:0.1; other aqueous dispersions of this copolymer may be selected. Eudragit® RL30 D is a 30% aqueous dispersion of poly (ethyl acrylate-co-methyl methacrylate-co-trimethylammonioethyl methacrylate chloride) 1:2:0.2; other aqueous dispersions of this copolymer may be selected for use in the invention. Although less desirable, certain pH-dependent (enteric) polymers including, e.g., members of the EUDRAGIT polymer family, e.g., the L, S, and E, polymers and others which are commercially available may be selected.

The quantity of matrix forming polymer in an amphetamine—cation exchange resin complex—matrix typically ranges from about 1% to about 30%, or about 3 to about 20%, or about 3 to about 10%, about 10% to about 15%, about 15 to 25%, or about 5% or more by weight of the uncoated or amphetamine—cation exchange resin particulates prior to their being optionally coated. However, higher or lower amounts may be selected. In one embodiment, where it is desired for the matrix forming polymer to have little or no effect on release rate, a hydrophilic polymer may be selected and used in a higher amount, whereas a hydrophobic release retardant if selected for use will be used at a lower amount. Following admixing, the amphetamine—cation exchange resin complex particles with the matrix forming polymer, the mixture is dried and the amphetamine—cation exchange resin complex—matrix granules are milled appropriately to the desired particulate size.

For the amphetamine—cation exchange resin complex—matrix which will be coated and the uncoated amphetamine—cation exchange resin complex, the particles are milled though a size below about 420 microns, or generally in the range of about 50 microns to about 420 microns, or about 100 microns to about 420 microns. This can be achieved, e.g., using a CO-MIL device fitted with a 40 mesh screen. In one embodiment, the particles have an average size of about 100 to about 250 microns, or about 100 to about 200 microns. In some cases, the milling may be carried out before the complete drying of the complex or complex matrix and then again further drying followed by milling to obtain the desired complex characteristics. These particle sizes maybe determined using sieve analysis through a sieve shaker having USP standard wire mesh sieves conforming to ASTM specifications.

Barrier Coat for Modified Release

The modified release component of an amphetamine—cation exchange resin complex—matrix with a barrier coating which modifies the release profile of the active amphetamine(s) such that the amphetamine has at least about a modified release profile. Suitably, the barrier coating has a pH-independent release (i.e., it is not an enteric coating which has pH-dependent release) and is a water—insoluble, water—permeable coating material. In a preferred embodiment, the chewable tablet lacks an enteric or other pH-dependent coating.

Suitably the properties of the barrier coating provide modified release properties to the barrier coated amphetamine—cation exchange resin complex, which is amphetamine-cation exchange resin optionally in matrix. When the matrix is present, the barrier coating is applied over the amphetamine—cation exchange resin complex—matrix. The barrier coating provides the modified release component with resistance to grinding forces which enables the portions of a chewable tablet of the invention to provide a modified release amphetamine profile even when cut into pieces.

In one embodiment, the barrier coating has a characteristic high flexibility or elongation (elasticity) at break measured by the texture analyzer TA-XT2 HiR (Stable Microsystems) and by the method reported by the manufacturer in its literature [i.e., Jan-Peter Mittwollen, Evaluation of the Mechanical Behavior of Different Sustained Release Polymers, Business Briefing: Pharmagenerics, 2003, pp. 1-3, BASF]. In certain embodiments, the modified release barrier coating layer comprises a modified release polymeric coating material, such as described in more detail below, and at least one plasticizer incorporated into the barrier coating polymer to enhance high flexibility or elongation (elasticity) of the polymeric film coating. Elongation at break may be measured by the texture analyzer TA-XT2 HiR (Stable Microsystems) and/or by the method reported by the manufacturer in its literature [i.e., Jan-Peter Mittwollen, Evaluation of the Mechanical Behavior of Different Sustained Release Polymers, Business Briefing: Pharmagenerics, 2003, pp. 1-3, BASF] and maybe at least about 100%, of at least about 125% and preferably in a range between about 150% to about 400% as compared to the original polymeric film. Suitably, the plasticizer is selected so as to not substantially increase the tackiness of the polymer film greater than about 2 (wherein the film is measured by the Hossel method referenced above independent of any composition on which it has been deposited). Generally, a plasticizer is used in the percent range, or a mixture of plasticizers combine to total about 2 to about 50% by weight of the coating layer, more preferably about 2.5% to about 30% by weight, or about 5% to about 20% by weight of the coating layer on the coated amphetamine—cation exchange resin complex.

In one embodiment, the barrier coating layer is about 10% to about 55%, by weight, or about 10% to about 50%, by weight, of the amphetamine—cation exchange resin complex—optional matrix in order to provide the modified release component. In another embodiment, the barrier coating layer is about 20% to about 40%, about 25% to about 35% by weight, or about 30%, by weight, of the amphetamine—cation exchange resin complex—matrix (i.e., prior to coating). Still other suitable ranges can be determined by one of skill in the art, having been provided with the information herein.

The barrier coating is applied over the uncoated amphetamine—cation exchange complex—optional matrix (e.g., as an aqueous dispersion or a solution), dried, and milled or passed through a screen such that the barrier coated amphetamine—cation exchange complex—optional matrix particles are in the same size range as described in the preceding paragraph, i.e. an average of about 100 microns to about 300 microns, or an average of about 150 microns to about 250 microns.

In one embodiment, the barrier coating is applied as an aqueous dispersion which is dried in order to provide the desired modified release profile. In the case of an aqueous—based polyvinylacetate coating, the coating is cured in order to provide the desired release profile.

In one embodiment, the barrier coating is applied as an aqueous dispersion of a water insoluble polymer comprising a polyvinyl acetate polymer, or a blend of polymers comprising a polyvinyl acetate polymer. In one embodiment, the barrier coating further contains a plasticizer, which can facilitate uniform coating of the amphetamine—cation exchange resin complex—optional matrix and enhances the tensile strength of the barrier coating layer.

One coating composition useful in the present invention is applied in the form of an aqueous dispersion containing polyvinylacetate (PVA) polymer based aqueous coating dispersion and a plasticizer. The PVA is insoluble in water at room temperature. The PVA may be used in either substantially pure form or as a blend. Where the barrier coating comprises a PVA polymer, the PVA polymer is present in an amount of about 70% to about 90% w/w of the final barrier coating layer, at least about 75%, at least about 80%, about 85% w/w of the final barrier coating layer. Generally, a plasticizer is used in the percent range, or a mixture of plasticizers combine to total about 2 to about 50% by weight of the coating layer, more preferably about 2.5% to about 20% by weight of the coating layer on the coated amphetamine—cation exchange resin complex. Preferably a plasticizer is in a range of about 2.5 to about 15% by weight of the coating layer based on the coated complex provides the most desirable properties. Suitable plasticizers may be water soluble and water insoluble. Examples of suitable plasticizers include, e.g., dibutyl sebacate, propylene glycol, polyethylene glycol, polyvinyl alcohol, triethyl citrate, acetyl triethyl citrate, acetyl tributyl citrate, tributyl citrate, triacetin, and Soluphor® P (2-pyrrolidone), and mixtures thereof. Other plasticizers are described in patent application publication US 2003/0099711 A1, May 29, 2003, page 4 (0041) the disclosure of which is incorporated herein by reference.

A commercial polyvinylacetate blend contains primarily a polyvinylacetate polymer, a stabilizer, and minor amounts of a surfactant such as sodium lauryl sulfate. Where the barrier coating comprises PVP as the stabilizer component, the final barrier coating layer generally contains about 5 to about 10% w/w of polyvinyl pyrrolidone. In one desired embodiment, the aqueous based barrier coating solution is KOLLICOAT® SR 30 D (BASF Corporation) and whose composition is about 27% PVA polymer, about 2.7% polyvinylpyrrolidone (PVP), about 0.3% sodium lauryl sulfate (solids content 30% w/w), mixed with a plasticizer. See, also, U.S. Pat. Nos. 6,066,334 and 6,026,277, which is incorporated by reference herein. The PVP and surfactant help stabilize the aqueous dispersion of the PVA. Generally, such stabilizing components are present in an amount totaling less than about 10% w/w, and preferably less than about 5% w/w. Optionally, a selected surfactant is present in an amount of about 1% or less. In one embodiment, the surfactant is a non-ionic surfactant. Optionally, an ionic surfactant may be selected.

In a particularly desirable embodiment, the desired modified release is obtained when the coating layer formed by application of the aqueous dispersion containing the KOLLICOAT® SR-30D—plasticizer is dried and cured. Preferably, the coating is cured for about 1 to about 24 hours. In alternate embodiments, the coating is cured for about 4 to about 16 hours, and preferably about 5 hours at high temperature, e.g., about 50° C. to about 65° C., and preferably about 60° C. Thus, in one embodiment, the coated amphetamine—cation exchange resin complex—matrix has a cured water-permeable, high tensile strength, water insoluble, barrier coating comprising a non-ionic polymer and a plasticizer and having an elongation factor in the range of about 150% to 400% over the amphetamine—cation exchange resin complex—matrix. In one embodiment, the barrier coating comprises a polyvinylacetate polymer, a stabilizer, a surfactant and a plasticizer. In one embodiment, a barrier coating comprises about 2.5 to about 30% of plasticizer, about 70 to about 90% polyvinylacetate, about 5 to about 10% polyvinylpyrrolidone, and about 0.1 to about 1% surfactant. See, e.g., US Published Patent Application No. US 2007/0215511A, published Sep. 20, 2007, and its counterpart application, WO 2007/109104, the disclosures of which are incorporated herein by reference.

It may be possible utilize other aqueous or non-aqueous solvent based systems which do not require curing. For example, an aqueous based acrylic polymer (a EUDRAGIT® RL30D and EUDRAGIT® RS30D blend is described herein), but requires the addition of anti-tacking agent such as, e.g., talc or glycerol monostearate (GMS), in order to facilitate processing and even coating.

In one embodiment, the coating may be a EUDRAGIT® brand acrylate based coating materials [including, e.g., a poly (ethyl acrylate-co-methyl methacrylate-co-trimethyl-ammonioethyl methacrylate chloride) polymer system]. For example, EUDRAGIT® RS 30D [a pH-independent, 30% aqueous dispersion of poly (ethyl acrylate-co-methyl methacrylate-co-trimethylammonioethyl methacrylate chloride) 1:2:0.1)], or EUDRAGIT® RL 30D [a 30% aqueous dispersion, pH independent polymer, poly (ethyl acrylate-co-methyl methacrylate-co-trimethylammonioethyl methacrylate chloride) 1:2:0.2)] may be selected as the barrier coating. In one embodiment, a blend of EUDRAGIT® RS 30D and EUDRAGIT® RL 30D may be prepared to optimize the hydrophilicity/hydrophobicity of the film in order to achieve desirable release profiles.

Suitably, a plasticizer may be included in the coating layer. In one embodiment, the barrier coating comprises about 2 to about 50% by weight of the coating layer, more preferably about 2.5% to about 2030% by weight, or about 5% to about 20% by weight of the barrier coating layer. Individual or a combination of hydrophilic or lipophilic plasticizers with a dispersion or suspension containing the barrier coating polymer. Such plasticizers include, e.g., propylene glycol, polyethylene glycol, triacetin, triethyl citrate, dibutyl sebacate, vegetable oil, lipids, etc. Optionally, a suitable anti-tacking agent may be mixed with one of the EUDRAGIT® products to improve flow during coating and to address issues of tackiness of the product during processing. Suitable anti-tacking agents include, e.g., talc, glycerol monostearate (GMS), and mixtures thereof. Suitably, these agents are present in an amount of about 0.2%—4.5% w/w based on the dry weight of the coating polymer applied to form the coating layer of the modified release component. Typically, the coating layer resulting from application of the blend described in this paragraph is not subject to any curing.

Optionally, another barrier coating may be selected. In another embodiment, a non-aqueous solvent-based ethylcellulose, such as commercially available as the ETHOCEL™ products (Dow) may be modified in order to achieve the barrier coating characteristics defined herein, e.g., by addition of a sufficient amount of plasticizer to improve flexibility and/or by curing to a sufficient temperature to achieve the desired release rate. Dow's web site describes three of these products, Std 7 (viscosity of 6-8 mPa-s (CP); Std 10 (9-11 mPa-s (CP)); Std 20 (18-22 mPa-S), each of which has a 48.0-49.5% ethoxyl content) as being useful for tablet coating. Further, optionally combining one of these polymers in combination with a water-soluble active and/or water-soluble excipient such as a METHOCEL™ cellulose ether and/or CARBOWAX™ polyethylene glycols is further described. Alternatively, it may be possible to modify an aqueous based ethylcellulose barrier coating in order to achieve the modified release barrier coating characteristics required herein, e.g., by addition of a sufficient amount of plasticizer to improve flexibility and/or by curing to a sufficient temperature to achieve the desired release rate. See, e.g., the barrier coatings described in U.S. Pat. Nos.

6,066,334 and 6,046,277; see, also, e.g., U.S. Pat. Nos. 6,046,277 and 6,001,392; US Published Patent Application No. 2003/0099711 and related application WO 03/020242; WO 2006/022996 and related applications US Published Patent Application Nos. US 2005/0232986; US 2005/0232987; US 2005/0232993; US 2005/0266032; U.S. Pat. Nos. 7,067,116; 6,667,058, 6,001,392, the disclosures of which are incorporated herein by reference, among others.

In certain embodiments, the water-permeable diffusion barrier is selected from the group consisting of ethyl cellulose, methyl cellulose and mixtures thereof. In certain embodiments, the coating material is SURELEASE®, manufactured by Colorcon which is water based ethyl cellulose latex, plasticized with dibutyl sebacate or with vegetable oils. Other non-limiting coating materials included within the scope of the present invention are AQUACOAT®, manufactured by FMC Corporation of Philadelphia, which is ethylcellulose pseudolatex; solvent based ethylcellulose; shellac; zein; rosin esters; cellulose acetate; EUDRAGIT® products, manufactured by Rohm and Haas of Philadelphia, which are acrylic resins; silicone elastomers; poly(vinyl chloride) methyl cellulose; and hydroxypropylmethyl cellulose.

A coating as described herein may be applied using techniques described by the polymer manufacturer and/or techniques which are known to those of skill in the art. Conventional coating solvents and coating procedures (such as fluid bed coating and spray coating) can be employed to coat the particles. Techniques of fluid bed coating are taught, for example, in U.S. Pat. Nos. 3,089,824; 3,117,027; and 3,253,944. The coating is normally applied to the drug/resin complex, but alternatively can be applied to the resin before complexing with the drug. See, e.g., U.S. Pat. Nos. 6,001,392; 3,089,824; 3,117,027; and 3,253,944. Non-limiting examples of coating solvents include ethanol, a methylene chloride/acetone mixture, coating emulsions, methyl acetone, tetrahydrofuran, carbon tetrachloride, methyl ethyl ketone, ethylene dichloride, trichloroethylene, hexane, methyl alcohol, isopropyl alcohol, methyl isobutyl ketone, toluene, 2-nitropropane, xylene, isobutyl alcohol, n-butyl acetate.

The coated amphetamine—cation exchange resin complex—(optional matrix) is then dried and/or cured. The dried, optionally cured, coated amphetamine—cation exchange resin complex—optional matrix may be passed through a suitable screen in order to ensure that the particle size is in the desired range, e.g., capable of passing through a standard 40 mesh screen. In one embodiment, the dried, optionally cured, coated amphetamine cation exchange resin complex (optional matrix) granules have an mean particle size in the range of about 100 microns to about 420 microns, or about 75 microns to about 250 microns, about 150 to about 300 microns. In one embodiment, less than 10% of the coated particles are under 75 microns in size.

Finished Dose Formulations

The compositions described herein include amphetamine extended release chewable tablets. These compositions are orally administrable and readily titratable. The tablets maintain their extended release profile even when subject to chewing or division (e.g., splitting).

The one or more modified release barrier coated amphetamine—cation exchange resin complex—optional matrix, one or more uncoated amphetamine—cation resin complex and the one or more uncomplexed amphetamine may be prepared as described herein and blended together prior to combination with the excipients for formulation into a final chewable tablet formulation. Optionally, one or more of these components are prepared and dried (e.g., in powder form), either separately or together, for storage prior to formulation. Alternatively, the one or more modified release barrier coated amphetamine—cation exchange resin complex—optional matrix, one or more uncoated amphetamine—cation resin complex and the one or more uncomplexed amphetamine may be prepared separately as described above, and combined in any suitable order with the excipients present in the aqueous suspension base and/or the chewable tablet.

In one aspect the invention provides an amphetamine extended release chewable tablet, which is optionally also orally dissolving. Following administration of a single dose of the oral amphetamine extended release chewable tablet, in some embodiments, a therapeutically effective amount of amphetamine is reached in less than about thirty minutes, and as soon as about twenty, ten, or fewer minutes, and the formulation provides an extended release therapeutically effective profile to at least about 12 hours, or about 13 hours, or up to about 18 hours. Further, the chewable tablet may be scored, as dividing the tablet does not significantly modify the in vitro profile of the tablet portions resulting from split or other division of the intact tablet.

Further, because the amphetamine chewable tablet described herein retains its extended release properties even when scored, it can be divided into other suitable portions. This makes the chewable tablet readily titratable and convenient for physicians to reduce the dose for patients to introduce the drug in a smaller dose or incremental doses of medication for patients whose needs dictate such. This ability to divide the dose into portions allows physicians to take into consideration individual patient needs, including factors like age, body weight and individual response to the medication without the need for taking multiple doses over a twelve hour period of another product which offers only immediate release.

The amphetamine extended release chewable tablets are typically dry blended prior to being compressed into a chewable tablet. Suitably, the chewable tablet of the invention is solid blend which provides extended release properties even when scored such that when divided the separated tablet portions retain the extended release profile described herein. In certain embodiments, the tablets have a uniformly blended core containing all the active amphetamine components and are distinguished from tablets layered with different actives.

In one embodiment, the chewable tablet has a hardness of about 2.5 kilopond (kp) to about 20 kp or about 3 to about 15 kp. One (1) kilopond is one kilogram of force (kgf). Newtowns (N) are the SI unit of force and the SI standard for tablet hardness testing. 1 kilopond (kp) is equal to 9.80665 Newtons (N). Presented in Newton rounded to the nearest five, the chewable tablet has a hardness of about 45 N to about 245 N, about 75 N to about 200 N, or about 95 N to about 160 N. Optionally, the hardness may be dose proportional, with lower doses having lower hardness levels. For example, a 20 mg chewable tablet may have a hardness in the range of about 7 to about 14 kp (about 68 N to about 127 N), a 15 mg tablet may have a hardness in the range of about 3 to about 9 kp (about 29 N to about 88 N), and a 10 mg tablet may have a hardness in the range of about 3 kp to about 11 kp (about 29 N to about 108 N). In one embodiment, the hardness is determined following compression and prior to application of any color or other non-functional tablet coating as defined herein. In one embodiment, the tablet portions meet the USP Friability requirement. In one embodiment, the friability of both the intact tablet and the tablet portions are less than about 1.

A tablet of the invention is distinguished by being chewable and also being a rapid dissolve tablet or an orally dissolving tablet (ODT) that will dissolve in the mouth in less than 1 minute. An ODT has been defined as a solid dosage form containing medicinal substances that disintegrates rapidly, usually within a matter of seconds, when placed upon the tongue. In general, the total weight of the ODT is recommended not to exceed 500 mg. See, Guidance for Industry, Orally Disintegrating Tablets, US Department of Health and Human Services, Food and Drug Administration Center for Drug Evaluation and Research (CDER) December 2008. In one embodiment, the tablet provided herein is a unit dosage form which is about 375 mg to about 425 mg, or about 400 mg in total weight. In another embodiment, the tablet is a unit dosage form which is about 350 mg to about 375 mg, or about 360 mg in total weight. In a further embodiment, the tablet is a unit dosage form which is about 200 to about 250 mg, or about 240 mg in total weight.

In certain embodiments, the tablet may be an orally disintegrating tablet. In certain embodiments, the tablet may be an orally dispersible tablet.

In one embodiment, the excipients do not alter the modified release properties of the chewable tablet. The modified release profile is provided by the modified release barrier coated amphetamine—cation exchange resin complex—matrix component. The amphetamine components may be pre-blended in the desired ratio to one another prior to being admixed with the excipients, described below. Alternatively, each of the amphetamine components are added separately and blended with the excipients.

The amphetamine extended release chewable tablets may be prepared using one or more of a filler, one or more disintegrant, one or more binder, one or more a buffering agent, one or more lubricant, one or more glidant, or blends of these components. Suitably, the tablets also include taste and/or mouth feel enhancers including, e.g., one or more of a sweetener, a flavorant, a gum, or blends of these components. Optionally, the tablet may also contain a non-functional coating.

As used herein, a "non-functional coating" refers to a coating which contributes no detectable modified release functions. The non-functional coating may be a polymer which may serve as a moisture barrier to preserve the integrity of the tablet during storage or to facilitate application of a color coating layer. Additionally or alternatively, the non-functional coating may provide a color coating layer or improve the "smoothness" or mouth feel of the tablet. In one embodiment, the non-functional coating may increase the hardness of the tablet somewhat without affecting the chewability thereof.

Throughout the specification, where weight percentages of excipients and the active components are provided, the weight percentages are exclusive of any weight added by a non-functional coating. Weight percentages of these non-functional coatings, where present, are provided as weight added, in an amount of about 1% to about 20%, or about 2% to about 10%, or about 3% to about 5% weight added to the finished chewable tablet.

A chewable tablet may contain a filler or a mixture of fillers in the range of about 50% w/w to about 90% w/w, about 55% w/w to about 85% w/w, or about 60% w/w to about 70% w/w of the total tablet weight, or values therebetween. Suitable fillers may include, e.g., mannitol, lactose, maltose, fructose, sucrose, xylitol, maltitol, microcrystalline cellulose, dicalcium phosphate, guar gum, xanthan gum, tragacanth gum, pre-gelatinized starch, compressible sugar, calcium carbonate, magnesium carbonate, calcium sulfate, dextrates, maltodextrin. In one embodiment, a chewable tablet of the invention contains a blend of mannitol, xanthan gum, microcrystalline cellulose, and guar gum in an amount of about 60% w/w to about 75% w/w. In one embodiment, a gum or a combination of gums is provided in an amount of about 0.25% w/w to about 5% w/w, or about 0.25% to about 1% w/w. In another embodiment, microcrystalline cellulose is provided in an amount of about 10% w/w to about 25% w/w, or about 15% w/w to about 20% w/w based on the total tablet weight prior to any non-functional coating. A product containing a combination of microcrystalline cellulose and guar gum is commercially available as Avicel®, which contains a ratio of 80 parts by weight microcrystalline cellulose to 20 parts by weight guar gum. This blend of microcrystalline cellulose (MCC) and guar gum may be present in an amount of about 10% w/w to about 20% w/w of the total tablet weight.

A chewable tablet as described herein will also contain a disintegrant or blend of disintegrants in the range of about 1% w/w to about 25% w/w, or about 5% w/w to about 15% w/w, or about 10% w/w to about 14% w/w based on the total tablet weight. Suitable disintegrants include, e.g., crospovidone, sodium starch glycolate, croscarmellose sodium, carboxymethyl cellulose sodium, carboxymethylcellulose calcium, starch. In one embodiment, a tablet as described herein contains crospovidone in a range of about 5% w/w to about 10% w/w, or about 12% w/w based on the tablet weight prior to any non-functional coating being applied.

The binder for the chewable tablet may be absent (i.e., 0%), or optionally, present in an amount of about 1% w/w to about 15% w/w of the total tablet weight. Examples of suitable binders include polyvinylpyrrolidone (Povidone), hydroxypropyl methyl cellulose, hydroxypropyl cellulose, hydroxyethyl cellulose, methyl cellulose, polyvinyl alcohol, starch, acacia, alginic acid, sodium alginate.

In one embodiment, the chewable tablet contains a sweetener in an amount of about 0.01% w/w to about 3% w/w, or about 0.5% w/w to about 2% w/w, or about 1% w/w to about 2% w/w or about 1.5% w/w, based on the total tablet weight exclusive of any optional non-functional coating. Suitable sweeteners may include, e.g., Aspartame, Saccharin, Saccharin sodium, Sucralose, Sodium cyclamate, Xylitol, Acesulfame Potassium, and blends thereof. Optionally, in addition to functioning as a sweetener, an excipient may function as a filler. Examples of suitable sweeteners/fillers including, e.g., fructose, sucrose, xylitol, maltitol. Optionally, when performing both functions, the excipient may be present in an amount in excess of about 10% w/w of the tablet. In such an instance, additional sweetener may be omitted (e.g., present in 0% added sweetener). Alternatively, a second sweetener or a combination of sweeteners which differs from the filler is added in the amount provided in this paragraph in order to further enhance taste.

Suitably, the tablet may contain a buffering agent in an amount of about 0.1% w/w to about 5% w/w, or about 0.5% w/w to about 1.5% w/w based on the total tablet weight. Examples of suitable buffering agents include, e.g., citric acid, tartaric acid, malic acid, lactic acid, and acceptable salts thereof, and mixtures thereof. In one embodiment, the buffering agent adjust the pH of the tablet (if suspended in water) to a range of about 5 to about 6.

When an additional flavoring agent is added, the flavoring agent(s) may be added in an amount of about 0.05% w/w to about 3% w/w, or about 0.1% to about 1% w/w or about 0.5% w/w, based on the total weight of the tablet (exclusive of any optional non-functional coating). Suitable flavoring agents may include, both natural and artificial flavoring agents such as are generally available through several custom manufacturers around the world such as Fona [Illinois, US], Givaudan (Vernier, Switzerland), Ungerer & Company (Lincoln Park, N.J.), and International Flavors & Fragrances (New York, N.Y.) to name a few. Those skilled in the art will recognize that there are several commercial sources available including custom blenders. The flavorings may be blended prior to addition to the pharmaceutical composition or added separately. Still other flavoring agents such as bubble gum, cherry, strawberry, vanilla, grape, banana and other flavors or mixtures thereof may be selected.

Optionally, a colorant may be provided to the tablet to provide a desired visual appeal or trade dress. Such colorants may be added in the range of about 0.001 to about 1% w/w, or about 0.01% w/w to about 0.08% w/w or about 0.05% w/w, based on the total weight of the tablet (exclusive of any non-functional coating). Such colorants are available from a variety of sources including, e.g., Colorcon, Noveon, and Spectra. In one embodiment, no colorants are used in the tablet.

In order to facilitate production of the chewable tablet, excipients such as lubricants and glidants may be utilized. A lubricant may be utilized in an amount of about 0.1% w/w to about 5% w/w, about 0.2% w/w to about 4.5% w/w, or about 1.5% w/w to about 3% w/w of the total weight of the tablet. Examples of lubricants may include, e.g., magnesium stearate, sodium stearyl fumarate, stearic acid, zinc stearate, calcium stearate, magnesium trisilicate, polyethylene glycol, and blends thereof. In one embodiment, A glidant may be used in an amount of about 0.01% w/w to about 0.5% w/w, or about 0.1% w/w to about 0.3% w/w, based on the total weight of the tablet. Examples of suitable glidants include, e.g., silicon dioxide and tribasic calcium phosphate. In one embodiment, the glidant is silicon dioxide which is used in an amount of about 0.001% w/w to about 0.3% w/w or about 0.2% w/w.

Optionally, other excipients may be selected from conventional pharmaceutically acceptable carriers or excipients and well established techniques. Without being limited thereto, such conventional carriers or excipients include diluents, binders and adhesives (i.e., cellulose derivatives and acrylic derivatives), lubricants (i.e., magnesium or calcium stearate, or vegetable oils, polyethylene glycols, talc, sodium lauryl sulfate, polyoxy ethylene monostearate), thickeners, solubilizers, humectants, disintegrants, colorants, flavorings, stabilizing agents, sweeteners, and miscellaneous materials such as buffers and adsorbents in order to prepare a particular pharmaceutical composition. The stabilizing agents may include preservatives and anti-oxidants, amongst other components which will be readily apparent to one of ordinary skill in the art.

The following Tables provides exemplary formulations of amphetamine extended release compositions according to the invention, based on the total weight of the tablet. In certain embodiments, 5 mg, 10 mg, 15 mg, and 20 mg tablet strengths are provided as dose weight proportional formulations. The tablets are designed to disintegrate after chewing followed by ingestion or after swallowing the whole tablet.

In certain embodiments, a single powder blend is used to prepare tablets of all four strengths. The powder blend contains two active ion exchange resin complexes: Coated (d, dl) AMP Polistirex and Uncoated (d, dl) AMP Polistirex, blended with a racemic Amphetamine salt, or a hydrate thereof, and a (d) Dextroamphetamine salt. These may be blended together further blending with the remaining excipients before compression into the final tablet.

In certain embodiments, the excipients are present in an amount as follows:

| Ingredients | Quantity (mg/tablet) | | | | Quantity % (w/w) |
|---|---|---|---|---|---|
| | 5 mg | 10 mg | 15 mg | 20 mg | |
| Amphetamine base | 5 | 10 | 15 | 20 | 1-5% |
| Complexing Agent (Cation Exchange resin) | 10-40 | 20-80 | 35-120 | 60-150 | 5-20% |
| Optional Matrix Forming polymer/Binder | 0.33 | 0.66 | 0.99 | 1.3 | 0.01-0.5 |
| Plasticizer | 0.05-0.1 | 0.1-0.4 | 0.2-0.5 | 0.2-0.6 | 0.001-0.1 |
| Modified Release Coating | 1-4 | 2-8 | 3-12 | 4-16 | 0.5-2% |
| Filler(s) | 70-276 | 138-552 | 210-830 | 276-1106 | 40-80 |
| Optional Sweetener | 1.5-6 | 3-12 | 4.5-18 | 6-20 | 1-3 |
| Optional Flavoring Agent | 0.5-2 | 1-4 | 1.5-6 | 2-8 | 0.025-1 |
| Disintegrant | 12-48 | 24-96 | 36-144 | 48-192 | 6-20 |
| Glidant(s) | 1.2-4.8 | 2.4-9.6 | 3.6-14.4 | 4.8-19.20 | 0.6-1.8 |
| Lubricant | 0.5-2 | 1-4 | 1.5-6 | 2-8 | 0.25-1 |

| Component | Tablets % w/w | % w/w |
|---|---|---|
| Coated amphetamine polistirex | | 4.583 |
| Uncoated amphetamine polistirex | | 9.68 |
| Un-complexed amphetamine | | 2.947 |

In certain embodiments, the amphetamine polistirex contains racemic (dl)-amphetamine and (d)-amphetamine in weight ratio of about 0.75 to about 2, to about 1 to about 1.5. Further, in certain embodiments, the ratio of total amphetamines to cation exchange resin is about 1:1 to about 1:6, including ratios therebetween, such as 1:1.5, 1:2, 1:2.5, 1:3, 1:3.5, 1:4, 1:4.5, 1:5, 1:5.5, 1:6, or values therebetween. In other embodiments, other suitable loading amounts of amphetamine onto the resin may be selected.

In certain embodiments, the polistirex is prepared by complexing the (dl)-amphetamine and (d)-amphetamine and the cation exchange resin and granulating the amphetamine polistirex intermediate with a hydrophilic matrix—forming polymer prior to applying the coating. In certain embodiments, the coating is applied in an amount of about 15% w/w to about 40% coating weight gain, or about 20% w/w, or about 25% w/w, or about 30% w/w, or about 35% w/w, or about 40% w/w coating weight gain.

In certain embodiments, the tablets may be scored. For example, a 5 mg tablet may be scored to provide a 2.5 mg dose. However, regardless of scoring, the tablets may be chewed, dissolved, or swallowed whole by the patient.

Suitably, a chewable tablet of the invention is prepared as a single uniform solid blend. A typical manufacturing process for making a chewable tablet generally involves blending of the desired ingredients to form a uniform distribution of the coated amphetamine—cation exchange resin complex, the uncoated amphetamine—cation exchange complex, the uncomplexed amphetamine, and the excipients. If desired, a blend of the amphetamine components may be formed prior to blending into the excipient. The blend is then compressed into a single layer using standard methods and tablet presses such as well-known to those skilled in the art (e.g., Kilian, Fette, Korsch, Elizabeth, Sejong, Kikusui, SMI, Colton, Stok, and Manesty, amongst others.)

In one embodiment, a chewable tablet is produced in a round shape, caplet or capsule shape, optionally with a single bisect (a single scoring at the mid-line which facilitates splitting the tablet into halves). However, other shapes may be readily selected, including, e.g., a standard round shape, a flat faced shape, oval, bullet, square, triangle, diamond, pentagon, octagon, amongst others. Optionally, one or more of these tablet shapes may be provided with a quadrisect, i.e., two perpendicular scores which facilitate splitting the tablet into quarters.

Optionally, the chewable tablet may have one or more sealant or top coating which does not function to modify or extend the release of the amphetamine but which provides moisture barrier, of a color coating or other visual appeal. For example, such a coating may provide a "shine" to the tablet, enhance palatability, serve as an identifying color for the tablet, or other purposes. Such coatings are available commercially, e.g., from Colorcon or other suppliers. Typically, such a coating is composed of hydroxypropyl methylcellulose (HPMC) or polyvinylalcohol and is present in an amount of about 1% w/w to about 20% w/w, or about 2% w/w to about 10% w/w of the total tablet weight.

Suitably, the amphetamine extended release tablets can be scored without affecting the extended release profile. Thus, the oral dose is readily titrated, i.e., split in half, in order to readily and accurately deliver half the dose of the finished tablet. In one embodiment, a titratable, amphetamine chewable tablet of Example 2, and compositions bioequivalent thereto, are encompassed by the invention.

The finished compositions may be stored in glass or high density polyethylene (HDPE) bottles with or without a heat induced sealed (HIS) bottle. The bottle may also contain a desiccant. Alternatively, the tablets may be packaged into blister packs using standard methods well-known to those skilled in the art.

An in vitro dissolution test determines whether chewable tablets disintegrate within a prescribed time when placed in a dissolution media under prescribed experimental conditions. Disintegration is defined as the state in which no residue of the tablet, except fragments of undissolved coating, remains on the screen of the test apparatus or, if any other residue remains, it consists of a soft mass having no palpably firm, unmoistened core.

Examples of methods for in vitro testing of the compositions of the invention have been described, e.g., by the World Health Organization (WHO) International Pharmacopoeia, (www.who.int/medicines/publications/pharmacopoeia/). An example of a suitable disintegration apparatus is described as follows. The apparatus consists of a circular basket-rack assembly, a suitable vessel for the immersion fluid (such as a 1-litre beaker), a thermostatic arrangement for maintaining the fluid at the required temperature (normally 37±2° C.), and a device for raising and lowering the basket-rack in the immersion fluid at a constant frequency of 28-32 cycles/min through a distance of 50-60 mm. The basket-rack assembly consists of six open-ended cylindrical glass tubes and a rack for holding them in a vertical position. The tubes are 75-80 mm long, and have an inside diameter of about 21.5 mm and a wall about 2 mm thick. The tubes are held vertically by two superimposed plates, circular in shape and made of transparent plastic material, each about 90 mm in diameter and 6 mm thick, perforated by six holes of a diameter that allows the tubes to be inserted. The holes are equidistant from the center of the plate and equally spaced one from another. A piece of woven gauze, made of stainless steel wire about 0.635 mm in diameter, with a mesh aperture of 2.0 mm is attached to the underside of the lower plate. The upper plastic plate is covered with a stainless steel plate, about 1 mm thick, of a diameter similar to that of the plastic plates. The steel plate is perforated by six holes about 22 mm in diameter, positioned to coincide with those of the upper plastic plate. It is placed over the tubes and consolidates the whole structure. The plates are held rigidly 75-80 mm apart by vertical stainless steel rods at the periphery. A metal rod is fixed to the center of the upper plate. This enables the assembly to be attached to a suitable mechanical device so that it may be lowered and raised. The volume of the fluid in the immersion vessel should be such that, at the highest point of the upward stroke, the wire mesh that forms the bottom of the basket remains at least 25 mm below the surface of the fluid. At the lowest point of the downward stroke, it should descend to not less than 25 mm from the bottom of the vessel. The time required for the upward stroke should be equal to the time required for the downward stroke, and the change in stroke direction should be a smooth transition rather than an abrupt reversal of motion. Where a disc is prescribed in the monograph, the following configuration and dimensions apply: a cylindrical disc 20.7±0.15 mm in diameter and 9.5±0.15 mm thick, made of transparent plastic with a relative density of 1.18 to 1.20. Each disc is pierced by five holes 2 mm in diameter, one in the center and the other four spaced equally on a circle of radius 6 mm from the center of the disc. On the lateral surface of the disc, four equally spaced grooves are cut so that on the upper surface of the disc they are 9.5 mm wide and 2.55 mm deep and, at the lower surface, 1.6 mm square. Different designs of basket-rack assembly may be used, provided that the specifications for the glass tubes and the stainless steel wire gauze are maintained. In vitro dissolution of the amphetamine compositions described herein may be assessed through a variety of methods including, e.g., Food and Drug Administration (FDA)-accepted dissolution tests, including the Basket Method (I) approved for use with an amphetamine chewable tablet, www.accessdata.fda.gov/scripts/cder/dissolution/dsp_SearchResults_Dissolutions.cfm, have been described. The current FDA-approved dissolution test for a prior art amphetamine tablet comprising Amphetamine Aspartate/Amphetamine Sulfate/Dextroamphetamine Saccharate/Dextroamphetamine Sulfate utilizes water and a paddle speed of 100 rpm, at 500 mL, with testing at 10, 20, 30 and 45 minutes; another prior art tablet containing dextroamphetamine sulfate uses the same test and volume, with testing at 10, 20, 30, 45 and 60 minutes. Two extended release capsules involve testing with Basket Method (II), 50 rpm, in a media of dilute HCl (pH 1.1 for first 2 hrs, then add 200 mL of 200 mM Phosphate Buffer and adjust to pH 6.0 for the remainder) and volume of 750 mL for 0-2 hours and after 2 hours 950 mL; with testing at 1, 2, 3, 4, and 4 or 6 hours (amphetamine ER). Other amphetamine products have different dissolution tests and different media. However, since the barrier coated amphetamine—cation exchange complex described herein is not readily soluble in water, the dissolution medium for the previously described tests are is not suitable for testing dissolution of the present tablets at those time frames. Accordingly, a dissolution medium of phosphate buffer described below may be used to assess in vitro dissolution of the amphetamine compositions described herein rather than water.

In one embodiment, an orally administrable extended release amphetamine composition provides for d-amphetamine, following a single dose of the composition as determined following a chewed dose comprising the equivalent to 20 mg total amphetamine: an arithmetic mean $AUC_{0-\infty}$ of about 965 to about 1508 ng-h/mL, a geometric mean $AUC_{0-\infty}$ of about 931 ng-h/mL to about 1455 ng-h/mL h/mL, an arithmetic mean $AUC_{0-2}$ of about 24.8 ng-h/mL to about 38.79 ng-h/mL or a geometric mean $AUC_{0-2}$ of about 22.85 ng-hr/mL to about 35.72 ng-hr/mL, an arithmetic mean $AUC_{0-5}$ of about 138 ng-h/mL to about 216 ng-h/mL or a geometric mean $AUC_{0-5}$ of about 134 ng-hr/mL to about 209 ng-hr/mL, an arithmetic mean $AUC_{5-t}$ 767 ng-hr/mL to about 1199 ng-hr/mL or a geometric mean $AUC_{5-t}$ of about of about 740 ng-h/mL to about 1156 ng-h/mL, an arithmetic mean $C_{max}$ of about 44 ng/mL to about 69 ng/mL, a geometric mean $C_{max}$ of about 43 ng/mL to about 68 ng/mL, or a $T_{max}$ of about 3 hours to about 7 hours.

In one embodiment, an orally administrable extended release amphetamine composition provides one or more of the pharmacokinetic parameters for d-amphetamine, following a single dose of the composition is as determined for a whole swallowed tablet dose comprising the equivalent to 20 mg total amphetamine: an arithmetic $AUC_{0-\infty}$ of about 972 to about 1519 ng-h/mL, a geometric mean $AUC_{0-\infty}$ of about 948 ng-h/mL to about 1481 ng-h/mL h/mL, an arithmetic mean $AUC_{0-2}$ of about 26.30 ng-h/mL to about 41.10 ng-h/mL or a geometric mean $AUC_{0-2}$ of about 24.48 ng-hr/mL to about 38.25 ng-hr/mL, an arithmetic mean $AUC_{0-5}$ of about 141 ng-h/mL to about 220 ng-h/mL or a geometric mean $AUC_{0-5}$ of about 138 ng-hr/mL to about 215 ng-hr/mL, an arithmetic mean $AUC_{5-t}$ of about 768 ng-h/mL to about 1200 ng-h/mL, or a geometric mean $AUC_{5-t}$ of about 749 ng-hr/mL to about 1170 ng-hr/mL, an arithmetic mean $C_{max}$ of about 42 ng/mL to 66 ng/mL, a geometric mean $C_{max}$ of about 42 ng/mL to 66 ng/mL, an arithmetic mean or a Tmax of about 2 hours to about 9 hours.

In one embodiment, an orally administrable extended release amphetamine composition provides, following a single dose of the tablet comprises one or more of the pharmacokinetic parameters for d-amphetamine following dosing an adult under fasted conditions with the tablet comprising the equivalent of 20 mg total amphetamines: for a chewed dose: an arithmetic mean $AUC_{0-\infty}$ of about 1206 ng-h/mL, a geometric mean $AUC_{0-\infty}$ of about 1164 ng-hr/mL, an arithmetic mean $AUC_{0-2}$ of about 31 ng-h/mL, a geometric mean $AUC_{0-2}$ of about 29 ng-hr/mL, an arithmetic mean $AUC_{0-5}$ of about 173 ng-h/mL, a geometric mean $AUC_{0-5}$ of about 167 ng-hr/mL, an arithmetic mean $AUC_{5-t}$ of about 959 ng-h/mL, a geometric mean $AUC_{5-t}$ of about 925 ng-hr/mL, an arithmetic mean $C_{max}$ of about 55 ng/mL, a geometric mean $c_{max}$ of about 54 ng/mL, or a $T_{max}$ of about 5 hours.

In one embodiment, an orally administrable extended release amphetamine composition provides for d-amphetamine, following a single dose of the tablet comprises, for a whole swallowed dose: for a whole swallowed dose: an arithmetic mean $AUC_{0-\infty}$ of about 1215 ng-h/mL, a geometric mean $AUC_{0-\infty}$ of about 1185 ng-hr/mL, an arithmetic mean $AUC_{0-2}$ of about 33 ng-h/mL, a geometric mean $AUC_{0-2}$ of about 31 ng-hr/mL, an arithmetic mean $AUC_{0-5}$ of about 176 ng-h/mL, a geometric mean $AUC_{0-5}$ of about 172 ng-hr/mL, an arithmetic mean $AUC_{5-t}$ of about 960 ng-h/mL, a geometric mean $AUC_{5-t}$ of about 936 ng-hr/mL, an arithmetic mean $C_{max}$ of about 53 ng/mL, a geometric mean $C_{max}$ of about 53 ng/mL, or a $T_{max}$ of about 5 hours.

In one embodiment, an orally administrable extended release amphetamine composition provides, following a single dose of the tablet, one or more of the pharmacokinetic parameters for l-amphetamine following dosing an adult under fasted conditions with the tablet comprising the equivalent of 20 mg total amphetamines: as determined following a chewed dose: as determined following a chewed dose: an arithmetic mean $AUC_{0-\infty}$ of about 378 to about 591 ng-h/mL, a geometric mean $AUC_{0-\infty}$ of about 362 ng-h/mL to about 566 ng-h/mL, an arithmetic mean $AUC_{0-2}$ of about 7.57 ng-h/mL to about 11.85 ng-h/mL or a geometric mean $AUC_{0-2}$ of about 6.97 ng-hr/mL to about 10.89 ng-hr/mL, an arithmetic mean $AUC_{0-5}$ of about 43 ng-h/mL to about 68 ng-h/mL, a geometric mean $AUC_{0-5}$ of about 42 ng-hr/mL to about 65 ng-hr/mL, an arithmetic mean $AUC_{5-t}$ 292 ng-hr/mL to about 456 ng-hr/mL, a geometric mean $AUC_{5-t}$ of about 280 ng-h/mL to about 438 ng-h/mL, an arithmetic mean $C_{max}$ of about 13.6 ng/mL to about 21.25 ng/mL, a geometric mean $C_{max}$ of about 3.6 ng/mL to about 21.25 ng/mL, or a $T_{max}$ of about 3 hours to about 7 hours.

In one embodiment, an orally administrable extended release amphetamine composition provides, following a single dose of the tablet, one or more of the pharmacokinetic parameters for l-amphetamine following a whole swallowed dose: an arithmetic mean $AUC_{0-\infty}$ of about 385 ng-h/mL to about 601 ng-h/mL, a geometric mean $AUC_{0-\infty}$ of about 373 ng-h/mL to about 583 ng-h/mL h/mL, an arithmetic mean $AUC_{0-2}$ of about 8.09 ng-h/mL to about 12.64 ng-h/mL or a geometric mean $AUC_{0-2}$ of about 7.49 ng-hr/mL to about 11.71 ng-hr/mL, an arithmetic mean $AUC_{0-5}$ of about 44 ng-h/mL to about 69 ng-h/mL, a geometric mean $AUC_{0-5}$ of about 43 ng-hr/mL to about 68 ng-hr/mL, an arithmetic mean $AUC_{5-t}$ of about 294 ng-hr/mL to about 459 ng-hr/mL, a geometric mean $AUC_{5-t}$ of about 286 ng-h/mL to about 446 ng-h/mL, an arithmetic mean $C_{max}$ of about 13.6 ng/mL to about 21.25 ng/mL, a geometric mean $C_{max}$ of about 3.6 ng/mL to about 21.25 ng/mL, or a $T_{max}$ of about 2 hours to about 9 hours.

In one embodiment, an orally administrable extended release amphetamine composition provides, following a single dose of the tablet, one or more of the pharmacokinetic parameters for l-amphetamine following dosing an adult under fasted conditions with the tablet comprising 20 mg total amphetamines: for a chewed dose: an arithmetic mean $AUC_{0-\infty}$ of about 473 ng-h/mL, a geometric mean $AUC_{0-\infty}$ of about 453 ng-hr/mL, an arithmetic mean $AUC_{0-5}$ of about 54 ng-h/mL, a geometric mean $AUC_{0-5}$ of about 52 ng-hr/mL, an arithmetic mean $AUC_{5-t}$ of about 365 ng-h/mL, a geometric mean $AUC_{5-t}$ of about 350 ng-hr/mL, an arithmetic mean $C_{max}$ of about 17 ng/mL, a geometric mean $C_{max}$ of about 17 ng/mL, or a median $T_{max}$ of about 5 hours;

In one embodiment, an orally administrable extended release amphetamine composition provides, following a single dose of the composition, for a whole swallowed dose: an arithmetic mean $AUC_{0-\infty}$ of about 481 ng-h/mL, a geometric mean $AUC_{0-\infty}$ of about 466 ng-h/mL, an arithmetic mean $AUC_{0-5}$ of about 55 ng-h/mL, a geometric mean $AUC_{0-5}$ of about 54 ng-hr/mL, an arithmetic mean $AUC_{5-t}$ of about 367 ng-h/mL, a geometric mean $AUC_{5-t}$ of about 357 ng-hr/mL, an arithmetic mean $c_{max}$ of about 17 ng/mL, a geometric mean $c_{max}$ of about 17 ng/mL, or a median $T_{max}$ of about 5 hours.

In certain embodiments, the extended release amphetamine solid composition provides a plasma pharmacokinetic profile for d-amphetamine which is about 80% to about 125% of one or more of one or more: a geometric mean $AUC_t$ of about 821 ng-h/mL, a geometric mean $AUC_{inf}$ of about 1013 ng-h/mL, a geometric mean $C_{max}$ of about 53 ng/mL, a geometric mean $T_{max}$ of about 3.85, an arithmetic mean $AUC_t$ of about 857 ng-h/mL, an arithmetic mean about $AUC_{inf}$ of about 1061 ng-h/mL, an arithmetic mean $C_{max}$ of about 55 ng/mL, or an arithmetic mean $T_{max}$ of about 4, as measured in children 6-12 years old under fasting conditions following dosing with the composition having the equivalent of 20 mg of amphetamine base; an arithmetic mean $AUC_{0-4}$ of about 144 ng-h/mL, an arithmetic mean $AUC_{4-t}$ of about 1000 ng-h/mL, an arithmetic mean $AUC_{0-5}$ of about 196 ng-h/mL, an arithmetic mean $AUC_{5-t}$ of about 948 ng-h/mL, a geometric mean $AUC_{0-4}$ of about 139 ng-h/mL, a geometric mean $AUC_{4-t}$ of about 977 ng-h/mL, a geometric mean $AUC_{0-5}$ of about 191 ng-h/mL, or a geometric mean $AUC_{5-t}$ of about 926 ng-h/mL, as measured in children 6-12 years old under fasting conditions following dosing with the composition having the equivalent of 20 mg of amphetamine base. In certain embodiments, the pharmacokinetic profile for d-amphetamine is about 90% to about 110% of one or more of the parameters. The percentages are calculated as described herein, using a 90% confidence interval.

In certain embodiments, the extended release amphetamine solid composition provides a plasma pharmacokinetic profile for l-amphetamine which is about 80% to about 125% of one or more of one or more: a geometric mean $AUC_t$ of about 274 ng-h/mL, a geometric mean about AUCinf of about 362 ng-h/mL, a geometric mean $c_{max}$ of about 16 ng/mL, a geometric mean $T_{max}$ of about 4.5, an arithmetic mean $AUC_t$ of about 286 ng-h/mL, an arithmetic mean about $AUC_{inf}$ of about 380 ng-h/mL, an arithmetic mean $C_{max}$ of about 17 ng/mL, or an arithmetic mean $T_{max}$ of about 4.5, as measured in children 6-12 years old under fasting conditions following dosing with the composition having the equivalent of 20 mg of amphetamine base; an arithmetic mean $AUC_{0-4}$ of about 45 ng-h/mL, an arithmetic mean $AUC_{4-t}$ of about 380 ng-h/mL, an arithmetic mean $AUC_{0-5}$ of about 62 ng-h/mL, an arithmetic mean $AUC_{5-t}$ of about 363 ng-h/mL, a geometric mean $AUC_{0-4}$ of about 44 ng-h/mL, a geometric mean $AUC_{4-t}$ of about 370 ng-h/mL, a geometric mean $AUC_{0-5}$ of about 60 ng-h/mL, or a geometric mean $AUC_{5-t}$ of about 354 ng-h/mL, as measured in adults under fasting conditions following dosing with the composition having the equivalent of 20 mg of amphetamine base. The percentages are calculated as described herein, using a 90% confidence interval.

In certain embodiments, the composition is a chewable tablet. In still other embodiments, the composition is orally dissolving or dispersible tablet. In certain embodiments, the composition is a chewable tablet with is also orally dissolving, disintegrating, and/or dispersible.

The chewable tablet may contain a dose of about 2.5 mg to about 20 mg total amphetamines based on the amount of free amphetamine base, which is a mixture of d-amphetamine and l-amphetamine. In certain embodiments, the ratio of d-amphetamine to l-amphetamine is about 3 parts w/w d-amphetamine to about 1 part w/w l-amphetamine. This ratio may be supplied by separately combining racemic (d,l)-amphetamine and d-amphetamine, or by separately combining racemic d-amphetamine and l-amphetamine.

The tablet (e.g., dosage unit or dosage form) may contain about 2.5 mg amphetamines, about 5 mg amphetamine, about 15 mg amphetamines, or about 20 mg amphetamines. In certain embodiments, the tablet may be scored to allow for easy titration of the dose.

In one embodiment, the extended release amphetamine composition contains, based on the total (free base) amphetamine in the composition, at least about 15% to about 35% w/w of the amphetamine is provided by modified release component, at least about 10% to about 30% w/w of the amphetamine is provided by immediate release component comprising unbound amphetamine, and at least 40% to about 70% w/w of the amphetamine is provided by immediate release component comprising amphetamine—ion exchange resin complex.

In one embodiment, the composition is an extended release tablet, wherein based on the weight of the total amphetamines as calculated on the basis of the free amphetamine bases, the modified release component. In one embodiment, each of the three components provides a ratio of d-amphetamine to l-amphetamine of about 3:about 1. In a further embodiment, the modified release component comprises 40% or less of the total amphetamines and the immediate release component comprising the amphetamine—ion exchange resin complex provides at least 60% of the total amphetamines.

In one embodiment, the composition contains only two counterions contributed by the amphetamine salts. In certain embodiments, the composition contains only one counterion contributed by the amphetamine salts.

In one embodiment, the extended release tablet has a therapeutic effect for attention deficit hyperactivity disorder with an onset at least as early as 1 hour and continuing through at least about 13 hours, in patients following administration of a dose about 20 mg total amphetamines (based on the weight of the free base form of the amphetamines). However, other concentrations, e.g., of about 2.5 mg, 5 mg, 10 mg, 15 mg, or 20 mg, may be readily selected. In certain embodiments, the extended release amphetamine composition having the pharmacokinetic profile recited above is a chewable tablet. In one embodiment, the tablet is characterized by also being capable of functioning as an orally dissolving tablet.

In one embodiment, of the total amphetamines in the chewable tablet (based on free base of amphetamines), the modified release component contains about 15% to about 30%, or about 20% of the amphetamines, the immediate release component comprising the amphetamine—cation exchange resin complex provides about 50% to about 70%, or about 60% of the total amphetamines in the tablet, and the total unbound amphetamine is in the range of about 5% to about 25%, or about 20%, of the amphetamines. These tablets may be formulated as described previously in doses of 2.5, 5, 10, 15, 17.5 and/or 20 mg equivalent to amphetamine (based on free base weight). Other dose amounts may be selected.

An amphetamine extended release composition as described herein may be orally administered to a patient having a disorder treatable by amphetamine. These include disorders for which regulatory approval has been granted in the US or other jurisdiction in which the drug is being administered and which requires regulatory approval. For example, amphetamine is currently approved for treatment of Attention Deficit Hyperactivity Disorder (ADHD) and narcolepsy. Amphetamine has also been described in patent applications and in the literature as being useful for treatment of other conditions or disorders including, but are not limited to, behavioral disorders, including Attention Deficit Disorder, treatment-resistant cases of lethargy, depression, obesity, weight loss, nasal congestion, neural insult, obesity, and rarely other psychiatric disorders such as obsessive-compulsive disorder, specific dyslexias, brain dysfunction, and cognitive decline. Berman et al, cited above.

Thus, a method of treating one or more of the above disorders for a period of at least eight hours, at least twelve hours, at least thirteen hours, or longer, by administering an amphetamine extended release composition is described herein. A composition of the invention is formulated to deliver amphetamine is, most desirably, in dosages ranging from about 1 mg up to about 20 mg per day, preferably from about 2.5 mg to about 20 mg per day, or in about 2.5 mg, 5 mg, 10 mg, 15 mg, 17.5 mg, or 20 mg doses [based on equivalence to amphetamine free base] although variations will necessarily occur depending upon the weight and condition of the subject being treated and the particular route of administration chosen. Variations may nevertheless occur depending upon the weight and condition of the persons being treated and their individual responses to said medicament.

As described herein, the amphetamine extended release compositions of the invention are dosed orally once per day in the morning, e.g, before 11 am. Optionally, smaller doses may be delivered in the morning and at intervals during the day. Other variations may be selected depending upon the patient.

The following examples are illustrative only and are not intended to be a limitation on the present invention.

EXAMPLES

The weight percentages provided in the following examples are based on the weight percentage of the total amount of the active drug in the dose using the weight of the free base equivalent, i.e., weight on the active drug calculated or measured without the weight of the coating, matrix polymer, polistirex, counterion, or hydrate form of the compound.

Example A: Uncoated ((d, dl-) Amphetamine—Cation Exchange Resin Complex

| Uncoated (d, dl) Amphetamine - Cation Exchange Resin Complex | |
| --- | --- |
| Ingredients | Quantity |
| Sodium Polystyrene Sulfonate (Amberlite IRP69 ®) Cation Exchange Resin | 12000 g |
| (dl) Amphetamine Sulfate | 1440 g |
| (d)-Amphetamine Sulfate | 1560 g |
| Purified Water | 70 L |

The Drug-Resin Complex is prepared by first adding 70 L of Purified Water into the process vessel, following which (dl)-Amphetamine Sulfate and (d)—Amphetamine Sulfate are dissolved by continuous mixing. Sodium Polystyrene Sulfonate is dispersed with continuous mixing and the mixing is continued for 60 minutes. Water is removed by filtration process followed by rinsing twice using purified water (40 L). Wet resin complex is then dried until moisture content is between 3% to 7%. Dried drug-resin complex is passed through a 40 mesh screen using the CO-MIL. This is the Uncoated (d, dl) amphetamine—cation exchanger resin complex, which is used directly in the compositions described beginning with Example 1 and for preparing the Uncoated (d, dl) amphetamine—cation exchanger resin complex—matrix, which is subsequently coated.

Example B: Uncoated ((d, dl-) Amphetamine—Cation Exchange Resin Complex—Matrix

| (d, dl) Amphetamine - Cation Exchange Resin - Matrix | |
| --- | --- |
| Ingredients | Quantity |
| Uncoated (d, dl) Amphetamine - Cation Exchange Resin Complex | 10000 g |
| Povidone (Kollidon ® 30D) | 500 g |
| Purified water | 3500 g |

In a separate container Povidone is dissolved in 3500 g of Purified Water (Povidone solution). Uncoated (d, dl) Amphetamine—cation exchange resin complex prepared as described in Example A is treated with Povidone solution with continuous mixing to form a uniform mass. Wet mass is dried until the moisture content is between 15-25%. Semi-dried material is then milled using CO-MIL brand mill fitted with 40 mesh screen. Milled material is further dried until moisture content is between 3-7%. Dried material is passed through a CO-MIL fitted with a 40 mesh screen. This is the (d, dl) amphetamine—cation exchange resin complex—matrix.

Example C: Barrier Coated ((d, dl-) Amphetamine—Cation Exchange Resin Complex—Matrix, with Polyvinylacetate—Plasticizer Barrier Coating 1. Coated (d, dl) Amphetamine—Cation Exchange Resin with 30% Weight Gain

| Coated (d,dl) Amphetamine - Cation Exchange resin Complex - matrix | |
| --- | --- |
| Ingredients | Quantity |
| (d, dl) Amphetamine - Cation Exchange Resin Complex - Matrix | 2500 g |
| Polyvinyl Acetate Dispersion** (Kollicoat ® SR30D) | 3500 g |
| Triacetin | 52.5 g |
| Purified Water | 1960 g |

Removed during processing
**30% w/w aqueous dispersion

The Coated (d, dl) Amphetamine—cation exchange resin complex—matrix is prepared as follows. The coating solution is prepared by mixing Triacetin, Purified Water and Polyvinyl Acetate dispersion in a separate container. The coating process is performed in a fluid bed processor equipped with Wurster column by applying coating solution on to (d, dl) Amphetamine—cation exchange resin complex—matrix as prepared in Example B, that results in 30% weight gain. The Coated (d, dl) Amphetamine—Cation Exchange Resin complex—matrix is placed in the hot air oven at 60° C. for 5 hours. The Coated (d, dl) Amphetamine—Cation exchange resin complex—Matrix is again passed through Sieve No. 40 mesh screen. This is the Coated (d, dl) Amphetamine—Cation Exchange Resin Complex—Matrix.

2. Coated (d, dl) Amphetamine—Cation Exchange Resin with 40% Weight Gain

Coated (d, dl) Amphetamine—cation exchange resin complex is prepared as follows. The coating solution is prepared by mixing Triacetin, Purified Water and Polyvinylacetate dispersion in a separate container. The coating process is performed in a fluid bed processor equipped with Wurster column by applying adequate quantity of the coating solution on to uncoated (d, dl) Amphetamine—cation exchange resin complex as prepared in Example B, that results in 40% weight gain. The Coated (d, dl) Amphetamine—Cation Exchange Resin complex is placed in the hot air oven at 60° C. for 5 hours. The Coated (d, dl) Amphetamine—Cation exchange resin complex is passed through Sieve No. 40 mesh screen. This is the Coated (d, dl) Amphetamine—Cation Exchange Resin.

| Coated (d,dl) Amphetamine - Cation Exchange resin Complex - matrix | |
|---|---|
| Ingredients | Quantity |
| (d, dl) Amphetamine - Cation Exchange Resin Complex - Matrix | 600 g |
| Polyvinyl Acetate Dispersion** (Kollicoat ® SR30D) | 1015 g |
| Triacetin | 15 g |
| Purified Water | 570 g |

3. Coated (d, dl) Amphetamine—Cation Exchange Resin with 50% Weight Gain

Coated (d, dl) Amphetamine—cation exchange resin complex with no matrix is prepared as follows. The coating solution is prepared by mixing Triacetin, Purified Water and Polyvinyl Acetate dispersion in a separate container. The coating process is performed in a fluid bed processor equipped with Wurster column by applying adequate quantity of the coating solution on to uncoated (d, dl) Amphetamine—cation exchange resin complex as prepared in Example B, that results in 50% weight gain. The Coated (d, dl) Amphetamine—Cation Exchange Resin complex is placed in the hot air oven at 60° C. for 5 hours. The Coated (d, dl) Amphetamine—Cation exchange resin complex is passed through Sieve No. 40 mesh screen. This is the Coated (d, dl) Amphetamine—Cation Exchange Resin.

| Coated (d,dl) Amphetamine - Cation Exchange resin Complex - matrix | |
|---|---|
| Ingredients | Quantity |
| (d, dl) Amphetamine - Cation Exchange Resin Complex - Matrix | 600 g |
| Polyvinyl Acetate Dispersion** (Kollicoat ® SR30D) | 1015 g |
| Triacetin | 15 g |
| Purified Water | 570 g |

Example D: Barrier Coated ((d, dl-) Amphetamine—Cation Exchange Resin Complex—Matrix, with Ethylcellulose Barrier Coating 1. Aqueous Ethylcellulose

| Coated (d,dl) Amphetamine - Cation Exchange resin Complex - matrix | |
|---|---|
| Ingredients | Quantity |
| (d, dl) Amphetamine - Cation Exchange Resin Complex - Matrix | 2500 g |
| Ethylcellulose (Surerelease ®) | 3500 g |
| Triacetin | 52.5 g |
| Purified Water | 1960 g |

Coated (d, dl) Amphetamine—cation exchange resin complex is prepared as follows. The coating solution is prepared by mixing Triacetin, Purified Water and Ethylcellulose dispersion in a separate container. The coating process is performed in a fluid bed processor equipped with Wurster column by applying coating solution on to uncoated (d, dl) Amphetamine—cation exchange resin complex as prepared in Example B, that results in 30% weight gain. The Coated (d, dl) Amphetamine—Cation Exchange Resin complex is placed in the hot air oven at 60° C. for 5 hours. The Coated (d, dl) Amphetamine—Cation exchange resin complex is passed through Sieve No. 40 mesh screen. This is the Coated (d, dl) Amphetamine—Cation Exchange Resin.

2. Solvent-Based Ethylcellulose

| Coated (d,dl) Amphetamine - Cation Exchange resin Complex - matrix | |
|---|---|
| Ingredients | Quantity |
| (d, dl) Amphetamine - Cation Exchange Resin Complex - Matrix | 2500 g |
| Ethylcellulose (Ethocel ®) | 3500 g |
| Triacetin | 52.5 g |
| Ethanol/water | 1960 g |

Coated (d, dl) Amphetamine—cation exchange resin complex is prepared as follows. The coating solution is prepared by mixing Triacetin, Purified Water and Ethylcellulose solution in a separate container. The coating process is performed in a fluid bed processor equipped with Wurster column by applying coating solution on to uncoated (d, dl) Amphetamine—cation exchange resin complex as prepared in Example B, that results in 30% weight gain. The Coated (d, dl) Amphetamine—Cation Exchange Resin complex is placed in the hot air oven at 60° C. for 5 hours. The Coated (d, dl) Amphetamine—Cation exchange resin complex is passed through Sieve No. 40 mesh screen. This is the Coated (d, dl) Amphetamine—Cation Exchange Resin.

Example E: Barrier Coated ((d, dl-) Amphetamine—Cation Exchange Resin Complex—Matrix, with pH-independent Eudragit® RL30D Polyacrylic Aqueous Dispersion—Barrier Coating

| Ingredients | Quantity |
|---|---|
| Coated (d, dl) Amphetamine-Cation Exchange resin Complex-matrix | |
| (d, dl) Amphetamine-Cation Exchange Resin Complex-Matrix | 2500 g |
| Eudragit ® RL30D Polyacrylic aqueous dispersion | 3500 g |
| Triacetin | 52.5 g |
| Purified Water | 1960 g |

Coated (d, dl) Amphetamine—cation exchange resin complex is prepared as follows. The coating solution is prepared by mixing Triacetin, Purified Water and Eudragit® RL30D Polyacrylic aqueous dispersion in a separate container. The coating process is performed in a fluid bed processor equipped with Wurster column by applying coating solution on to uncoated (d, dl) Amphetamine—cation exchange resin complex as prepared in Example B, that results in 30% weight gain. The Coated (d, dl) Amphetamine—Cation Exchange Resin complex is placed in the hot air oven at 60° C. for 5 hours. The Coated (d, dl) Amphetamine—Cation exchange resin complex is passed through Sieve No. 40 mesh screen. This is the Coated (d, dl) Amphetamine—Cation Exchange Resin.

Example F: Barrier Coated ((d, dl-) Amphetamine—Cation Exchange Resin Complex—Matrix, with pH-independent Cellulose Acetate—Barrier Coating 1. The Coated (d, dl) Amphetamine—Cation Exchange Resin Complex Matrix.

| Ingredients | Quantity |
|---|---|
| Coated (d, dl) Amphetamine-Cation Exchange resin Complex-matrix | |
| (d, dl) Amphetamine-Cation Exchange Resin Complex-Matrix | 2500 g |
| Cellulose Acetate (CA-398-10 NF/EP) | 850 g |
| Polyethylene Glycol | 200 g |
| Triacetin | 52.5 g |
| Acetone/Water (80/20 wt %) ** | 2000 g |

** Removed during processing

The Coated (d, dl) Amphetamine—cation exchange resin complex matrix is prepared as follows. The coating solution is prepared by mixing the cellulose acetate and polyethylene glycol in acetone/water until completely dissolved, following by mixing with triacetin in a separate container. The coating process is performed in a fluid bed processor equipped with Wurster column by applying coating solution on to (d, dl) Amphetamine—cation exchange resin complex—matrix as prepared in Example B, that results in 25% weight gain. The Coated (d, dl) Amphetamine—Cation Exchange Resin complex—matrix is placed in the hot air oven at 60° C. for 5 hours. The Coated (d, dl) Amphetamine—Cation exchange resin complex—matrix is again passed through Sieve No. 40 mesh screen. This is the Coated (d, dl) Amphetamine—Cation Exchange Resin Complex—Matrix.

2. The Coated (d, dl) Amphetamine—Cation Exchange Resin Complex

| Ingredients | Quantity |
|---|---|
| Coated (d, dl) Amphetamine-Cation Exchange resin Complex | |
| (d, dl) Amphetamine-Cation Exchange Resin Complex | 2500 g |
| Cellulose Acetate (CA-398-10 NF/EP) | 850 g |
| Polyethylene Glycol | 200 g |
| Triacetin | 52.5 g |
| Acetone/Water (80/20%) ** | 2000 g |

The Coated (d, dl) Amphetamine—cation exchange resin complex is prepared as follows. The coating solution is prepared by mixing the cellulose acetate and polyethylene glycol in acetone/water until completely dissolved, following by mixing with triacetin in a separate container. The coating process is performed in a fluid bed processor equipped with Wurster column by applying coating solution on to (d, dl) Amphetamine—cation exchange resin complex as prepared in Example A, that results in 25% weight gain. The Coated (d, dl) Amphetamine—Cation Exchange Resin complex is placed in the hot air oven at 60° C. for 5 hours. The Coated (d, dl) Amphetamine—Cation exchange resin complex is again passed through Sieve No. 40 mesh screen. This is the Coated (d, dl) Amphetamine—Cation Exchange Resin Complex.

In the following examples, chewable tablets and methods of making same are illustrated.

Example 1: Amphetamine Extended Release (ER) Chewable Tablets Equivalent to 20 mg Amphetamine Free Base, with Polyvinylacetate Barrier Coated Modified Release Component (30/50/20—Coated/Uncoated/API)

In the following study, a polyvinylacetate—plasticizer barrier coating of Example C1 (30% weight gain) is selected for the Barrier Coated Amphetamine—cation exchange resin complex—matrix.

| Ingredients | % w/w |
|---|---|
| Barrier Coated Amphetamine-cation exchange resin complex-matrix | 6.881 |
| Uncoated Amphetamine-cation exchange resin complex | 7.998 |
| Dextroamphetamine Sulfate, USP | 0.356 |
| Amphetamine Aspartate Monohydrate | 0.511 |
| Mannitol, USP | 53.054 |
| Talc, USP | 1.0 |
| Xanthan gum, NF (Gumixan ™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid ® 244FP) | 0.2 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender. Mix the powder blend for 15 minutes. Weigh Magnesium Stearate and pass through #40 mesh screen. Add the screened material into 'V'-Blender. Mix this powder blend for 10 minutes. The material from the Blender is unloaded and compressed into tablets by adjusting the appropriate tablet weight and hardness.

Example 2—Amphetamine Extended Release (ER) Chewable Tablets Equivalent to 20 mg Amphetamine Free Base, with Ethylcellulose Barrier Coated Modified Release Component (30/50/20—Coated/Uncoated/API)

In the following study, an aqueous ethylcellulose barrier coating of Example D1 (30% weight gain) is selected for the Barrier Coated Amphetamine—cation exchange resin complex—matrix. In other embodiments, the solvent-based ethylcellulose barrier coating of example D2 is selected for the Barrier Coated Amphetamine—cation exchange resin complex—matrix.

| Ingredients | % w/w |
| --- | --- |
| Barrier Coated Amphetamine-cation exchange resin complex-matrix | 6.881 |
| Uncoated Amphetamine-cation exchange resin complex | 7.998 |
| Dextroamphetamine Sulfate, USP | 0.356 |
| Amphetamine Aspartate Monohydrate | 0.511 |
| Mannitol, USP | 53.054 |
| Talc, USP | 1.0 |
| Xanthan gum, NF (Gumixan ™ K) | 0.5 |
| Crospovidone, NF (Kollidon ® CL), Type A | 12 |
| Microcrystalline cellulose and Guargum (Avicel ® CE 15) | 15 |
| Sucralose, NF | 1.5 |
| Bubblegum Flavor | 0.5 |
| Silicon dioxide, NF (Syloid ® 244FP) | 0.2 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender. Mix the powder blend for 15 minutes. Weigh Magnesium Stearate and pass through #40 mesh screen. Add the screened material into 'V'-Blender. Mix this powder blend for 10 minutes. The material from the Blender is unloaded and compressed into tablets by adjusting the appropriate tablet weight and hardness.

Example 3—Amphetamine Extended Release (ER) Chewable Tablets Equivalent to 20 mg Amphetamine Free Base, with Cellulose Acetate Barrier Coated Modified Release Component (30/50/20—Coated/Uncoated/API)

In the following study, a cellulose acetate barrier coating of Example F1 (25% weight gain) is selected for the Barrier Coated Amphetamine—cation exchange resin complex—matrix. In alternative embodiments, the cellulose acetate barrier coating of Example F2 is selected for the Barrier coated Amphetamine—cation exchange resin complex (coating over AMP—cation exchange resin complex of Example A).

| Ingredients | % w/w |
| --- | --- |
| Barrier Coated Amphetamine-cation exchange resin complex or complex-matrix | 6.881 |
| Uncoated Amphetamine-cation exchange resin complex | 7.998 |
| Dextroamphetamine Sulfate, USP | 0.356 |
| Amphetamine Aspartate Monohydrate | 0.511 |
| Mannitol, USP | 53.054 |
| Talc, USP | 1.0 |
| Xanthan gum, NF (Gumixan ™ K) | 0.5 |
| Crospovidone, NF (Kollidon ® CL), Type A | 12 |
| Microcrystalline cellulose and Guargum (Avicel ® CE 15) | 15 |
| Sucralose, NF | 1.5 |
| Bubblegum Flavor | 0.5 |
| Silicon dioxide, NF (Syloid ® 244FP) | 0.2 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender. Mix the powder blend for 15 minutes. Weigh Magnesium Stearate and pass through #40 mesh screen. Add the screened material into 'V'-Blender. Mix this powder blend for 10 minutes. The material from the Blender is unloaded and compressed into tablets by adjusting the appropriate tablet weight and hardness.

Example 4—Amphetamine Extended Release (ER) Chewable Tablets Equivalent to 20 mg Amphetamine Free Base, with Eudragit Barrier Coated Modified Release Component (30/50/20—Coated/Uncoated/API)

In the following study, an acrylate based barrier coating of Example E (30% weight gain) is selected for the Barrier Coated Amphetamine—cation exchange resin complex—matrix.

| Ingredients | % w/w |
| --- | --- |
| Barrier Coated Amphetamine-cation exchange resin complex | 6.881 |
| Uncoated Amphetamine-cation exchange resin complex | 7.998 |
| Dextroamphetamine Sulfate, USP | 0.356 |
| Amphetamine Aspartate Monohydrate | 0.511 |
| Mannitol, USP | 53.054 |
| Talc, USP | 1.0 |
| Xanthan gum, NF (Gumixan ™ K) | 0.5 |
| Crospovidone, NF (Kollidon ® CL), Type A | 12 |
| Microcrystalline cellulose and Guargum (Avicel ® CE 15) | 15 |
| Sucralose, NF | 1.5 |
| Bubblegum Flavor | 0.5 |

| Ingredients | % w/w |
| --- | --- |
| Silicon dioxide, NF (Syloid ® 244FP) | 0.2 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix of Example E, Dextroamphetamine Sulfate and Amphetamine Aspartate Monohydrate are weighed and passed through a #40 mesh screen. The screened material is added into a 'V'-Blender Mix the powder blend for 15 minutes. Weigh Magnesium Stearate and pass through #40 mesh screen. Add the screened material into 'V'-Blender. Mix this powder blend for 10 minutes. The material from the Blender is unloaded and compressed into tablets by adjusting the appropriate tablet weight and hardness.

Example 5—Amphetamine Extended Release (ER) Chewable Tablets Equivalent to 20 mg Amphetamine Free Base In the following study, a polyvinylacetate barrier coating of Example C1 (30% weight gain) is selected for the Barrier Coated Amphetamine—cation exchange resin complex—matrix.

| Ingredients | % w/w |
| --- | --- |
| Barrier Coated Amphetamine-cation exchange resin complex-matrix | 6.881 |
| Uncoated Amphetamine-cation exchange resin complex | 7.998 |
| Dextroamphetamine Saccharate | 0.356 |
| Amphetamine sulfate | 0.511 |
| Mannitol, USP | 53.054 |
| Talc, USP | 1.0 |
| Xanthan gum, NF (Gumixan™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid 244FP) | 0.2 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex, Coated Amphetamine—cation exchange resin complex—matrix, Dextroamphetamine Saccharate and Amphetamine Sulfate are weighed and passed through a #40 mesh screen. The screened material is added into a 'V'-Blender. Mix the powder blend for 15 minutes. Weigh Magnesium Stearate and pass through #40 mesh screen. Add the screened material into 'V'-Blender. Mix this powder blend for 10 minutes. The material from the Blender is unloaded and compressed into tablets by adjusting the appropriate tablet weight and hardness.

Example 6—Amphetamine Extended Release (ER) Chewable Tablets Equivalent to 20 mg Amphetamine Free Base 20/60/20—Coated/Uncoated/API In the following study, an ethylcellulose barrier coating of Example C1 (30% weight gain) is selected for the Barrier Coated Amphetamine—cation exchange resin complex—matrix.

| Ingredients | % w/w |
| --- | --- |
| Barrier Coated Amphetamine-cation exchange resin complex-matrix | 4.583 |
| Uncoated Amphetamine-cation exchange resin complex | 9.68 |
| Dextroamphetamine Sulfate, USP | 0.356 |
| Amphetamine Aspartate Monohydrate | 0.511 |
| Mannitol, USP | 53.67 |
| Xanthan gum, NF (Gumixan™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid ® 244FP) | 0.2 |
| Talc, USP | 1.0 |
| Magnesium stearate, NF | 0.5 |
| Total | 100.0 |

The extended release chewable tablets containing amphetamines are prepared as follows. Weigh the mannitol and microcrystalline cellulose and guar gum (Avicel® CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender. Mix the powder blend for 25 minutes. Weigh Magnesium Stearate and pass through #40 mesh screen. Add the screened material into 'V'-Blender. Mix this powder blend for 5 minutes. The material from the Blender is unloaded and compressed into tablets by adjusting the appropriate tablet weight and hardness.

Example 7—Amphetamine Extended Release (ER) Chewable Tablets Equivalent to 20 mg Amphetamine Free Base In the following study, an ethylcellulose barrier coating of Example D1 (30% weight gain) is selected for the Barrier Coated Amphetamine—cation exchange resin complex—matrix.

| Ingredients | % w/w |
| --- | --- |
| Barrier Coated Amphetamine-cation exchange resin complex-matrix | 4.583 |
| Uncoated Amphetamine-cation exchange resin complex | 9.68 |
| Dextroamphetamine Saccharate | 0.356 |
| Amphetamine sulfate | 0.511 |

-continued

| Ingredients | % w/w |
|---|---|
| Mannitol, USP | 53.67 |
| Xanthan gum, NF (Gumixan ™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid ® 244FP) | 0.2 |
| Talc, USP | 1.0 |
| Magnesium stearate, NF | 0.5 |
| Total | 100.0 |

The extended release chewable tablets containing amphetamines are prepared as follows. Weigh the mannitol and microcrystalline cellulose and guar gum (Avicel® CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Saccharate and Amphetamine sulfate are weighed and passed through a #40 mesh screen. The screened material is added into a 'V'-Blender. Mix the powder blend for 25 minutes. Weigh Magnesium Stearate and pass through #40 mesh screen. Add the screened material into 'V'-Blender. Mix this powder blend for 5 minutes. The material from the Blender is unloaded and compressed into tablets by adjusting the appropriate tablet weight and hardness.

Example 8—Amphetamine Extended Release (ER) Chewable Tablets Equivalent to 20 mg Amphetamine Free Base In the following study, an ethylcellulose barrier coating of Example D1 (30% weight gain) is selected for the Barrier Coated Amphetamine—cation exchange resin complex—matrix.

| Ingredients | % w/w |
|---|---|
| Barrier Coated Amphetamine-cation exchange resin complex-matrix | 4.583 |
| Uncoated Amphetamine-cation exchange resin complex | 9.68 |
| Dextroamphetamine Sulfate, USP | 0.356 |
| Amphetamine Aspartate Monohydrate | 0.511 |
| Mannitol, USP | 53.67 |
| Xanthan gum, NF (Gumixan ™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid ® 244FP) | 0.2 |
| Talc, USP | 1.0 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender Mix the powder blend for 25 minutes. Weigh Magnesium Stearate and pass through #40 mesh screen. Add the screened material into 'V'-Blender. Mix this powder blend for 5 minutes. The material from the Blender is unloaded and compressed into tablets by adjusting the appropriate tablet weight and hardness.

Example 9—Amphetamine Extended Release (ER) Chewable Tablets Equivalent to 20 mg Amphetamine Free Base In the following study, a cellulose acetate coating of Example F (25% weight gain) is selected for the Barrier Coated Amphetamine—cation exchange resin complex—matrix.

| Ingredients | % w/w |
|---|---|
| Barrier Coated Amphetamine-cation exchange resin complex-matrix | 4.583 |
| Uncoated Amphetamine-cation exchange resin complex | 9.68 |
| Dextroamphetamine Sulfate, USP | 0.356 |
| Amphetamine Aspartate Monohydrate | 0.511 |
| Mannitol, USP | 53.67 |
| Xanthan gum, NF (Gumixan ™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid ® 244FP) | 0.2 |
| Talc, USP | 1.0 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender. Mix the powder blend for 25 minutes. Weigh Magnesium Stearate and pass through #40 mesh screen. Add the screened material into 'V'-Blender. Mix this powder blend for 5 minutes. The material from the Blender is unloaded and compressed into tablets by adjusting the appropriate tablet weight and hardness.

Example 10—Amphetamine Extended Release (ER) Chewable Tablets Equivalent to 20 mg Amphetamine Free Base In the following study, an acrylate based barrier coating of Example E (30% weight gain) is selected for the Barrier Coated Amphetamine—cation exchange resin complex—matrix.

| Ingredients | % w/w |
|---|---|
| Barrier Coated Amphetamine-cation exchange resin complex-matrix | 4.583 |

-continued

| Ingredients | % w/w |
|---|---|
| Uncoated Amphetamine-cation exchange resin complex | 9.68 |
| Dextroamphetamine Sulfate, USP | 0.356 |
| Amphetamine Aspartate Monohydrate | 0.511 |
| Mannitol, USP | 53.67 |
| Xanthan gum, NF (Gumixan ™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid ® 244FP) | 0.2 |
| Talc, USP | 1.0 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, KollidonR CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender. Mix the powder blend for 25 minutes. Weigh Magnesium Stearate and pass through #40 mesh screen. Add the screened material into 'V'-Blender. Mix this powder blend for 5 minutes. The material from the Blender is unloaded and compressed into tablets by adjusting the appropriate tablet weight and hardness.

Example 11—Amphetamine Extended Release (ER) Chewable Tablets Equivalent to 10 mg Amphetamine Free Base In the following study, a polyvinylacetate barrier coating of Example C1 (30% weight gain) is selected for the Barrier Coated Amphetamine—cation exchange resin complex—matrix.

| Ingredients | % w/w |
|---|---|
| Barrier Coated Amphetamine-cation exchange resin complex-matrix [1] | 2.29 |
| Uncoated Amphetamine-cation exchange resin complex [1] | 4.84 |
| Dextroamphetamine Sulfate, USP | 0.178 |
| Amphetamine Aspartate Monohydrate[2] | 0.255 |
| Mannitol, USP [3] | 61.23 |
| Xanthan gum, NF (Gumixan ™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid ® 244FP) | 0.2 |
| Talc, USP | 1.0 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex of Example A, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender. Mix the powder blend for 25 minutes. Weigh Magnesium Stearate and pass through #40 mesh screen. Add the screened material into 'V'-Blender. Mix this powder blend for 5 minutes. The material from the Blender is unloaded and compressed into tablets by adjusting the appropriate tablet weight and hardness.

Example 12—Amphetamine Extended Release (ER) Chewable Tablets Equivalent to 5 mg Amphetamine Free Base In the following study, a polyvinylacetate barrier coating of Example C1 (30% weight gain) is selected for the Coated Amphetamine—cation exchange resin complex—matrix.

| Ingredients | % w/w |
|---|---|
| Barrier Coated Amphetamine-cation exchange resin complex-matrix [1] | 1.72 |
| Uncoated Amphetamine-cation exchange resin complex [1] | 1.99 |
| Dextroamphetamine Sulfate, USP | 0.089 |
| Amphetamine Aspartate Monohydrate[2] | 0.128 |
| Mannitol, USP [3] | 65.9 |
| Talc, USP | 1.0 |
| Xanthan gum, NF (Gumixan ™ K) | 0.5 |
| Crospovidone, NF (Kollidon ® CL), Type A | 12 |
| Microcrystalline cellulose and Guargum (Avicel ® CE | 15 |
| Sucralose, NF | 1.5 |
| Bubblegum Flavor | 0.5 |
| Silicon dioxide, NF (Syloid ® 244FP) | 0.2 |
| Magnesium stearate, NF | 0.5 |
| Total | 100.0 |

The extended release chewable tablets containing amphetamines are prepared as follows. Weigh the mannitol and microcrystalline cellulose and guar gum (Avicel CE15), and screen through a 20 mesh screen. Add the screened material into 'V'-Blender. The xanthan gum, Kollidon® CL, sucralose, citric acid, bubble gum flavor, silicon dioxide, talc, Uncoated Amphetamine—cation exchange resin complex, Coated Amphetamine—cation exchange resin complex—matrix, Dextroamphetamine Sulfate and Amphetamine Aspartate Monohydrate are weighed and passed through a #40 mesh screen. The screened material is added into a 'V'-Blender. Mix the powder blend for 25 minutes. Weigh Magnesium Stearate and pass through #40 mesh screen. Add the screened material into 'V'-Blender. Mix this powder blend for 5 minutes. The material from the Blender is unloaded and compressed into tablets by adjusting the appropriate tablet weight and hardness.

Example 13—Efficacy Study of Amphetamine Extended Release (ER) Tablets for Pediatric Use An amphetamine ER tablet prepared as described in the preceding example, containing the equivalent of 2.5 mg/mL amphetamine base and a ratio of approximately 3:1 of d-amphetamine to l-amphetamine, is tested. The test involves children with attention deficit hyperactivity disorder (ADHD) aged 6-12 years old.

This formulation is assessed to study the attention and behavior of the subjects in a laboratory classroom using the Swanson, Kotkin, Agler, M-Flynn, and Pelham (SKAMP) rating scale. Subjects with ADHD enter a 2-week randomized, double-blind, crossover treatment of the individually optimized dose of the amphetamine ER tablet (2.5 mg/daily to a maximum of 20 mg/daily) or placebo, administered once a day in the morning. At the end of each week, schoolteachers and raters evaluate the attention and behavior of the subjects in a laboratory classroom using the Swanson, Kotkin, Agler, M-Flynn, and Pelham (SKAMP) rating scale. SKAMP scores which are statistically significantly lower (improved) during treatment with the amphetamine ER tablet of the invention as compared to placebo are deemed efficacious. The earliest tested time point assessed may be 1 hour post-dose and efficacy may be assessed again at about 13 hours post-dose.

Objective PK measurement occurs over 28 hours post-dose as a primary end point. Pediatric subjects are normally dosed in a manner to provide pharmacologic treatment primarily for the academic time period of the day as well as the after-school period. Two (2) age groups of pediatric subjects may be included in the study: subjects between the ages of 6 to 9 and subjects between the ages of 10 to 12. A total of 12 subjects. This allows the comparison of PK parameters in younger and older pediatric patients treated with a single mid-range dose of amphetamine. A "mid-range" amphetamine dose refers to a comparison of 10 mg amphetamine base to equivalents of other amphetamine products currently FDA approved for the treatment of ADHD in pediatric patients. The study is performed under fasting conditions.

For PK analyses of amphetamine, 9 blood samples are collected in total from each subject. Samples are collected at pre-dose Day 1 (Time 0) and at the following times: Day 1:1, 3, 4, 6, 8, 10, 12, and 28 hours post dose (Day 2). Time after dosing begins when amphetamine is administered to the subject. With the exception of the 0 (pre-dose) and 28 hour sample, samples are collected within ±5 minutes of the scheduled post-dose time. The pre-dose sample is collected up to 2 hours before dosing. The 28 hour sample is collected 26-30 hours post-dose.

Example 14—Pharmacological Study with Amphetamine Extended Release (ER) Chewable Tablets Equivalent to 20 mg Amphetamine Free Base A 20 mg bio-study is conducted using 20 mg AMP ER tablets including (1) chewable tablets under fast and fed conditions, (2) swallowed whole tablets under fed condition, versus suspension under fasted at the same dose (20 mg). The reference drug product is DYANAVEL liquid suspension product [TRIS PHARMA]. An open label, single dose, randomized, four way, cross over relative bioavailability study in 31 healthy subjects is conducted. Results of the pivotal bio study demonstrated bioequivalence between the tablet (independent of mode of administration: chewed or whole) and DYANAVEL AMP suspension reference product in fasted condition. The data also shows increase in the early exposure and also bioequivalence for the chewable tablet in fed condition.

This study compares the bioavailability of the test ER chewable tablet formulation, administered chewed or swallowed intact, to an equivalent 20 mg dose of the reference product (Dyanavel® XR ER Oral Suspension) administered under fasted conditions. Furthermore, the relative bioavailability of the test ER chewable tablet is investigated under fasted and fed conditions in order to assess a possible food effect. This study also assesses the test ER chewable tablet with respect to the dose dumping potential by visual inspection of the individual concentrations versus time profiles. Bioavailability is assessed upon determination of the rate and extent of absorption of a drug in a biological system. AUC and Cmax are common PK parameters obtained to estimate the rate and extent of absorption of a drug product. A sampling schedule was designed for this study to ensure that the AUC, including partial AUCs, and Cmax parameters were adequately assessed from collected plasma. By implementing a crossover design, the estimated PK parameters for each formulation (and respective treatment) are compared within the same subject. Relative bioavailability between the treatment contrasts of interest was determined by a statistical comparison of the AUC, including partial AUCs, and Cmax parameters for d-amphetamine and l-amphetamine.

In each period, subjects received one of the following 4 treatments:

Treatment A—Test Product (as a chewable tablet): one tablet administered after an overnight fast of at least 10 hours Treatment B—Test Product (as a chewable tablet): one tablet administered 30 minutes after the start of a high-fat, high-calorie breakfast Treatment C—Test Product (as a whole tablet): one tablet administered after an overnight fast of at least 10 hours Treatment D—Reference Product: 20 mg (8 mL ER oral suspension [2.5 mg/mL]) administered after an overnight fast of at least 10 hours Pharmacokinetic analysis is performed on available data from subjects in the PK dataset. The post-dose sample collection times are used in the PK analysis. PK parameters/observations may be estimated for d-amphetamine and l-amphetamine using a non-compartmental approach in Phoenix® WinNonlin® (version 6.4):

AUC0-t: The area under the analyte concentration versus time curve, from time zero (0) to the time of the last measurable analyte concentration (t), as calculated by the linear trapezoidal method.

AUC0-5: The area under the analyte concentration versus time curve, from time zero (0) to 5 hours after dosing, as calculated by the linear trapezoidal method. AUC0-5 was based on all measurable concentrations within the first 5 hours and is presented as AUC0-5.

AUC5-t: The area under the analyte concentration versus time curve, from 5 hours after dosing to the last measurable analyte concentration (t), as calculated by the linear trapezoidal method.

AUC0-∞: The area under the analyte concentration versus time curve from time zero to infinity. AUC0-∞=AUC0-t+Ct/kel, where Ct is the last measurable analyte concentration. kel: The apparent first-order elimination rate constant.

Cmax: Maximum measured analyte concentration over the sampling period.

Tmax: Time of the maximum measured analyte concentration over the sampling period.

AUC0-t/AUC0-∞: The ratio of AUC0-t to AUC0-∞.

TLIN: Start time for linear regression.

LQCT: Last quantifiable concentration time.

R: Correlation coefficient obtained from regression analysis.

Kel, $t_{half}$ and $AUC_{0-\infty}$ parameters were not estimated for concentration-time profiles where the terminal linear phase was not clearly defined.

Individual and mean plasma concentrations versus time curves were plotted.

Descriptive statistics for the PK parameters of d-amphetamine and l-amphetamine are calculated. Descriptive statistics included number of observations, arithmetic mean, SD, geometric mean (where applicable), coefficient of variation (CV), median, minimum, and maximum.

Statistical analysis is performed on quality assured data, with unbalanced groups if necessary, from subjects in the statistical dataset. The PROC GLM procedure from SAS (version 9.4) was used. Analysis of variance (ANOVA) is performed on log-transformed $AUC_{0-5}$, $AUC_{5-t}$, $AUC_{0-t}$, $AUC_{0-\infty}$, and Cmax parameters. The significance of the sequence, period, treatment, and subject(sequence) effects are tested.

Using the same statistical model, the least-squares-means, the differences between the treatments least-squares-means and the corresponding standard errors of these differences are estimated for log-transformed $AUC_{0-5}$, $AUC_{5-t}$, $AUC_{0-t}$, $AUC_{0-\infty}$, and Cmax parameters. Based on these statistics, the ratios of the geometric means for treatments and the corresponding 90% CIs are calculated for the following comparisons:

Primary Objectives:
Relative Bioavailability (Treatment A versus Treatment D; Treatment C versus Treatment D); and
Food Effect (Treatment B versus Treatment A).
Secondary Objectives:
Relative Bioavailability (Treatment A versus Treatment C).

Figure 2:
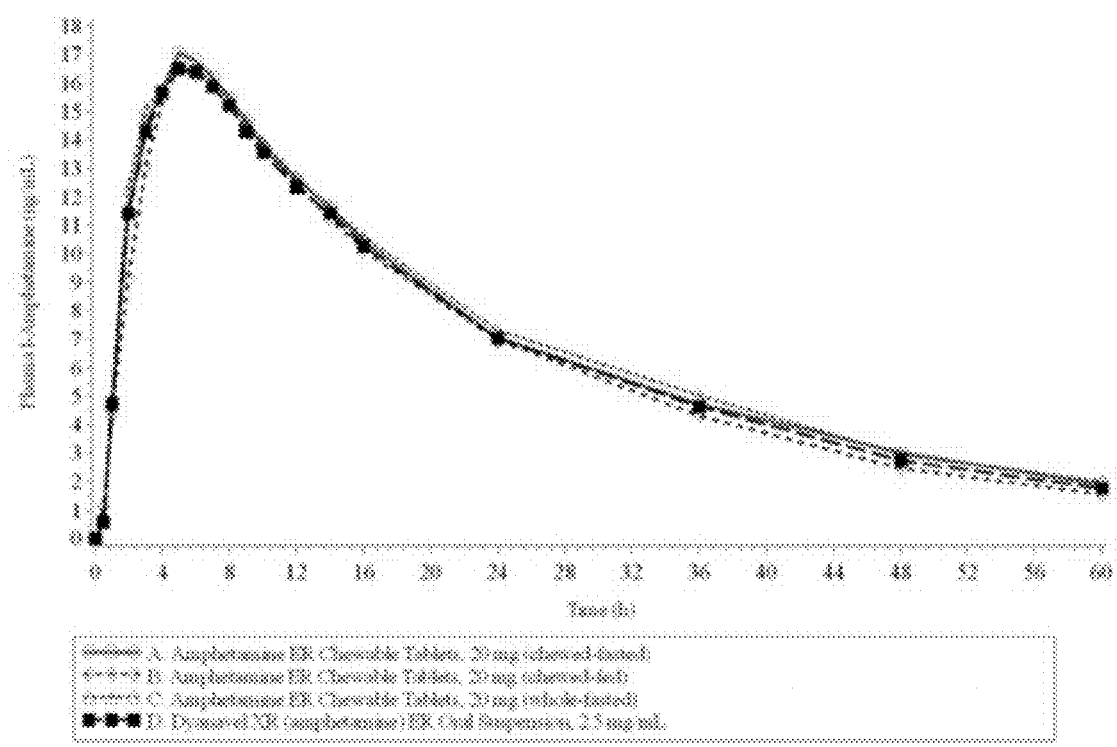
FIG. 2 provides a graph of the plasma concentration profile for l-amphetamine following administration of a chewed 20 mg tablet under fasted conditions (A), a chewed tablet under fed conditions (B) or a tablet swallowed whole (C), as compared to a liquid ER suspension product (line D).

See, FIGS. 1A-1D and FIGS. 2A-2D.

All patents, patent publications, and other publications listed in this specification, including U.S. Provisional Patent Application No. 62/562,464, filed Sep. 24, 2017, are incorporated herein by reference. While the invention has been described with reference to a particularly preferred embodiment, it will be appreciated that modifications can be made without departing from the spirit of the invention. Such modifications are intended to fall within the scope of the appended claims.

What is claimed is:

1. An extended release amphetamine tablet,
   wherein the tablet provides a single plasma concentration peak for d-amphetamine and for l-amphetamine, wherein the tablet lacks a pH-dependent coating which provides delayed release to an amphetamine component, and wherein the tablet further comprises:
   (A) a modified release amphetamine component which comprises at least one modified release barrier coated amphetamine—cation exchange resin complex—optional matrix which comprises (i) two or more amphetamines bound to the same cation exchange resin, wherein when the optional matrix is present, the amphetamine—cation exchange resin complex—matrix further comprises a hydrophilic polymer or copolymer or a hydrophobic polymer and (ii) a pH-independent barrier coating which provides a modified release to the two or more amphetamines, wherein the two or more amphetamines are at least a d-amphetamine and an l-amphetamine, wherein the d-amphetamine and the l-amphetamine are provided by d-amphetamine and at least one of (d,l)-amphetamine and l-amphetamine, wherein the modified release amphetamine component (A) comprises at least 5% w/w of the total amphetamines in the tablet based on the weight of free amphetamine base; and
   (B) immediate release amphetamine components which comprise greater than 70% w/w of the total amphetamines in the tablet based on the total weight of free amphetamine base in the tablet, and wherein the immediate release amphetamine components further comprise:
   (i) a first immediate release amphetamine component which comprises d-amphetamine or a pharmaceutically acceptable salt thereof, and l-amphetamine or a pharmaceutically acceptable salt thereof, or mixtures thereof, wherein the d- and l-amphetamine are provided by d-amphetamine and at least one of (d,l)-amphetamine and l-amphetamine, wherein the immediate release amphetamine component B(i) comprises at least 5% w/w of the total amphetamines in the tablet based on the weight of free amphetamine base; and
   (ii) a second immediate release amphetamine component which comprises an amphetamine—cation exchange resin complex in an optional matrix, wherein the amphetamine—cation exchange resin complex—optional matrix comprises at least a d-amphetamine (d, l)-amphetamine and an l-amphetamine both bound to the same cation exchange resin, wherein the d-amphetamine and the l-amphetamine are provided by d-amphetamine and at least one of (d, l)-amphetamine or l-amphetamine, wherein the immediate release component B(ii) comprises at least 5% w/w of the total amphetamines in the tablet based on the weight of the free amphetamine base.

2. The tablet according to claim 1, wherein the amphetamines in first and second immediate release amphetamine component of (B) are about 80% w/w of the amphetamines in the total tablet.

3. The tablet according to claim 2, wherein the amphetamines in the first immediate release amphetamine component of (B)(i) are about 20% w/w of the total amphetamines in the tablet.

4. The tablet according to claim 2, wherein the amphetamines in the second immediate release amphetamine component (B)(ii) are about 60% w/w of the total amphetamines in the tablet.

5. The tablet according to claim 1, wherein the tablet comprises one or more of the pharmacokinetic parameters for d-amphetamine following dosing subjects under fasted conditions with the tablet comprising the equivalent of 20 mg total amphetamines:
   (a) as determined following a chewed dose: an arithmetic mean $AUC_{0-\infty}$ of about 965 to about 1508 ng-h/mL, a geometric mean $AUC_{0-\infty}$ of about 931 ng-h/mL to about 1455 ng-h/mL h/mL, an arithmetic mean $AUC_{0-2}$ of about 24.8 ng-h/mL to about 38.79 ng-h/mL or a geometric mean $AUC_{0-2}$ of about 22.85 ng-hr/mL to about 35.72 ng-hr/mL, an arithmetic mean $AUC_{0-5}$ of about 138 ng-h/mL to about 216 ng-h/mL or a geometric mean $AUC_{0-5}$ of about 134 ng-hr/mL to about 209 ng-hr/mL, an arithmetic mean $AUC_{5-t}$ 767 ng-hr/mL to about 1199 ng-hr/mL or a geometric mean $AUC_{5-t}$ of about of about 740 ng-h/mL to about 1156 ng-h/mL, an arithmetic mean $C_{max}$ of about 44 ng/mL to about 69 ng/mL, a geometric mean $C_{max}$ of about 43 ng/mL to about 68 ng/mL, or a $T_{max}$ of about 3 hours to about 7 hours, or
   (b) for a whole swallowed tablet dose: an arithmetic $AUC_{0-\infty}$ of about 972 to about 1519 ng-h/mL, a geometric mean $AUC_{0-\infty}$ of about 948 ng-h/mL to about 1481 ng-h/mL h/mL, an arithmetic mean $AUC_{0-2}$ of about 26.30 ng-h/mL to about 41.10 ng-h/mL or a geometric mean $AUC_{0-2}$ of about 24.48 ng-hr/mL to about 38.25 ng-hr/mL, an arithmetic mean $AUC_{0-5}$ of about 141 ng-h/mL to about 220 ng-h/mL or a geometric mean $AUC_{0-5}$ of about 138 ng-hr/mL to about 215 ng-hr/mL, an arithmetic mean $AUC_{5-t}$ of about 768 ng-h/mL to about 1200 ng-h/mL, or a geometric mean $AUC_{5-t}$ of about 749 ng-hr/mL to about 1170 ng-hr/mL, an arithmetic mean $C_{max}$ of about 42 ng/mL to 66 ng/mL, a geometric mean $C_{max}$ of about 42 ng/mL to 66 ng/mL, an arithmetic mean or a $T_{max}$ of about 2 hours to about 9 hours.

6. The tablet according to claim 5, wherein the tablet comprises one or more of the pharmacokinetic parameters for d-amphetamine following dosing subjects under fasted conditions with the tablet comprising the equivalent of 20 mg total amphetamines:

for a chewed dose: an arithmetic mean $AUC_{0-\infty}$ of about 1206 ng-h/mL, a geometric mean $AUC_{0-\infty}$ of about 1164 ng-hr/mL, an arithmetic mean $AUC_{0-2}$ of about 31 ng-h/mL, a geometric mean $AUC_{0-2}$ of about 29 ng-hr/mL, an arithmetic mean $AUC_{0-5}$ of about 173 ng-h/mL, a geometric mean $AUC_{0-5}$ of about 167 ng-hr/mL, an arithmetic mean $AUC_{5-t}$ of about 959 ng-h/mL, a geometric mean $AUC_{5-t}$ of about 925 ng-hr/mL, an arithmetic mean $C_{max}$ of about 55 ng/mL, a geometric mean $c_{max}$ of about 54 ng/mL, or a $T_{max}$ of about 5 hours; or for a whole swallowed dose: an arithmetic mean $AUC_{0-\infty}$ of about 1215 ng-h/mL, a geometric mean $AUC_{0-\infty}$ of about 1185 ng-hr/mL, an arithmetic mean $AUC_{0-2}$ of about 33 ng-h/mL, a geometric mean $AUC_{0-2}$ of about 31 ng-hr/mL, an arithmetic mean $AUC_{0-5}$ of about 176 ng-h/mL, a geometric mean $AUC_{0-5}$ of about 172 ng-hr/mL, an arithmetic mean $AUC_{5-t}$ of about 960 ng-h/mL, a geometric mean $AUC_{5-t}$ of about 936 ng-hr/mL, an arithmetic mean $C_{max}$ of about 53 ng/mL, a geometric mean $C_{max}$ of about 53 ng/mL, or a $T_{max}$ of about 5 hours.

7. The tablet according to claim 1, wherein the tablet comprises one or more of the pharmacokinetic parameters for l-amphetamine following dosing subjects under fasted conditions with the tablet comprising the equivalent of 20 mg total amphetamines:

(a) as determined following a chewed dose: an arithmetic mean $AUC_{0-\infty}$ of about 378 to about 591 ng-h/mL, a geometric mean $AUC_{0-\infty}$ of about 362 ng-h/mL to about 566 ng-h/mL, an arithmetic mean $AUC_{0-2}$ of about 7.57 ng-h/mL to about 11.85 ng-h/mL or a geometric mean $AUC_{0-2}$ of about 6.97 ng-hr/mL to about 10.89 ng-hr/mL, an arithmetic mean $AUC_{0-5}$ of about 43 ng-h/mL to about 68 ng-h/mL, a geometric mean $AUC_{0-5}$ of about 42 ng-hr/mL to about 65 ng-hr/mL, an arithmetic mean $AUC_{5-t}$ 292 ng-hr/mL to about 456 ng-hr/mL, a geometric mean $AUC_{5-t}$ of about 280 ng-h/mL to about 438 ng-h/mL, an arithmetic mean $C_{max}$ of about 13.6 ng/mL to about 21.25 ng/mL, a geometric mean $C_{max}$ of about 3.6 ng/mL to about 21.25 ng/mL, or a $T_{max}$ of about 3 hours to about 7 hours, or (b) as determined following a whole swallowed dose: an arithmetic mean $AUC_{0-\infty}$ of about 385 ng-h/mL to about 601 ng-h/mL, a geometric mean $AUC_{0-\infty}$ of about 373 ng-h/mL to about 583 ng-h/mL h/mL, an arithmetic mean $AUC_{0-2}$ of about 8.09 ng-h/mL to about 12.64 ng-h/mL or a geometric mean $AUC_{0-2}$ of about 7.49 ng-hr/mL to about 11.71 ng-hr/mL an arithmetic mean $AUC_{0-5}$ of about 44 ng-h/mL to about 69 ng-h/mL, a geometric mean $AUC_{0-5}$ of about 43 ng-hr/mL to about 68 ng-hr/mL, an arithmetic mean $AUC_{5-t}$ of about 294 ng-hr/mL to about 459 ng-hr/mL, a geometric mean $AUC_{5-t}$ of about 286 ng-h/mL to about 446 ng-h/mL, an arithmetic mean $C_{max}$ of about 13.6 ng/mL to about 21.25 ng/mL, a geometric mean $C_{max}$ of about 3.6 ng/mL to about 21.25 ng/mL, or a $T_{max}$ of about 2 hours to about 9 hours.

8. The tablet according to claim 7, wherein the tablet comprises one or more of the pharmacokinetic parameters for l-amphetamine following dosing subjects under fasted conditions with the tablet comprising 20 mg total amphetamines:

(a) for a chewed dose: an arithmetic mean $AUC_{0-\infty}$ of about 473 ng-h/mL, a geometric mean $AUC_{0-\infty}$ of about 453 ng-hr/mL, an arithmetic mean $AUC_{0-2}$ of about 8.43 ng-h/mL, a geometric mean $AUC_{0-2}$ of about 7.65 ng-hr/mL an arithmetic mean $AUC_{0-5}$ of about 54 ng-h/mL, a geometric mean $AUC_{0-5}$ of about 52 ng-hr/mL, an arithmetic mean $AUC_{5-t}$ of about 365 ng-h/mL, a geometric mean $AUC_{5-t}$ of about 350 ng-hr/mL, an arithmetic mean $C_{max}$ of about 17 ng/mL, a geometric mean $C_{max}$ of about 17 ng/mL, or a median $T_{max}$ of about 5 hours; or (b) for a whole swallowed dose: an arithmetic mean $AUC_{0-\infty}$ of about 481 ng-h/mL, a geometric mean $AUC_{0-\infty}$ of about 466 ng-hr/mL, an arithmetic mean $AUC_{0-5}$ of about 55 ng-h/mL, an arithmetic mean $AUC_{0-2}$ of about 10.11 ng-h/mL, a geometric mean $AUC_{0-2}$ of about 9.64 ng-hr/mL a geometric mean $AUC_{0-5}$ of about 54 ng-hr/mL, an arithmetic mean $AUC_{5-t}$ of about 367 ng-h/mL, a geometric mean $AUC_{5-t}$ of about 357 ng-hr/mL, an arithmetic mean $c_{max}$ of about 17 ng/mL, a geometric mean $c_{max}$ of about 17 ng/mL, or a median $T_{max}$ of about 5 hours.

9. The tablet according to claim 1, wherein the tablet has a plasma pharmacokinetic profile for d-amphetamine which is about 80% to about 125% of one or more of:

a geometric mean $AUC_t$ of about 821 ng-h/mL, a geometric mean $AUC_{inf}$ of about 1013 ng-h/mL, a geometric mean $C_{max}$ of about 53 ng/mL, a geometric mean $T_{max}$ of about 3.85, an arithmetic mean $AUC_t$ of about 857 ng-h/mL, an arithmetic mean about $AUC_{inf}$ of about 1061 ng-h/mL, an arithmetic mean $C_{max}$ of about 55 ng/mL, or an arithmetic mean $T_{max}$ of about 4, as measured in children 6-12 years old under fasting conditions following dosing with the tablet having the equivalent of 20 mg of amphetamine base; or an arithmetic mean $AUC_{0-4}$ of about 144 ng-h/mL, an arithmetic mean $AUC_{4-t}$ of about 1000 ng-h/mL, an arithmetic mean $AUC_{0-5}$ of about 196 ng-h/mL, an arithmetic mean $AUC_{5-t}$ of about 948 ng-h/mL, a geometric mean $AUC_{0-4}$ of about 139 ng-h/mL, a geometric mean $AUC_{4-t}$ of about 977 ng-h/mL, a geometric mean $AUC_{0-5}$ of about 191 ng-h/mL, or a geometric mean $AUC_{5-t}$ of about 926 ng-h/mL, as measured in children 6-12 years old under fasting conditions following dosing with the tablet having the equivalent of 20 mg of amphetamine base.

10. The tablet according to claim 9, wherein the pharmacokinetic profile for d-amphetamine is about 90% to about 110% of one or more of the arithmetic mean, a geometric mean $AUC_t$, geometric mean $AUC_{inf}$, a geometric mean $C_{max}$, a geometric mean $T_{max}$, arithmetic mean $AUC_t$, an arithmetic mean about $AUC_{inf}$, arithmetic mean $C_{max}$, or an arithmetic mean $T_{max}$, or arithmetic mean $AUC_{0-4}$, arithmetic mean $AUC_{4-t}$, arithmetic mean $AUC_{0-5}$, arithmetic mean $AUC_{5-t}$, geometric mean $AUC_{0-4}$, geometric mean $AUC_{4-t}$, a geometric mean $AUC_{0-5}$, or a geometric mean $AUC_{5-t}$, as determined using a 90% confidence interval.

11. The tablet according to claim 1, wherein the tablet has a plasma pharmacokinetic profile for l-amphetamine which is about 80% to about 125% of one or more of one or more:
a geometric mean $AUC_t$ of about 274 ng-h/mL, a geometric mean about AUCinf of about 362 ng-h/mL, a geometric mean $c_{max}$ of about 16 ng/mL, a geometric mean $T_{max}$ of about 4.5, an arithmetic mean $AUC_t$ of about 286 ng-h/mL, an arithmetic mean about $AUC_{inf}$ of about 380 ng-h/mL, an arithmetic mean $C_{max}$ of about 17 ng/mL, or an arithmetic mean $T_{max}$ of about 4.5, as measured in children 6-12 years old under fasting conditions following dosing with the tablet having the equivalent of 20 mg of amphetamine base; or an arithmetic mean $AUC_{0-4}$ of about 45 ng-h/mL, an arithmetic mean $AUC_{4-t}$ of about 380 ng-h/mL, an arithmetic mean $AUC_{0-5}$ of about 62 ng-h/mL, an arithmetic mean $AUC_{5-t}$ of about 363 ng-h/mL, a geometric mean $AUC_{0-4}$ of about 44 ng-h/mL, a geometric mean $AUC_{4-t}$ of about 370 ng-h/mL, a geometric mean $AUC_{0-5}$ of about 60 ng-h/mL, or a geometric mean $AUC_{5-t}$ of about 354 ng-h/mL, as measured in adults under fasting conditions following dosing with the tablet having the equivalent of 20 mg of amphetamine base.

12. The tablet according to claim 11, wherein the pharmacokinetic profile for l-amphetamine is about 90% to about 110% of one or more of the arithmetic mean, geometric mean $AUC_t$, geometric mean AUCinf, a geometric mean Cmax, a geometric mean Tmax, arithmetic mean AUCt, an arithmetic mean about AUCinf, arithmetic mean Cmax, or an arithmetic mean Tmax, or arithmetic mean AUC0-4, arithmetic mean AUC4-t, arithmetic mean AUC0-5, arithmetic mean AUC5-t, geometric mean AUC0-4, geometric mean AUC4-t, a geometric mean AUC0-5, or a geometric mean AUC5-t, as determined using a 90% confidence interval.

13. The tablet according to claim 1, wherein the modified release component (A) further comprises a water insoluble polymer or copolymer or a hydrophilic polymer which forms a matrix with the amphetamine—cation exchange resin complex of (i).

14. The tablet according to claim 1, wherein the modified release component (A) comprises (d,l)-amphetamine and d-amphetamine.

15. The tablet according to claim 1, wherein the immediate release component (C) comprises (d,l)-amphetamine and d-amphetamine.

16. The tablet according to claim 1, wherein the immediate release amphetamine—cation exchange resin complex of (C) has an optional matrix and a coating that permits release of the amphetamine in less than 45 minutes following administration of the tablet to a patient.

17. The tablet according to claim 1, wherein the immediate release component (B) comprises: (a) (d, l)-amphetamine or a pharmaceutically acceptable salt thereof, and d-amphetamine or pharmaceutically acceptable salt thereof, or a mixture thereof; or (l)-amphetamine or a pharmaceutically acceptable salt thereof, (d)-amphetamine or a pharmaceutically acceptable salt thereof, or mixtures thereof, optionally further comprising (d,l)-amphetamine or a salt thereof.

18. The tablet according to claim 1, wherein the tablet comprises at least two different amphetamine salts counterions.

19. The tablet according to claim 1, wherein the tablet is a chewable tablet.

20. The tablet according to claim 19, wherein the chewable tablet is also an orally dissolving or orally disintegrating or dispersible tablet.

21. The tablet according to claim 15, wherein the barrier coating is pH-independent and comprises (a) a cured, water-permeable, non-ionic, pH-independent barrier coating comprising polyvinylacetate, a stabilizer, and a plasticizer; (b) an ionic, pH-independent, acrylic based coating comprising a polymer or copolymer comprising ethyl acrylate and methyl methacrylate applied as an aqueous dispersion; (c) a solvent-based ethylcellulose, optionally with a plasticize, or (d) cellulose acetate and a plasticizer.

22. The tablet according to claim 15, wherein said tablet does not exceed 500 mg in total weight.

23. The tablet according to claim 15, wherein the therapeutic effect lasts up to about 18 hours following post dose administration to a patient.

24. The tablet according to claim 15, wherein each of the (d,l)-amphetamine and the d-amphetamine of modified release component (A) is bound to a separate cation exchange resin and/or each of the (d,l)-amphetamine and the d-amphetamine of the immediate release component (C) is bound to a separate cation exchange resin.

25. The tablet according to claim 15, wherein the barrier coating is a cured, water-insoluble, water-permeable, non-ionic, pH-independent barrier coating comprises about 70 to about 90% w/w polyvinylacetate, a stabilizer, and about 2 to about 10% w/w of a plasticizer.

26. The tablet according to claim 25, wherein the plasticizer comprises triacetin.

27. An extended release amphetamine solid composition, wherein the composition provides an immediate release and about a 13-hour therapeutic effect for d-amphetamine and for l-amphetamine, a single plasma concentration peak for d-amphetamine and for l-amphetamine, wherein the tablet lacks a pH-dependent coating which provides delayed release to an amphetamine component, and wherein the composition further comprises:

(A) about 10% w/w to 30% w/w of a modified release amphetamine component which comprises at least one modified release barrier coated amphetamine—cation exchange resin complex—optional matrix which comprises (i) (d,l)- and (d)-amphetamines bound to the same cation exchange resin, wherein when the optional matrix is present, the amphetamine—cation exchange resin complex—matrix further comprises a hydrophilic polymer or copolymer or a hydrophobic polymer and (ii) a water-insoluble, water-permeable, pH-independent, barrier coating comprising a pH-independent, water-insoluble polymer and a plasticizer, which barrier coating provides a modified release to the amphetamines;

(B) a first immediate release amphetamine component which comprises d-amphetamine or a pharmaceutically acceptable salt thereof, and l-amphetamine or a pharmaceutically acceptable salt thereof, or mixtures thereof, wherein the d- and l-amphetamine are provided by d-amphetamine and at least one of (d,l)-amphetamine and l-amphetamine, wherein the total amount of the first immediate release amphetamine component provides at least 15% w/w of the amphetamine components in the composition; and (C) a second immediate release amphetamine component which comprises an amphetamine—cation exchange resin complex in an optional matrix, wherein the amphetamine—cation exchange resin complex—optional matrix comprises at least a d-amphetamine and an l-amphetamine both bound to the same cation exchange resin, wherein the d-amphetamine and the l-amphetamine are provided by d-amphetamine and at least one of (d, l)-amphetamine or l-amphetamine, wherein the total amount of the second immediate release amphetamine component provides at least 15% w/w of the amphetamine components in the composition;

and wherein the immediate release component comprises at least 70% w/w immediate release amphetamines based on the total weight of free amphetamine base in the composition.

28. The composition according to claim 27, wherein the composition is an orally dissolving or dispersible tablet.

29. The composition according to claim 27, wherein the composition is a chewable tablet.

30. The composition according to claim 27, wherein the composition is a scored tablet.

31. The composition according to claim 27, wherein the composition comprises a dose of 5 mg to 20 mg amphetamine, as calculated based on the amount of free amphetamine base.

32. A method of treating a patient having attention deficit hyperactivity disorder (ADHD) comprising administering a composition according to claim 1 once a day.

33. A method of treating a patient having attention deficit hyperactivity disorder (ADHD) comprising administering a composition according to claim 27 once a day.

34. An extended release amphetamine tablet,
wherein the tablet provides an immediate release and at least about a 13-hour therapeutic effect for d-amphetamine and for l-amphetamine, a single plasma concentration peak for d-amphetamine and for l-amphetamine, and wherein the tablet further comprises:
(A) a modified release amphetamine component which comprises at least one modified release barrier coated amphetamine—cation exchange resin complex—optional matrix which comprises (i) two or more amphetamines bound to the same cation exchange resin or each bound to a different cation exchange resin, wherein when the optional matrix is present, the amphetamine—cation exchange resin complex—matrix further comprises a hydrophilic polymer or copolymer or a hydrophobic polymer and (ii) a water-insoluble, water-permeable, pH-independent, barrier coating which provides a modified release to the two or more amphetamines, wherein the two or more amphetamines are at least a d-amphetamine and an l-amphetamine, wherein the d-amphetamine and the l-amphetamine are provided by d-amphetamine and at least one of (d,l)-amphetamine and l-amphetamine,
wherein the barrier coating comprises polyvinyl acetate and a plasticizer; and
wherein the ratio of d-amphetamine to l-amphetamine is about 3.2 to about 1;
(B) immediate release amphetamine components which comprise greater than 60% w/w of the total amphetamines in the tablet based on the total weight of free amphetamine base in the tablet, and wherein the immediate release amphetamine components further comprise:
(i) an immediate release amphetamine—cation exchange resin complex in an optional matrix, wherein the amphetamine—cation exchange resin complex—optional matrix comprises at least a d-amphetamine and an l-amphetamine both bound to the same cation exchange resin, wherein the d-amphetamine and the l-amphetamine are provided by d-amphetamine and at least one of (d, l)-amphetamine or l-amphetamine; and
(ii) amphetamine aspartate; and
(iii) dextroamphetamine sulfate.

35. A method of treating attention deficit hyperactivity disorder once a day comprising providing a chewable extended release tablet to a subject in need thereof in the morning, wherein the tablet comprises:
(A) a modified release amphetamine component which comprises at least one modified release barrier coated amphetamine—cation exchange resin complex—optional matrix which comprises (i) two or more amphetamines bound to the same cation exchange resin or each bound to a different cation exchange resin, wherein when the optional matrix is present, the amphetamine—cation exchange resin complex—matrix further comprises a hydrophilic polymer or copolymer or a hydrophobic polymer and (ii) a pH-independent barrier coating which provides a modified release to the two or more amphetamines, wherein the two or more amphetamines are at least a d-amphetamine and an l-amphetamine, wherein the d-amphetamine and the l-amphetamine are provided by d-amphetamine and at least one of (d,l)-amphetamine and l-amphetamine; and
(B) immediate release amphetamine components which comprise greater than 60% w/w of the total amphetamines in the tablet based on the total weight of free amphetamine base in the tablet, and wherein the immediate release amphetamine components further comprise:
(i) an amphetamine—cation exchange resin complex in an optional matrix, wherein the amphetamine—cation exchange resin complex—optional matrix comprises at least a d-amphetamine and an l-amphetamine both bound to the same cation exchange resin, wherein the d-amphetamine and the l-amphetamine are provided by d-amphetamine and at least one of (d, l)-amphetamine or l-amphetamine; and
(ii) amphetamine aspartate; and
(iii) dextroamphetamine sulfate.

36. The method according to claim 35, wherein the tablet provides therapeutic effect from 1 to 13 hours as determined in a SKAMP rating scale.

37. The method according to claim 35, wherein the Tmax is about 5.0 as determined by arithmetic or geometric mean post-dosing with a 20 mg extended-release tablet swallowed whole.

* * * * *